(12) United States Patent
Nakasuji et al.

(10) Patent No.: US 7,109,483 B2
(45) Date of Patent: Sep. 19, 2006

(54) METHOD FOR INSPECTING SUBSTRATE, SUBSTRATE INSPECTING SYSTEM AND ELECTRON BEAM APPARATUS

(75) Inventors: Mamoru Nakasuji, Kanagawa (JP); Nobuharu Noji, Kanagawa (JP); Tohru Satake, Kanagawa (JP); Toshifumi Kimba, Kanagawa (JP); Masahiro Hatakeyama, Kanagawa (JP); Kenji Watanabe, Kanagawa (JP); Hirosi Sobukawa, Kanagawa (JP); Tsutomu Karimata, Kanagawa (JP); Shoji Yoshikawa, Tokyo (JP); Shin Oowada, Kanagawa (JP); Mutsumi Saito, Kanagawa (JP); Muneki Hamashima, Saitama (JP)

(73) Assignee: Ebara Corporation, Tokyo (JP)

( * ) Notice: Subject to any disclaimer, the term of this patent is extended or adjusted under 35 U.S.C. 154(b) by 102 days.

(21) Appl. No.: 09/985,331

(22) Filed: Nov. 2, 2001

(65) Prior Publication Data
US 2002/0130262 A1    Sep. 19, 2002

(30) Foreign Application Priority Data

| Nov. 17, 2000 | (JP) | ............................. 2000-351420 |
| Nov. 30, 2000 | (JP) | ............................. 2000-364076 |
| Dec. 18, 2000 | (JP) | ............................. 2000-384036 |
| Dec. 26, 2000 | (JP) | ............................. 2000-394138 |
| Jan. 11, 2001 | (JP) | ............................. 2001-003654 |
| Jan. 17, 2001 | (JP) | ............................. 2001-008998 |
| Jan. 31, 2001 | (JP) | ............................. 2001-023422 |
| Feb. 2, 2001 | (JP) | ............................. 2001-026468 |
| Feb. 8, 2001 | (JP) | ............................. 2001-031901 |
| Feb. 8, 2001 | (JP) | ............................. 2001-031906 |
| Feb. 9, 2001 | (JP) | ............................. 2001-033599 |
| Feb. 14, 2001 | (JP) | ............................. 2001-036840 |
| Feb. 16, 2001 | (JP) | ............................. 2001-040421 |
| Mar. 16, 2001 | (JP) | ............................. 2001-075863 |
| Apr. 23, 2001 | (JP) | ............................. 2001-124219 |
| May 28, 2001 | (JP) | ............................. 2001-158571 |

(51) Int. Cl.
*H01J 37/06* (2006.01)

(52) U.S. Cl. ................. 250/310; 250/307; 250/311
(58) Field of Classification Search ................ 250/310
See application file for complete search history.

(56) References Cited

U.S. PATENT DOCUMENTS

| 4,607,167 | A | * | 8/1986 | Petric ..................... 250/492.2 |
| 4,726,689 | A | | 2/1988 | Pollock ....................... 384/12 |
| 4,912,052 | A | | 3/1990 | Miyoshi et al. ................ 437/8 |
| 5,001,349 | A | * | 3/1991 | van der Mast .......... 250/396 R |
| 5,359,197 | A | | 10/1994 | Komatsu et al. ............ 250/310 |
| 5,557,105 | A | * | 9/1996 | Honjo et al. ................ 250/310 |
| 5,628,828 | A | * | 5/1997 | Kawamura .................. 118/719 |
| 5,685,684 | A | * | 11/1997 | Kato et al. .................. 414/217 |
| 5,763,893 | A | * | 6/1998 | Nakasuji .................. 250/492.2 |
| 5,892,224 | A | | 4/1999 | Nakasuji ..................... 250/310 |
| 5,981,947 | A | | 11/1999 | Nakasuji et al. ............ 250/310 |
| 6,011,262 | A | * | 1/2000 | Hamashima et al. ........ 250/310 |
| 6,038,018 | A | * | 3/2000 | Yamazaki et al. ....... 356/237.1 |
| 6,087,667 | A | | 7/2000 | Nakasuji et al. .......... 250/492.2 |
| 6,125,522 | A | | 10/2000 | Nakasuji ...................... 29/458 |
| 6,259,960 | B1 | * | 7/2001 | Inokuchi ..................... 700/110 |
| 6,287,004 | B1 | * | 9/2001 | Sogard ........................ 384/12 |
| 6,518,582 | B1 | * | 2/2003 | Kohama ................... 250/492.2 |
| 6,539,106 | B1 | * | 3/2003 | Gallarda et al. ............ 382/149 |
| 6,566,658 | B1 | * | 5/2003 | Okubo ....................... 250/398 |
| 6,593,686 | B1 | * | 7/2003 | Yui ........................... 313/449 |
| 2001/0052577 | A1 | * | 12/2001 | Aki .......................... 250/492.2 |
| 2004/0222377 | A1 | * | 11/2004 | Shinada et al. ............. 250/310 |

FOREIGN PATENT DOCUMENTS

| JP | 08-022790 | 1/1996 |
| JP | 09-311112 | 12/1997 |
| JP | 10-134757 | 5/1998 |
| JP | HEI10-134757 | 5/1998 |
| JP | 2000-260376 | 9/2000 |

| | | |
|---|---|---|
| JP | 2000-285840 | 10/2000 |

OTHER PUBLICATIONS

English language translation of Office Action dated Sep. 13, 2005 from Japanese Patent Office in corresponding Japanese patent application No. 2002-542859.
Sandland et al; "An electron-beam inspection system for x-ray mask production", *J.of Vacuum Sci. & Tech. B* (1991) vol. 9, No. 6; pp. 3005-3009.
Meisburger et al; "Requirements and performance of an electron-beam column designed for x-ray mask inspection"; *J. of Vacuum Sci. & Tech. B;* (1991) vol. 9, No. 6; pp. 3010-3014.
Lischke et al; "Multi-beam Concepts for Nanometer Devices"; *JP J. Applied Physics* (1989) vol. 28, pp. 2058-2064.
*Electron/Ion Beam Handbook 2nd;* Nikkan Kogyo (1988) pp. 115-119 (with partial English translation).
U.S. Appl. No. 09/985,323, filed Nov. 2, 2001; Mamoru Nakasuji et al.; "Electron Beam Apparatus and Device Production Method Using the Electron Beam Apparatus".
U.S. Appl. No. 09/985,324, filed Nov. 2, 2001; Toshifumi Kimba et al.; "Apparatus for Inspecting Material with Electron Beam, Method for Operating Same, and Method for Manufacturing Semiconductor Device Using Former".
U.S. Appl. No. 09/985,325, filed Nov. 2, 2001; Mamoru Nakasuji et al.; "Electron Beam Apparatus and Method of Manufacturing Semiconductor Device Using the Apparatus".
U.S. Appl. No. 09/985,322, filed Nov. 2, 2001; Mamoru Nakasuji et al.; "Electron Beam Apparatus and Method of Manufacturing Semiconductor Device Using the Apparatus".
International Search Report Dated Jan. 15, 2002.

\* cited by examiner

*Primary Examiner*—Nikita Wells
*Assistant Examiner*—Phillip A. Johnston
(74) *Attorney, Agent, or Firm*—Westerman, Hattori, Daniels & Adrian, LLP

(57) ABSTRACT

The present invention relates to a substrate inspection apparatus for inspecting a pattern formed on a substrate by irradiating a charged particle beam onto the substrate. The substrate inspection apparatus comprises: an electron beam apparatus including a charged particle beam source for emitting a charged particle beam, a primary optical system for irradiating the charged particle beam onto the substrate, a secondary optical system into which a secondary charged particle beam is introduced, the secondary charged particle beam being emitted from the substrate by an irradiation of the charged particle beam, a detection system for detecting the secondary charged particle beam introduced into said secondary optical system and outputting as an electric signal, and a process control system for processing and evaluating the electric signal; a stage unit for holding the substrate and moving the substrate relatively to said electron beam apparatus; a working chamber capable of shielding at least an upper region of the stage unit form outside to control under desired atmosphere; and a substrate load-unload mechanism for transferring the substrate into or out of the stage.

9 Claims, 53 Drawing Sheets

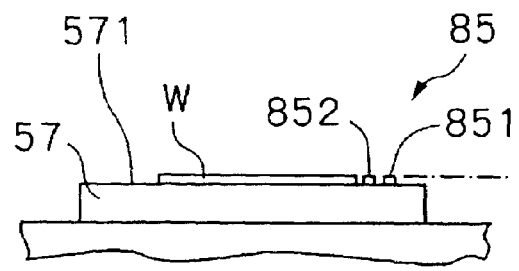
Fig. 16(A)
Fig. 16(B)
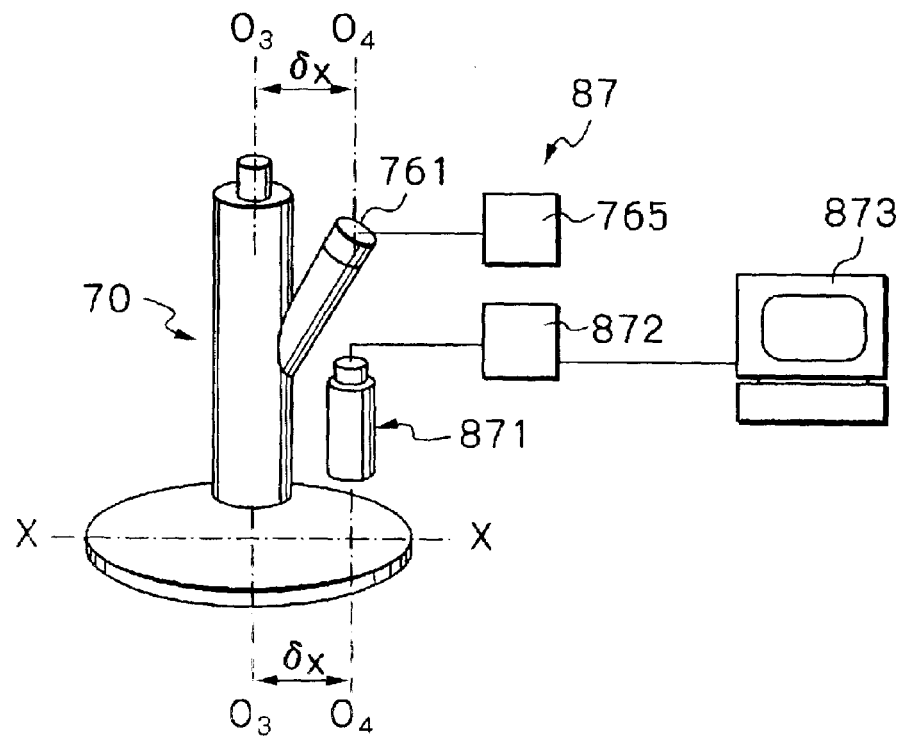
Fig. 17

METHOD FOR INSPECTING SUBSTRATE, SUBSTRATE INSPECTING SYSTEM AND ELECTRON BEAM APPARATUS

BACKGROUND OF THE INVENTION

In the field of semiconductor processes, the design rule is going into an age of 100 nm and the production form is on a transition from a mass production with a few models representative of a DRAM into a small-lot production with a variety of models such as a SOC (Silicon on chip). This results in an increase of a number of processes, and an improvement in an yield for each process must be essential, which makes more important an inspection for a defect possibly occurring in each process. The present invention relates to a substrate inspection method for inspecting a substrate such as a wafer after respective processes in the semiconductor process by using an electron beam, a substrate inspection apparatus to be used therefor and an electron beam apparatus for the inspection apparatus, and a device manufacturing method using the same method and apparatuses.

In conjunction with a high integration of semiconductor device and a micro-fabrication of pattern thereof, an inspection apparatus with higher resolution and throughput has been desired. In order to inspect a wafer substrate of 100 nm design rule for any defects, a resolution in size equal to or finer than 100 nm is required, and the increased number of processes resulting from a high integration of the device has called for an increase in the amount of inspection, which consequently requires higher throughput. In addition, as a multilayer fabrication of the device has been progressed, the apparatus has been further required to have a function for detecting a contact failure in a via for interconnecting a wiring between layers (i.e., an electrical defect). In the current trend, an inspection apparatus of optical method has been typically used, but it is expected that an inspection apparatus using an electron beam may soon be of mainstream, substituting for the inspection apparatus of optical method in the viewpoint of resolution and of inspection for contact malfunction. The inspection apparatus of electron beam method, however, has a weak point in that the inspection apparatus of electron beam method is inferior to the inspection apparatus of optical method in the throughput.

Accordingly, an apparatus having higher resolution and throughput and being capable of detecting the electrical defects has been desired to be developed. It has been known that the resolution in the inspection apparatus of optical method is limited to ½ of the wavelength of the light to be used, and it is about 0.2 µm for an exemplary case of a visible light having put to practical use.

On the other hand, in the method using an electron beam, typically a scanning electron beam method (SEM method) has been put to practice, wherein the resolution thereof is 0.1 µm and the inspection time is 8 hours per wafer (20 cm wafer). The electron beam method has a distinctive feature that it is able to inspect for any electrical defects (breaking of wire in the wirings, bad continuity, bad continuity of via). However, the inspection speed thereof is very low, and so the development of an inspection apparatus with higher inspection speed has been expected.

Generally, since an inspection apparatus is expensive and a throughput thereof is rather lower as compared to other processing apparatuses, therefore the inspection apparatus has been used after an important process, for example, after the process of etching, film deposition, CMP (Chemical-mechanical polishing) planarization or the like.

The inspection apparatus of scanning electron microscope (SEM) using an electron beam will now be described. In the inspection apparatus of SEM method, the electron beam is focused to be narrower (the diameter of this beam corresponds to the resolution thereof) and this narrowed beam is used to scan a sample so as to irradiate it linearly. On the other hand, moving a stage in the direction normal to the scanning direction allows an observation region to be irradiated by the electron beam as a plane area. The scanning width of the electron beam is typically some 100 µm. Secondary electrons emitted from the sample by the irradiation of said focused and narrowed electron beam (referred to as a primary electron beam) are detected by a detector (a scintillator plus PMT (i.e., photo multiplier tube) or a detector of semiconductor type (i.e., a PIN diode type) or the like). A coordinate for an irradiated location and an amount of the secondary electrons (signal intensity) are combined and formed into an image, which is stored in a storage or displayed on a CRT (a cathode ray tube). The above description shows the principle of the SEM (scanning electron microscope), and defects in a semiconductor wafer (typically made of Si) in the course of processes may be detected from the image obtained in this method. The inspection speed (corresponding to the throughput) is varied in dependence on an amount of primary electron beam (the current value), a beam diameter, and a speed of response of the detecting system. The beam diameter of 0.1 µm (which may be considered to be equivalent to the resolution), the current value of 100 nA, and the speed of response of the detector of 100 MHz are the currently highest values, and in the case using those values the inspection speed has been evaluated to be about 8 hours for one wafer having the diameter of 20 cm. This inspection rate, which is extremely lower as compared with the case using light (not greater than 1/20), has been a big problem (drawback).

On the other hand, as a method for improving the inspection speed or a drawback of the SEM method, new SEM (multi beam SEM) method using a plurality of electron beams and an apparatus therefor have been disclosed. In this method, though the inspection rate can be improved by a number of the plurality of electron beams, there are other problems that since a plurality of primary electron beam is irradiated from an oblique direction and a plurality of secondary electron beam is taken out along an oblique direction from a sample, the detector receives the secondary electrons emitted from the sample only along the oblique direction, that a shadow emerges on an image, and further that secondary electron signals are mixed together because it is difficult to separate respective secondary electrons coming from the plurality of electron beams respectively.

Conventionally, there has been known an evaluation apparatus in which a primary electron beam emitted from an electron gun is focused to be narrower by a lens system to be irradiated onto a surface of the sample, and then secondary electrons emitted from the sample are detected to evaluate the sample surface such as a line width measurement, inspection for the defects thereon or the like. In this kind of evaluation apparatus, the S/N ratio is required to be higher than a predetermined value (for example, 22 to 70). In the case where thermal field emission electron gun is used, it is required to detect the secondary electrons in a range of 1,000 to 10,000 for each pixel.

For example, assuming a detection efficiency being 10%, $10^4$ to $10^5$ pieces of primary electrons have to be irradiated for each pixel. When converting this value into dose, dose D (Q/cm$^2$) may be represented, assuming the pixel size being 0.1 µm square, as:

$$D=10^4 \times 1.6 \times 10^{-19} Q/(0.1 \times 10^{-4})^2 \sim 10^5 \times 1.6 \times 10^{-19} Q/(0.1 \times 10^{-4})^2 = 16 \ \mu c/c \ m^2 \sim 160 \ \mu c/c \ m^2$$

Such dose value as in the range of 16 µc/c m$^2$ to 160 µc/c m$^2$ is a significantly large value for the wafer containing a layer of almost completely finished transistor, and such a dose value may have a negative effect thereon that, for example, a threshold voltage Vth of the transistor may increase.

That is, the conventional evaluation apparatus of semiconductor wafer has to employ large S/N ratio and thus large dose, which means when the dose is increased to irradiate large amount of primary electron beam, the threshold voltage of the transistor on the wafer is increased, eventually resulting in a characteristic of the semiconductor device being damaged during the evaluation of a wafer.

Further, in the prior art, there has been another problem that there may occur a location offset between an image of secondary electron beam obtained by irradiating the primary electron beam onto the sample surface and a reference image prepared beforehand, resulting in a deterioration of accuracy in detecting the defect. This location offset may cause a considerably serious problem when an irradiation area of the primary electron beam has an offset with respect to the wafer, and thereby a part of an inspection pattern drops out of the detecting image of the secondary electron beam, which cannot be dealt with only by a technology for optimizing a matching area within the detecting image. This must be a fatal drawback especially in the inspection for a fine micro pattern.

SUMMARY OF THE INVENTION

An object of the present invention is to provide a substrate inspection method capable of inspecting and evaluating a sample with high throughput and high reliability, and a substrate inspection apparatus therefor and an electron beam apparatus for the inspection apparatus.

Another object of the present invention is to provide a substrate inspection method capable of employing a desired level of S/N ratio of a detection signal of a secondary electron even if a dose of a primary charged particle beam being decreased, and a substrate inspection apparatus therefor and an electron beam apparatus for the inspection apparatus.

Still another object of the present invention is to provide a substrate inspection method capable of inspecting for any defects with small amount of information and of selecting either way of evaluating a large size of wafer and the like with high throughput or with high accuracy, and a substrate inspection apparatus therefor and an electron beam apparatus for the inspection apparatus.

Still another object of the present invention is to provide a substrate inspection method in which a plurality of charged particle beams may be irradiated at once, and either one of an evaluation with improved measuring accuracy and an evaluation with improved throughput may be selected because of being equipped with a storage section storing a lens condition or an axial alignment condition of a primary optical system and a secondary optical system corresponding to a pixel size for scanning the sample, and also to provide a substrate inspection apparatus therefor and an electron beam apparatus for the inspection apparatus.

Still another object of the present invention is to provide a substrate inspection method in which independent of an adjustment of the lens condition of the primary optical system, a focusing condition and a magnifying ratio of the secondary optical system may be adjusted so that a divergence of these values from the design values may be compensated for so as to accomplish highly reliable inspection and evaluation, and also to provide a substrate inspection apparatus therefor and an electron beam apparatus for the inspection apparatus.

Still another object of the present invention is to provide a substrate inspection apparatus in which an angular aperture may be adjusted independently between the primary and the secondary optical systems to minimize a number of optical components which cannot be axially aligned and the lens condition may be adjusted in both optical systems, and also to provide an electron beam apparatus for the inspection apparatus.

Still another object of the present invention is to provide a substrate inspection method in which in a pattern forming surface of the sample, an area with many defects expected to occur therein and an area with wide variation of evaluation values expected therein are selected so as to irradiate the electron beam or the light thereon to evaluate such areas with priority, thereby promoting a quick evaluation, and also to provide a substrate inspection apparatus therefor and an electron beam apparatus for the inspection apparatus.

Still another object of the present invention is to provide a substrate inspection apparatus comprising at least one of a laser reflector mirror having a stiffness as high as possible without any necessity for using a thick base body and another laser reflector mirror capable of removing recesses on a mirror surface possibly caused by voids and at the same time retaining a highly accurate flatness of the mirror surface, and also to provide an electron beam apparatus for the inspection apparatus.

Still another object of the present invention is to provide a substrate inspection method in which a killer defect can be discriminated from a non-killer defect even if a minimum line width being 0.1 µm or less, and in addition, an inspection time can be reduced as compared with the case of the defect inspection apparatus using the SEM, and also to provide a substrate inspection apparatus therefor and an electron beam apparatus for the inspection apparatus.

Still another object of the present invention is to provide a substrate inspection method in which an accurate measuring equipment such as a laser interferometer is installed in a stage position and thereby a precise inspection may be accomplished even in the case where a measurement is performed under unstable temperature condition or a relative vibration exists between an optical system of an electron beam apparatus and a sample chamber or a stage, and also to provide a substrate inspection apparatus therefor and an electron beam apparatus for the inspection apparatus.

Still another object of the present invention is to provide a substrate inspection method in which a single inspection apparatus has a plurality of functions so that the inspection and the evaluation of the sample may be performed with small number of apparatuses, thereby reducing a ratio of a foot print occupied by the inspection apparatuses in a clean room of a semiconductor manufacturing equipment, and also to provide a substrate inspection apparatus therefor and an electron beam apparatus for the inspection apparatus.

Still another object of the present invention is to provide a substrate inspection apparatus which is provided with a non-contact supporting mechanism by means of a hydrostatic bearing and a vacuum sealing mechanism by means of differential pumping so that a pressure difference may be generated between a charged particle beam irradiating region and a hydrostatic bearing support section and a gas desorbed from a surface of component facing to the hydrostatic bearing may be reduced, and also to provide an electron beam apparatus for the inspection apparatus.

Still another object of the present invention is to provide a semiconductor device manufacturing method in which such a substrate inspection method, a substrate inspection apparatus and a charged particle beam apparatus for the inspection apparatus as described above are used in the semiconductor device manufacturing process to perform a defect inspection and an evaluation of the sample, thereby improving a yield of device product and preventing any defective products from being delivered.

It is to be noted that in the present application, a term "inspection" is used to mean not only a detection of malfunction state such as defect but also an evaluation of a detected result.

A substrate inspection method according to a first invention of the present application comprises the steps of:

(1) emitting a primary charged particle beam from a charged particle beam source;

(2) irradiating said generated primary charged particle beam onto a substrate through a primary optical system;

(3) introducing a secondary charged particle beam into a secondary optical system, said secondary charged particle beam being emitted from said substrate by said irradiation of said primary charged particle beam;

(4) detecting said secondary charged particle beam having been introduced into said secondary optical system and converting said detected secondary charged particle beam into an electric signal; and (5) processing said electric signal to evaluate said substrate.

In an embodiment of said substrate inspection method, said charged particle beam source may be actuated in a space charge limited region, so that the primary charged particle beam emitted from said charged particle beam source may be irradiated onto a multi aperture plate having a plurality of apertures of said primary optical system, and thereby the plurality of charged particle beams having passed through said plurality of apertures may be formed into an image on the substrate surface. Further, said charged particle beam source may be actuated in the space charge limited region, and said charged particle beam source may emit said primary charged particle beam from a plurality of electron emission region on a circle corresponding to said plurality of apertures of the multi aperture plate of the primary optical system.

Further, in another embodiment of said substrate inspection method, said substrate inspection method may further comprise a step (6) in which said detection system detects the secondary charged particle beam emitted from a plurality of regions on said substrate to obtain a plurality of sub-image data, and a step (7) for re-arranging said detected plurality of sub-image data to generate an image data of the inspection region on the substrate, and may further comprise a step (8) for storing in advance a reference image data with respect to the substrate to be evaluated, and a step (9) for evaluating the substrate by comparing said image data generated by an image processor with said stored reference image data.

Further, in still another embodiment of said substrate inspection method, said substrate may be controlled so as to continuously move in the Y-axis direction; respective charged particle beam are driven to simultaneously scan in the X-axis direction such that irradiation spots of a plurality of primary charged particle beams on the substrate are arranged with equal spacing therebetween in the X-axis direction and respective scanning regions may partially be superimposed with each other in the X-axis direction; and while comparing the sub-image data, the X and the Y coordinates of respective charged particle beams are taken into account thereby inspecting the surface of the substrate. Further, in said substrate inspection method, a lens condition or an axial alignment condition of said primary and said secondary optical systems corresponding to the pixel size for scanning and irradiating said substrate may be stored.

Further, in still another embodiment of said substrate inspection method, said substrate inspection method may further comprise the steps of converting said electric signal into a pattern information and comparing said pattern information with a reference pattern, wherein a minimum value of distance between respective charged particle beams in said plurality of charged particle beams may be controlled to be larger than a value of resolution of said secondary optical system converted into a value on the surface of said substrate.

Further, still another embodiment of said substrate inspection method may further comprise the steps of converting said electric signal received from said detection section into a binary information, converting said binary information into a rectangular pattern information, and comparing said rectangular pattern information with the reference pattern.

In still another embodiment of the substrate inspection method according to said first invention, for generating an image of the substrate and evaluating a pattern formed on said substrate based on said image, said method may further comprise the steps of: storing a reference image corresponding to said image of the substrate; reading out said stored reference image; comparing said image of the substrate with said read-out reference image and detecting different portions between both images; and classifying said different portions into such defects including at least short-circuit, disconnection, convex, chipping, pinhole and isolation; wherein for generating said image of the substrate, said method may further comprise the steps of: scanning the substrate surface by a plurality of beams each focused to be narrower by the primary optical system; converging the secondary charged particle beam from the substrate by an objective lens and further separating said converged secondary charged particle beam from the primary optical system by an E×B separator; magnifying an angle formed between an orbit of the secondary charged particle beam from said substrate and an optical axis by the secondary optical system by using a single stage lens so as to be focused on a multi apertures for detection; and detecting said focused secondary charged particle beam by a plurality of detectors.

Further, in still another embodiment of said substrate inspection method, in a pattern forming surface of said substrate, an area with many defects being expected to occur therein and an area with wide variation of evaluation values being expected therein may be selected; and the charged particle beam may be irradiated onto these areas to evaluate such areas with priority; wherein: in an evaluation of the pattern forming surface whose whole pattern is formed by dividing said pattern forming surface into a plurality of areas and forming respective pattern for each area, said evaluation may be executed by selecting a boundary area between said divided areas; or in an evaluation of the pattern forming surface which is formed by dividing the pattern forming surface into a plurality of adjacent stripes and forming a pattern for each stripe by a lithography, said evaluation may be executed by selecting a boundary area between the stripes, a boundary area between primary fields of view or a boundary area between secondary fields of view of a pattern projection in the lithography.

Further, in still another embodiment of said substrate inspection method, the charged particle beam may be irradiated onto said pattern forming surface of the substrate, and said pattern may be evaluated based on said secondary charged particle beam, wherein, in the pattern forming surface, an area with many defects being expected to occur therein and an area with wide variation of evaluation values being expected therein may be selected, and a central portion of the field of view of the apparatus used for the present inspection may be located to be superimposed on the selected areas.

In still another embodiment of the substrate inspection method according to said first invention, said method may further comprise the steps of: detecting an abnormal pattern from the image data generated by processing said electric signal; and determining whether or not said detected abnormal pattern is a killer defect based on a relation thereof with the predetermined reference pattern; wherein said image processing section may process a plurality of image data corresponding to said plurality of secondary charged particle beams simultaneously or in parallel.

Further, in still another embodiment of said substrate inspection method, at least two functions selected from the group consisting of a defect detection of the substrate surface, a defect review of the substrate surface, a pattern line width measurement, and a pattern potential measurement may be performed, wherein said defect detection of the substrate surface may be performed by comparing the image obtained by the image signal with the pattern data or by comparing the different dice with each other; said defect review of the substrate surface may be performed by observing the image obtained by a scanning of the beam on the monitor synchronized with a scanning of the primary charged particle beam on the substrate surface; said pattern line width measurement may be performed by using a line profile image of the secondary charged particle beam obtained when the primary charged particle beam scan the substrate surface in a short side direction of the pattern; and said pattern potential measurement may be performed by applying a negative potential to an electrode disposed in the nearest location to the substrate surface and thereby selectively driving back the secondary charged particle beam emitted from the pattern on the substrate surface having a high potential.

Still another embodiment of said substrate inspection method may further comprise a step of setting an evaluation condition such that a processed condition of each substrate should be evaluated within a processing time necessary for processing one substrate by a processing unit, or such that the processed condition of one lot of substrates should be evaluated within the processing time necessary for processing one lot of substrates by the processing unit, wherein said step may further comprise a step of setting an evaluation area of the substrate such that the processed condition should be evaluated only in a specified area.

In still another embodiment of said substrate inspection method according to the first invention, said inspection method may further comprise the steps of: obtaining respective images of a plurality of regions to be inspected each displaced from others while partially superimposing with each other on said substrate; storing a reference image; and comparing said obtained images of the plurality of regions to be inspected with said stored reference image and thereby determining a defect on said substrate.

In still another embodiment of said substrate inspection method, said inspection method may further comprise the steps of: performing an irradiation of the primary charged particle beam onto said substrate within a working chamber controlled to be a desired atmosphere; performing a transfer of said substrate into and out of said working chamber through a space within a vacuum chamber; applying a potential to said substrate within said working chamber; and observing the surface of said substrate and aligning said substrate to an irradiation location of said primary charged particle beam.

A second invention according to the present application provides an electron beam apparatus in which a primary charged particle beam is irradiated onto a substrate to emit a secondary charged particle beam and said secondary charged particle beam is detected to evaluate the substrate, said apparatus comprising:

a charged particle beam source for generating the primary charged particle beam;

a primary optical system for irradiating a plurality of said primary charged particle beams onto said substrate while scanning them relative to said substrate;

a secondary optical system into which the secondary charged particle beams emitted from said substrate by the irradiation of said primary charged particle beams are introduced;

a detection system for detecting the secondary charged particle beams introduced into said secondary optical system and converting the detected secondary charged particle beams into an electric signals; and a process control system for evaluating the substrate based on said electric signal.

A third invention according to the present application provides an electron beam apparatus in which a primary charged particle beam is irradiated onto a substrate to emit a secondary charged particle beam and said secondary charged particle beam is detected to evaluate the substrate, said apparatus comprising:

a charged particle beam source for emitting the primary charged particle beam;

a primary optical system for irradiating a single beam of said primary charged particle beam onto said substrate while scanning it relative to said substrate;

a secondary optical system into which the secondary charged particle beam emitted from said substrate by the irradiation of said primary charged particle beam is introduced;

a detection system for detecting the secondary charged particle beam introduced into said secondary optical system and converting the detected secondary charged particle beam into an electric signal; and a process control system for evaluating the substrate based on said electric signal.

In an embodiment of the electron beam apparatus according to the second invention, said charged particle beam source may be set to actuate within a space charge limited region; a cathode of said charged particle beam source may be made of monocrystal $LaB_6$; and the charged particle beam emitted from the charged particle beam source may be irradiated onto a multi aperture plate having a plurality of apertures of said primary optical system, and the plurality of charged particle beams having passed through said plurality of apertures may be formed into an image on a surface of said substrate; or alternatively said charged particle beam source may be set to actuate within the space charge limited region; said primary optical system may comprise a multi aperture plate having a plurality of apertures arranged on a circle; and a plurality of cathode of the charged particle beam source, each made of $LaB_6$, may be arranged on a circle so that each electron emission region thereof may correspond to each of said plurality of apertures of said multi aperture plate respectively.

Further, in an embodiment of the electron beam apparatus according to the second invention, said detection system may detect the secondary charged particle beam emitted from a plurality of regions of said substrate to obtain a plurality of sub-image data, and said electron beam apparatus may further comprise an image processor for re-arranging said detected plurality of sub-image data to generate an image data of the inspection region on the substrate, wherein, said electron beam apparatus may further comprise a memory for storing in advance a reference image data with respect to the substrate to be evaluated, and an evaluator for evaluating the substrate by comparing said image data generated by said image processor with said reference image data stored in said memory. In said case, said substrate may be controlled so as to continuously move in the Y-axis direction; said primary optical system may be configured such that respective charged particle beams are driven to simultaneously scan in the X-axis direction so that irradiation spots of a plurality of charged particle beams on the substrate are arranged with approximately equal spacing therebetween in the X-axis direction, and respective scanning regions may partially be superimposed with each other in the X-direction; and said image processor is configured such that while said sub-image data being re-arranged, the X and the Y coordinates of respective charged particle beams should be taken into account to generate the image data of the substrate surface.

Further, in another embodiment of the electron beam apparatus according to the second invention, said apparatus may further comprise a storage section for storing a lens condition or an axial alignment condition of said primary and said secondary optical systems corresponding to a pixel size with which said primary charged particle beams are irradiated onto said substrate while scanning them relative to said substrate.

Further, in an embodiment of the electron beam apparatus according to the third invention, said apparatus may further comprise a storage section for storing a lens condition or an axial alignment condition of said primary and said secondary optical systems corresponding to a pixel size with which said primary charged particle beams are irradiated onto said substrate while scanning it relative to said substrate.

Further, in another embodiment of the electron beam apparatus according to the third invention, said apparatus comprises, said electronic optical system may further comprise: at least one stage of axially symmetric lens comprising an electrode made by processing an insulating material and applying a metal coating onto a surface thereof; a plurality combinations of said charged particle beam source, said primary optical system and said secondary optical system, each of said combinations comprising an optical column; and a storage section for storing a lens condition or an axial alignment condition of said primary and said secondary optical systems corresponding to a pixel size used for scanning said substrate.

Further, in another embodiment of the electron beam apparatus according to the second invention, in said apparatus, said process control system may comprise a secondary charged particle beam processing section, wherein said secondary charged particle beam processing section comprises a converter for converting said electric signal into a pattern information, and a comparator for comparing said pattern information with the reference pattern, wherein a minimum value of distance between respective charged particle beams in said plurality of charged particle beams may be controlled to be larger than a value of resolution of said secondary optical system converted into a value on the surface of said substrate.

Further, in another embodiment of the electron beam apparatus according to the second and the third inventions, in said apparatus, said process control system may comprise said image processing section, wherein said image processing section may comprise a converter for converting said electric signal received from said detection section into a binary information, a converter for converting said binary information into a rectangular pattern information, and a comparator for comparing said rectangular pattern information with the reference pattern. In this case, said primary and said secondary optical systems may be accommodated in an optical column, wherein said primary optical system may comprise, in said optical column, at least one axially symmetric lens made of insulating material with an electrode formed on a surface thereof by metal coating.

Further, in another embodiment of the electron beam apparatus according to the second invention, generating an image of the substrate and evaluating a pattern formed on said substrate based on said image may be performed by: storing a reference image corresponding to said image of the substrate; reading out said stored reference image; comparing said image of the substrate with said read-out reference image and detecting different portions between both images; and classifying said different portions into such defects including at least short-circuit, disconnection, convex, chipping, pinhole and isolation; wherein said generating the image of the substrate is performed by: scanning the substrate surface by a plurality of beams each focused to be narrower by the primary optical system; converging the secondary charged particle beam from the substrate by an objective lens and further separating said converged secondary charged particle beam from the primary optical system by an EXB separator; focusing a secondary charged particle beam image from said substrate on a multi aperture for detection with an angle formed between a secondary electron orbit and an optical axis being magnified, by said secondary optical system using at least one stage of lens; and detecting said focused secondary charged particle beam by a plurality of detectors; wherein said electron beam apparatus may further comprise (1) a function for pre-aligning said substrate, (2) a function for registering in advance a recipe for performing an inspection of said substrate, (3) a function for reading out a substrate number formed on said substrate, (4) a function for reading out a recipe corresponding to said substrate by using said read-out substrate number, (5) a function for performing an inspection based on said read-out recipe, (6) a function for registering in advance an inspection pattern image for said substrate, (7) a function for reading out and displaying said registered inspection pattern image, (8) a function for moving said substrate based on a specification on said inspection pattern image or a direction of said recipe so that said specified or directed inspection point may approach a desired location, (9) a function for registering in advance a reference image for said specified or directed inspection point, (10) a function for forming said reference image for said specified or directed inspection point and positioning said inspection point by comparing an image for positioning said specified or directed inspection point with a reference image for positioning said inspection point, (11) a function for forming an image for inspecting said positioned inspection point, (12) a function for storing said reference image for inspecting said positioned inspection point, (13) a function for displaying said image for inspection and said reference image for inspection, (14) a function for comparing said both images to detect different portions therebetween, (15) a function for classifying said different portions into such defects including at least short-circuit, disconnection, convex, chipping, pinhole and isolation, (16) a function for classifying the size of said respective defects including at least short-circuit, disconnection, convex, chipping, pinhole and isolation, (17) a function for irradiating a probe onto said different portions on said substrate so as to physically analyze, (18) a function for overwriting said inspection pattern image with a classification result of the different portions of said specified or directed inspection point, (19) a function for calculating a defect density of all defects as well as respective defects classified by type or size for respective chips, substrates and a specified substrate when said substrate is a substrate, (20) a function for registering in advance a defect size-critical rate table for said respective defect types, (21) a function for calculating a yield for respective chips, substrates and a specified substrate based on said defect size-critical rate table for said respective defect types, (22) a function for registering a different portion detection result of said specified inspection point, a classification result of said different portions, and a calculation result of said respective defect densities and yields, and (23) a function for outputting said registered respective inspection results and calculation results.

Further, in another embodiment of the electron beam apparatus according to the second invention, said primary optical system may comprise a aperture plate for forming said primary charged particle beam into a plurality of beams, and an E×B separator, wherein an aperture determining an angular aperture for said primary optical system may be disposed between said aperture plate and said E×B separator, or alternatively, said primary optical system may further comprise a condenser lens for focusing said primary charged particle beam emitted from said charged particle beam source to form a crossover image, and the apertures for forming said primary charged particle beam into a plurality of beams, wherein said apertures may be disposed between said condenser lens and said crossover image, and an numerical aperture for said primary optical system may be adjusted by changing a magnifying ratio of said crossover image or adjusted to a design value, or alternatively, said primary optical system may further comprise a condenser lens for focusing said primary charged particle beam emitted from said charged particle beam source to form a first crossover image, and a aperture plate for forming said primary charged particle beam into a plurality of beams, wherein said aperture plate may be disposed between said condenser lens and said first crossover image, and said secondary optical system may further comprise a condenser lens for focusing said plurality of secondary charged particle beam to form a second crossover image.

In another embodiment of the electron beam apparatus according to said first and said second inventions, in a pattern forming surface of said substrate, an area with many defects being expected to occur therein and an area with wide variation of evaluation values being expected therein may be selected, and the charged particle beam may be irradiated onto these areas to evaluate such areas with priority, and in this case, in an evaluation of the pattern forming surface whose whole pattern is formed by dividing said pattern forming surface into a plurality of areas and forming respective pattern for each area, said evaluation may be executed by selecting a boundary area between said divided areas, or alternatively, in an evaluation of the pattern forming surface which is formed by dividing said pattern forming surface into a plurality of adjacent stripes and forming a pattern for each stripe by a lithography, said evaluation may be executed by selecting a boundary area between the stripes, a boundary area between primary fields of view of a pattern projection in the lithography or a boundary area between sub-fields of view.

In another embodiment of the electron beam apparatus according to said second and said third inventions, the charged particle beam is irradiated onto a pattern forming surface of said substrate, and said pattern is evaluated based on said secondary charged particle beam, wherein, in said pattern forming surface, an area with many defects being expected to occur therein and an area with wide variation of evaluation values being expected therein may be selected, and a central portion of the field of view of the apparatus may be positioned to be superimposed on said selected areas, or alternatively, said process control unit may comprise a secondary charged particle beam signal processing section, a detector for detecting an abnormal pattern from an image data generated in said secondary charged particle beam processing section and a determining system for determining whether or not said detected abnormal pattern is a killer defect based on a relation thereof with a predetermined reference pattern.

In another embodiment of the electron beam apparatus according to said first and said second inventions, said apparatus may further comprise at least two functions selected from the group consisting of a defect detection of a substrate surface, a defect review of the substrate surface, a pattern line width measurement, and a pattern potential measurement. In the electron beam apparatus of this embodiment, said defect detection of the substrate surface may be performed by comparing an image obtained by an image signal with a pattern data or by comparing different dice with each other, said defect review of the substrate surface may be performed by observing an image obtained by a scanning of the beam on a monitor synchronized with a scanning of the primary charged particle beam on the substrate surface, said pattern line width measurement may be performed by using a line profile image of the secondary charged particle beam obtained when the primary charged particle beam scans the substrate surface in a short side direction of the pattern, and said pattern potential measurement may be performed by applying a negative potential to an electrode disposed in the nearest location to the substrate surface and thereby selectively driving back the secondary charged particle beam emitted from the pattern on the substrate surface having a high potential.

In another embodiment of the electron beam apparatus according to said second and said third inventions, said apparatus may further comprise an evaluation condition setter for setting an evaluation condition such that a processed condition of each substrate should be evaluated within a processing time necessary for processing one substrate by a processing unit, or alternatively, said apparatus may further comprise an evaluation condition setter for setting an evaluation condition such that a processed condition of one lot of substrates should be evaluated within a processing time necessary for processing one lot of substrates by a processing unit. In this case, said evaluation condition setter may comprise a setter for setting an evaluation area of the substrate such that the processed condition should be evaluated only in a specified area on a substrate surface.

In another embodiment of the electron beam apparatus according to said second and said third inventions, said process control unit may comprise an image obtaining device for obtaining respective images of a plurality of regions to be inspected each displaced from others while partially superimposing with each other on said substrate, a memory for storing a reference image, and a defect determining system for comparing said images of the plurality of regions to be inspected obtained by said image obtaining device with said reference image stored in said memory and thereby determining a defect on said substrate.

Further, in another embodiment of the electron beam apparatus according to said second and said third inventions, a plurality of optical systems each including said charged particle beam source, said primary optical system, said secondary optical system and said detection system may be arranged on one substrate to be inspected.

Further, in another embodiment of the electron beam apparatus according to said second and said third inventions, said primary optical system may comprise an objective lens, wherein an electrostatic lens, which configures said objective lens, may have an inner section made of ceramic material having a low linear expansion coefficient which is integrally configured with another ceramic material disposed outside thereof, and a plurality of electrodes may be formed on a surface of the ceramic material of said inner section by metal coating, wherein each of said plurality of electrodes may be arranged respectively to be axially symmetric.

Further, in another embodiment of the electron beam apparatus according to said second and said third inventions, said primary optical system may comprise an objective lens, wherein an electrostatic lens, which configures said objective lens, may have an inner section made of ceramic material capable of being machined, which is adhesively fixed to another ceramic material disposed outside thereof; and a plurality of electrodes may be formed on a surface of the ceramic material of said inner section by metal coating, wherein each of said plurality of electrodes may be arranged respectively to be axially symmetric.

A fourth invention according to the present application provides a substrate inspection apparatus for inspecting a pattern formed on a substrate by irradiating a charged particle beam onto said substrate, said apparatus comprising:

an electron beam apparatus comprising: a charged particle beam source for emitting a charged particle beam; a primary optical system for irradiating said charged particle beam onto said substrate; a secondary optical system into which a secondary charged particle beam is introduced, said secondary charged particle beam being emitted from said substrate by an irradiation of said charged particle beam; a detection system for detecting said secondary charged particle beam introduced into said secondary optical system and outputting as an electric signal; and a process control system for processing and evaluating said electric signal;

a stage unit for holding said substrate and moving said substrate relatively to said electron beam apparatus;

a working chamber capable of shielding at least an upper region of said stage unit form outside to control under desired atmosphere; and a substrate transfer mechanism for transferring said substrate into or out of said stage.

In an embodiment of the substrate inspection apparatus according to said fourth invention, said apparatus may further comprise a laser interferometer for detecting a location of said stage unit, wherein, said primary optical system may comprise an objective lens which is configured by an axially symmetric electrostatic lens at least whose outer section is made of ceramic material having a low linear expansion coefficient, and a reference mirror of said laser interferometer may be mounted on said outer section of said electrostatic lens.

In another embodiment of said substrate inspection apparatus, said apparatus may further comprise a laser interferometer which includes a laser reflection mirror mounted at least on said stage unit or formed by polishing a part of member of said stage unit and is used for measuring a location of said stage by reflecting a laser with said laser reflection mirror, wherein said laser reflection mirror may be formed by a base body made of SiC ceramic.

In another embodiment of the substrate inspection apparatus according to said fourth invention, a plurality of optical columns each including said charged particle beam source, said primary optical system, said secondary optical system and said detection system may be arranged therein in parallel; and a laser interferometer which includes a laser reflection mirror mounted at least on said stage unit or formed by polishing a part of member of said stage unit and is used for measuring a location of said stage by reflecting a laser with said laser reflection mirror may, wherein said laser reflection mirror may be formed by a base body made of SiC ceramic, and each of said plurality of optical columns may comprise at least one stage of axially symmetric lens with an outer diameter processed to be small size by machining a ceramic and selectively applying a metal coating on a surface thereof.

In another embodiment of said substrate inspection apparatus, said stage unit may be provided with a non-contact supporting mechanism by means of a hydrostatic bearing and a vacuum sealing mechanism by means of differential pumping, a divider may be provided for making a conductance smaller between a region on a surface of said substrate where said primary charged particle beam is to be irradiated and a hydrostatic bearing support section of said stage unit, so that a pressure difference may be generated between said charged particle beam irradiating region and said hydrostatic bearing support section.

In another embodiment of said substrate inspection apparatus, a table of said stage unit may be accommodated in a housing and supported in a non-contact manner by a hydrostatic bearing, said housing accommodating said stage may be vacuumed, and a differential pumping mechanism for evacuating a region on a surface of said substrate where said primary charged particle beam is to be irradiated may be provided so as to surround a portion of said electron beam apparatus where said primary charged particle beam is to be irradiated onto said substrate surface.

Further in another embodiment of said substrate inspection apparatus, said apparatus may further comprise a vibration isolation unit for isolating a vibration from a floor to said vacuum chamber.

Further, in another embodiment of said substrate inspection apparatus, said apparatus may further comprise a potential applying mechanism disposed in said working chamber for applying a potential to said object to be inspected, and an alignment control unit for observing a surface of said object to be inspected and controlling an alignment thereof in order to position said object to be inspected with respect to said electron optical system.

Further, in another embodiment of said substrate inspection apparatus, said electron beam apparatus may be any electron beam apparatus defined in either of claim 24 to 55.

A fifth invention according to the present application provides a semiconductor device manufacturing method comprising a step of evaluating a semiconductor substrate in a course of processes or after having been completed by using either of the substrate inspection method, the electron beam apparatus or the substrate inspection apparatus, described above.

BRIEF DESCRIPTION OF THE DRAWINGS

FIG. 16 illustrates an electron beam calibration mechanism, wherein (A) is a side elevational view and (B) is a plan view;

FIG. 17 is a schematic diagram of an alignment control device for a wafer;

DETAILED DESCRIPTION OF THE INVENTION

There will now be described preferred embodiments of the present invention as a substrate inspection apparatus for inspecting a substrate or a wafer as an object to be inspected having a pattern formed on a surface thereof, with reference to the attached drawings.

Figure 1:
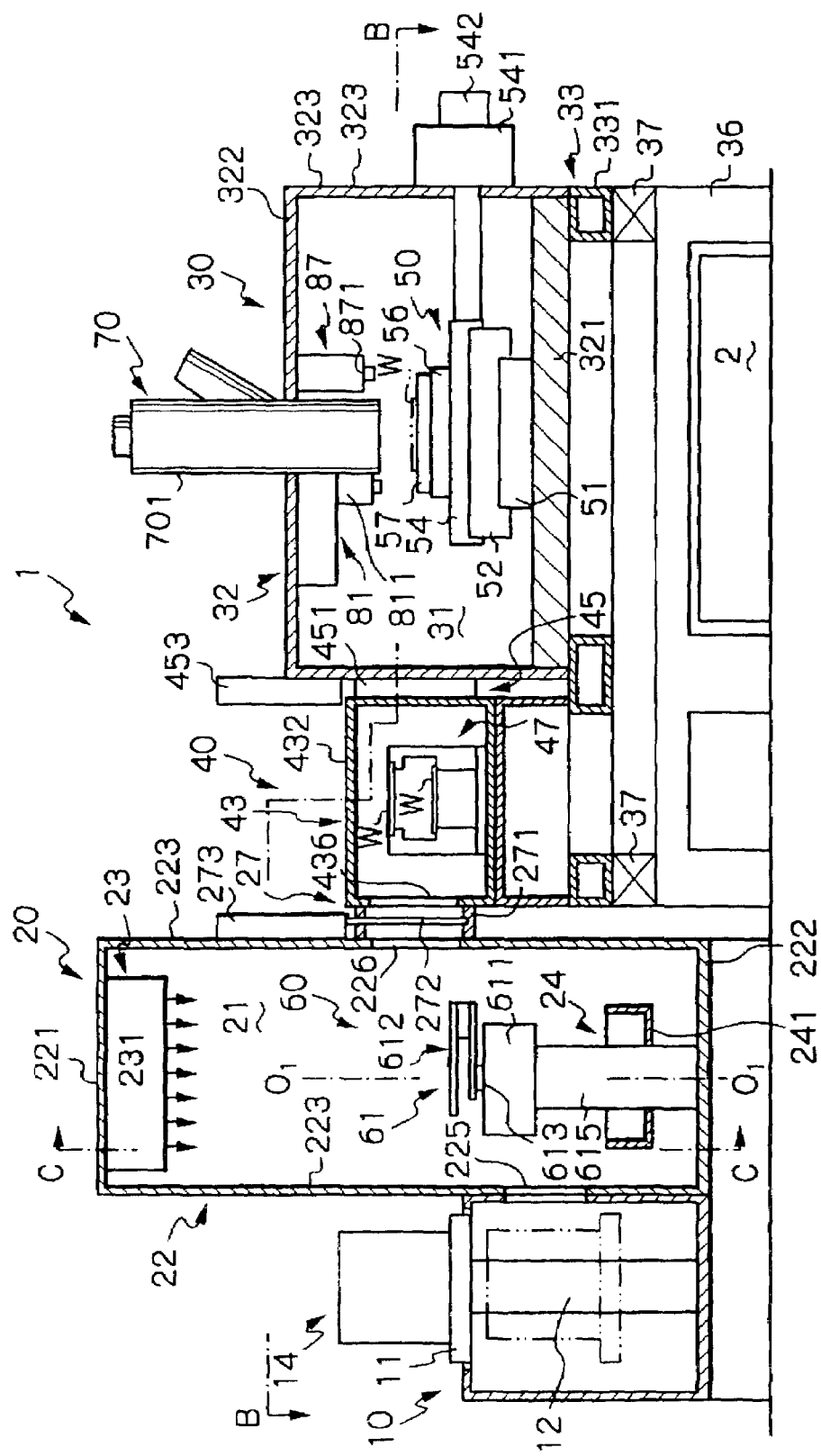
FIG. 1 is a cross-sectional elevational view taken along a line A—A of FIG. 2, illustrating main components of an inspection apparatus according to the present invention.
Figure 2:
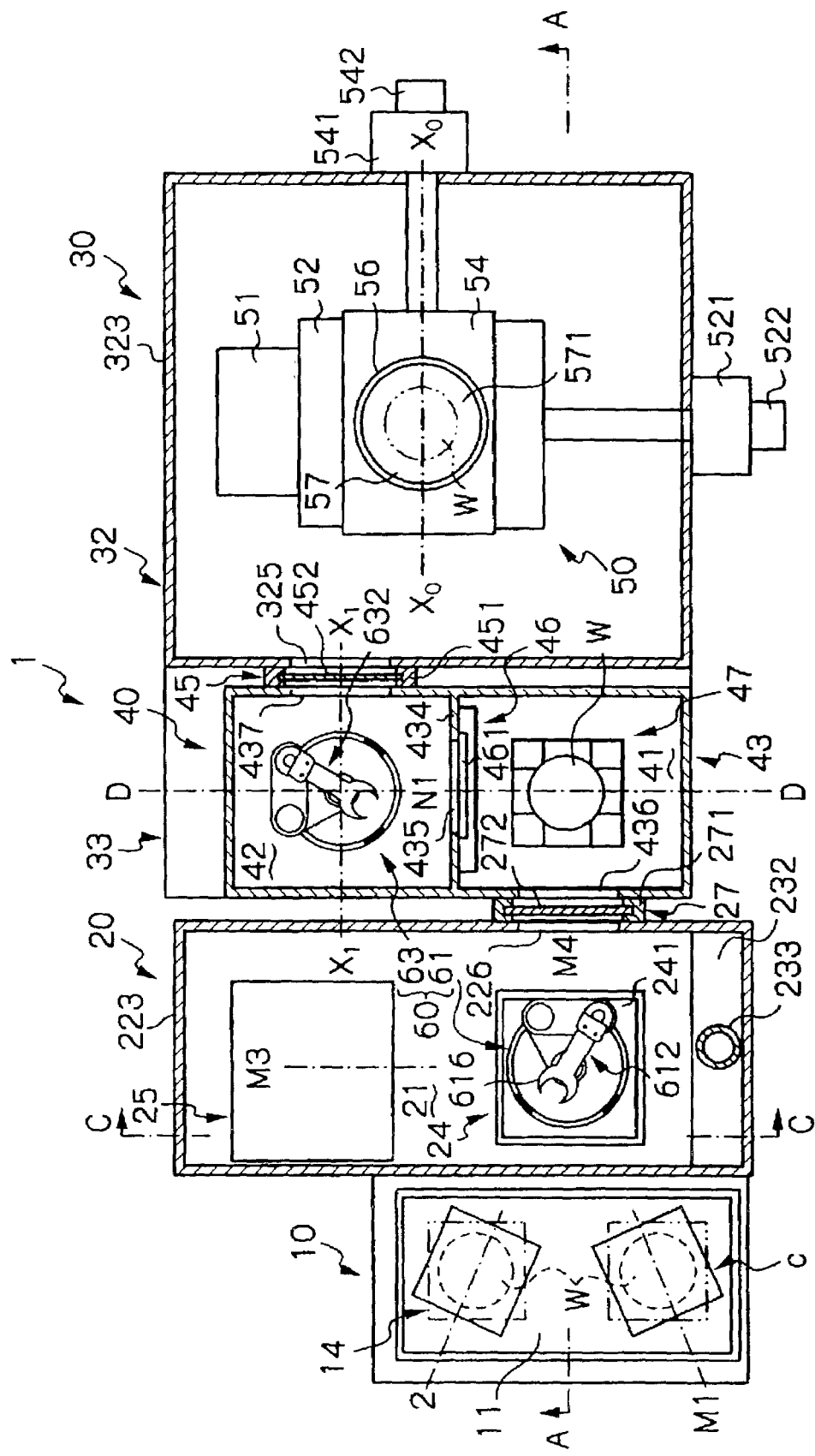
FIG. 2 is a cross-sectional plan view taken along a line B—B of FIG. 1, illustrating the main components of the inspection apparatus shown in FIG. 1 according to the present invention.

Referring to FIGS. 1 and 2, main components of a substrate inspection apparatus 1 according to an embodiment of the present invention is shown by an elevational view and a plan view.

The semiconductor testing apparatus 1 of this embodiment comprises a cassette holder 10 for holding cassettes which stores a plurality of wafers; a mini-environment chamber 20; a main housing 30 which defines a working chamber; a loader housing 40 disposed between the mini-environment chamber 20 and the main housing 30 to define two loading chambers; a loader 60 for loading a wafer from the cassette holder 10 onto a stage device 50 disposed in the main housing 30; and an electro-optical device 70 installed in the vacuum main housing 30. These components are arranged in a positional relationship as illustrated in FIGS. 1 and 2. The semiconductor testing apparatus 1 further comprises a pre-charge unit 81 disposed in the vacuum main housing 30; a potential applying mechanism 83 (see in FIG. 15) for applying a to a wafer; an electron beam calibration mechanism 85 (see in FIG. 16); and an optical microscope 871 which forms part of an alignment controller 87 for aligning the wafer on the stage device 50.

Cassette Holder

The cassette holder 10 is configured to hold a plurality (two in this embodiment) of cassettes 14 (for example, closed cassettes such as SMIF,FOUP manufactured by Assist Co.) in which a plurality (for example, 25) of wafers are placed side by side in parallel, oriented in the vertical direction. The cassette holder can be arbitrarily selected for installation adapted to a particular loading mechanism. Specifically, when a cassette, carried to the cassette holder 10, is automatically loaded into the cassette holder 10 by a robot or the like, the cassette holder 10 having a structure adapted to the automatic loading can be installed. When a cassette is manually loaded into the cassette holder 10, the cassette holder 10 having an open cassette structure can be installed. In this embodiment, the cassette holder 10 is the type adapted to the automatic cassette loading, and comprises, for example, an up/down table 11, and an elevation mechanism 12 for moving the up/down table 11 up and down. The cassette 14 can be automatically set onto the up/down table 11 in the position indicated by chain lines in FIG. 2. After the setting, the cassette c is automatically rotated to the position indicated by solid lines in FIG. 2 so that it is directed to the axis of pivotal movement of a first carrier unit within the mini-environment chamber 20. In addition, the up/down table 11 is moved down to the position indicated by chain lines in FIG. 1. In this way, the cassette holder 10 for use in automatic loading, or the cassette holder 10 for use in manual loading may be both implemented by those in known structures, so that detailed description on their structures and functions are omitted.

Figure 3:
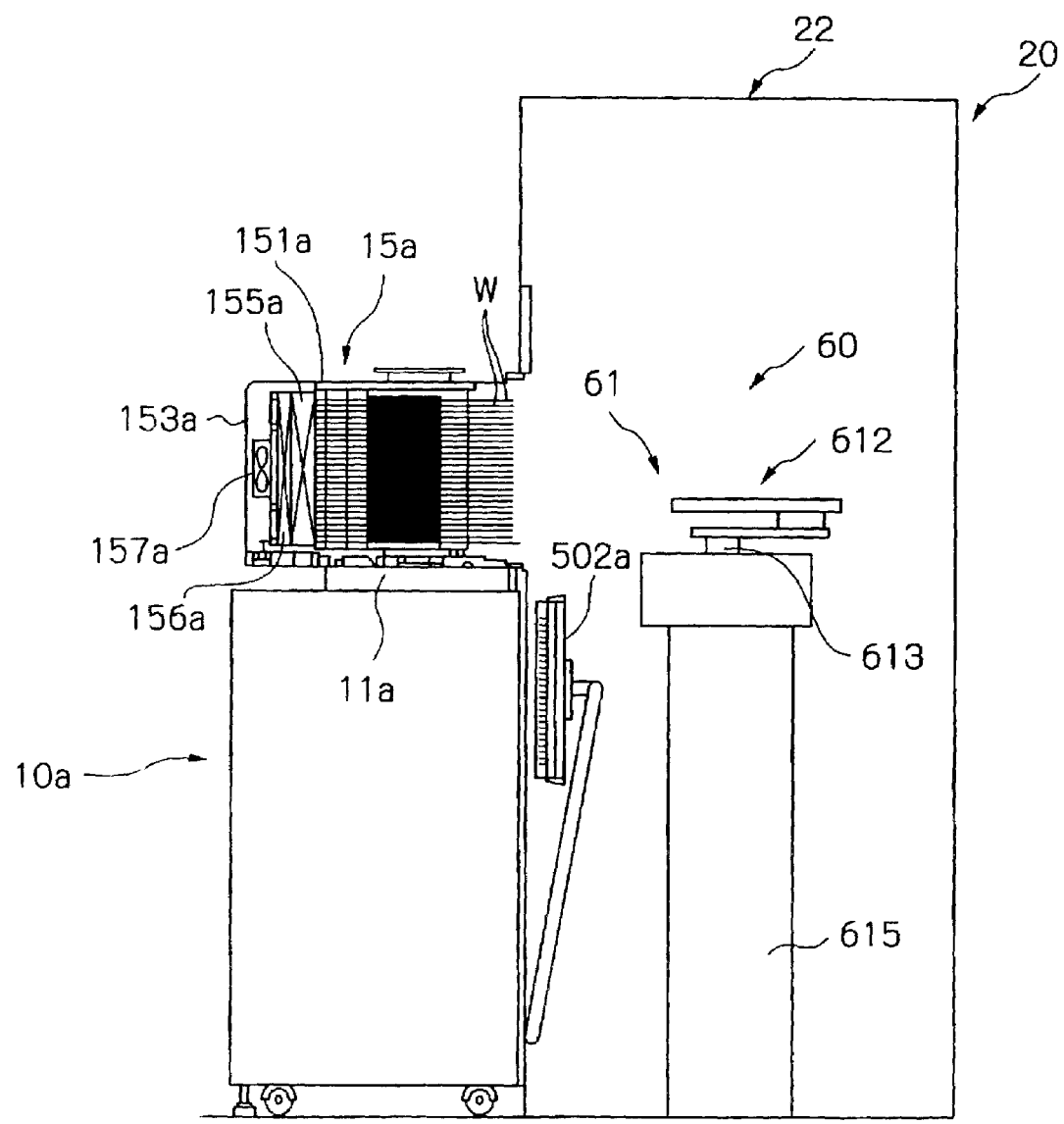
FIG. 3 is a cross sectional view of an alternative embodiment of a cassette holder.

As an alternative embodiment for the above described cassette holder 10 and cassette 14, such a device 10a as shown in FIG. 3 may be considered. This device 10a holds a plurality of substrates W with a diameter of 300 mm in a substrate carrier box 15a with each substrate being separated from others. This substrate carrier box 15a has a box main body 151 disposed on a stationary table 11a, and conveys and stores the wafers W horizontally and parallelly with each other as each contained in a slot-like pocket (not shown) fixedly mounted in said box main body. The box main body 151a of the substrate carrier box 15a has an opening in a side facing to a mini-environment chamber, and said opening is designed to be selectively opened or closed by a door 152a for carrying in/out the substrate, said door being provided in a housing 22 of the mini-environment chamber. This door 152a for carrying in/out the substrate is designed to be opened/closed by an automatic door opening/closing unit, though not shown. The device 10a comprises a lid body 153a, which is disposed in an opposite side of said opening facing to the mini-environment chamber, for covering another opening through which filters and a fun motor are to be attached or detached, said slot like pocket (not shown) for holding the substrate, a UPA filter 155a, a chemical filter 156a, and a fun motor 157a. In this embodiment also, the wafer W is carried in or out by a first transfer unit 61 of robot type in a loader 60.

It is to be noted that the substrate or the wafer received in the cassette 14 is a wafer to be subjected to an inspection, wherein said inspection is performed after or in a course of a process for processing the wafer in the semiconductor manufacturing process. In specific, such a substrate or a wafer as having been subjected to a film deposition process, a CMP process, or an ion implantation process, a wafer with a wiring pattern formed thereon or a wafer with a wiring pattern not yet formed thereon is received in the cassette. Since a plurality of wafers is received in the cassette 14 so as to be arranged horizontally and parallelly placing a space therebetween and stacked vertically, an arm of the first transfer unit is designed to be movable vertically so that a wafer in any position may be caught by said first transfer unit as will be described later.

Mini-Environment Chmber

Figure 4:
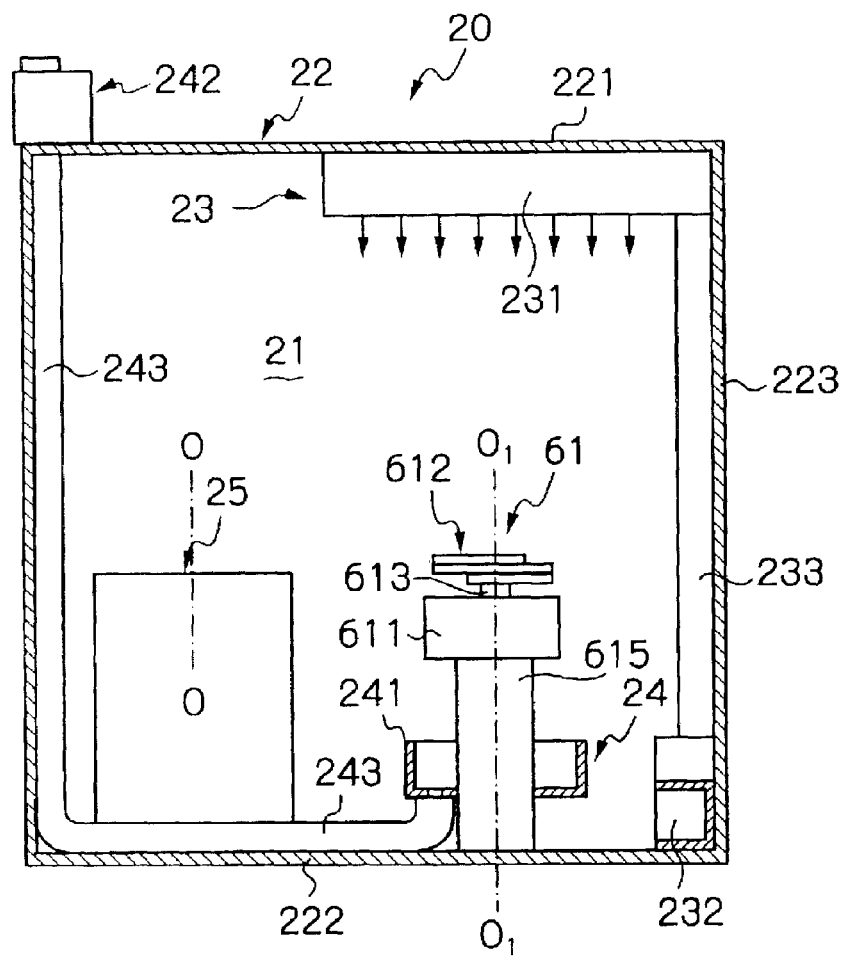
FIG. 4 is a cross sectional view taken along a line C—C of FIG. 1, illustrating a mini-environment chamber shown in FIG. 1.

In FIGS. 1, 2 and 4, the mini-environment chamber 20 comprises a housing 22 which defines a mini-environment space 21 that is controlled for an atmosphere; a gas circulating device 23 for circulating a gas such as clean air within the mini-environment space 21 for the control; a discharging device 24 for recovering a portion of air supplied into the mini-environment space 21 for discharging; and a pre-aligner 25 for roughly aligning a substrate, i.e., a wafer under testing, which is placed in the mini-environment space 21.

The housing 22 has a top wall 221, a bottom wall 222, and peripheral wall 223 which surrounds four sides of the housing 22 to provide a structure for isolating the mini-environment space 21 from the outside. For controlling the atmosphere in the mini-environment space 21, the gas circulating device 23 comprises a gas supply unit 231 attached to the top wall 221 within the mini-environment space 21 as illustrated in FIG. 4 for cleaning a gas (air in this embodiment) and delivering the cleaned gas downward through one or more gas delivering ports (not shown) in laminar flow; a recovery duct 232 disposed on the bottom wall 222 within the mini-environment space for recovering air which has flown down to the bottom; and a conduit 233 for connecting the recovery duct 232 to the gas supply unit 231 for returning recovered air to the gas supply unit 231. In this embodiment, the gas supply unit 231 takes about 20% of air to be supplied, from the outside of the housing 22 for cleaning. However, the percentage of gas taken from the outside may be arbitrarily selected. The gas supply unit 231 comprises an HEPA or ULPA filter in a known structure for creating cleaned air. The laminar downflow of cleaned air is mainly supplied such that the air passes a carrying surface formed by the first carrier unit, later described, disposed within the mini-environment space 21 to prevent dust particles, which could be produced by the carrier unit, from attaching to the wafer. Therefore, the downflow nozzles need not be positioned near the top wall as illustrated, but is only required to be above the carrying surface formed by the carrier unit. In addition, the air need not either be supplied over the entire mini-environment space 21. It should be noted that an ion wind may be used as cleaned air to ensure the cleanliness as the case may be. Also, a sensor may be provided within the mini-environment space 21 for observing the cleanliness such that the apparatus is shut down when the cleanliness is degraded. An access port 225 is formed in a portion of the peripheral wall 223 of the housing 22 that is adjacent to the cassette holder 10. A gate valve in a known structure may be provided near the access port 225 to shut the access port 225 from the mini-environment chamber 20. The laminar downflow near the wafer may be, for example, at a rate of 0.3 to 0.4 m/sec. The gas supply unit 231 may be disposed outside the mini-environment space 21 instead of within the mini-environment space 21.

The discharging device 24 comprises a suction duct 241 disposed at a position below the wafer carrying surface of the carrier unit and below the carrier unit; a blower 242 disposed outside the housing 22; and a conduit 243 for connecting the suction duct 241 to the blower 242. The discharging device 24 sucks a gas flowing down around the carrier unit and including dust, which could be produced by the carrier unit, through the suction duct 241, and discharges the gas outside the housing 22 through the conduits 243, 244 and the blower 242. In this event, the gas may be emitted into an exhaust pipe (not shown) which is laid to the vicinity of the housing 22.

The aligner 25 disposed within the mini-environment space 21 optically or mechanically detects an orientation flat (which refers to a flat portion formed on the outer periphery of a circular wafer) formed on the wafer, or one or more V-shaped notches formed on the outer peripheral edge of the wafer to previously align the position of the wafer in a rotating direction about the axis $O_1$—$O_1$ at an accuracy of approximately ± one degree. The pre-aligner forms part of a mechanism for determining the coordinates of an object under testing and is responsible for rough alignment of an object under testing. Since the pre-aligner itself may be of a known structure, description on its structure and operation is omitted.

Although not shown, a recovery duct for the discharger 24 may also be provided below the pre-aligner such that air including dust, emitted from the pre-aligner, is discharged to the outside.

Main Housing

In FIGS. 1 and 2, the main housing 30, which defines the working chamber 31, comprises a housing body 32 that is supported by a housing supporting device 33 fixed on a vibration isolator 37 disposed on a base frame 36. The housing supporting device 33 comprises a frame structure 331 assembled into a rectangular form. The housing body 32 comprises a bottom wall 321 securely fixed on the frame structure 331; a top wall 322; and a peripheral wall 323 which is connected to the bottom wall 321 and the top wall 322 and surrounds four sides of the housing body 32, and isolates the working chamber 31 from the outside. In this embodiment, the bottom wall 321 is made of a relatively thick steel plate to prevent distortion due to the weight of equipment carried thereon such as the stage device. Alternatively, another structure may be employed. In this embodiment, the housing body 32 and the housing supporting device 33 are assembled into a rigid construction, and the vibration isolator 37 prevents vibrations from the floor, on which the base frame 36 is placed, from being transmitted to the rigid structure. A portion of the peripheral wall 323 of the housing body 32 that adjoins the loader housing 40, later described, is formed with an access port 325 for introducing and removing a wafer.

The vibration isolator 37 may be either of an active type which has an air spring, a magnetic bearing and so on, or a passive type likewise having these components. Since any known structure may be employed for the vibration isolator 37, description on the structure and functions of the vibration isolator itself is omitted. The working chamber 31 is held in a vacuum atmosphere by a vacuum system (not shown) in a known structure. A controller 2 for controlling the operation of the overall apparatus is disposed below the base frame 36.

The vacuum system described above is composed of a vacuum pump, a vacuum valve, a vacuum gauge, a vacuum pipe and the like, though each being not shown, and exhausts to vacuum an electronic optical system, a detector section, a working chamber and a loading chamber which will be described later, according to a predetermined sequence. In each of those sections, the vacuum valve is controlled so as to accomplish a required vacuum level. The vacuum level is regularly monitored, and in the case of irregularity, an interlock function executes an emergency control such as an interception of communication between the chambers or between the chamber and the evacuating system by an isolation valve, though not shown, to secure the vacuum level for each section. As for the vacuum pump, a turbo molecular pump may be used for main exhaust, and a dry pump of Root type may be used as a roughing vacuum pump. A pressure at an inspection spot (an electron beam irradiating section) or in the working chamber is practically in a range of $10^{-3}$ to $10^{-5}$ Pa, preferably in a range of $10^{-4}$ to $10^{-6}$ Pa as shifted by one digit down.

Loader Housing

Figure 5:
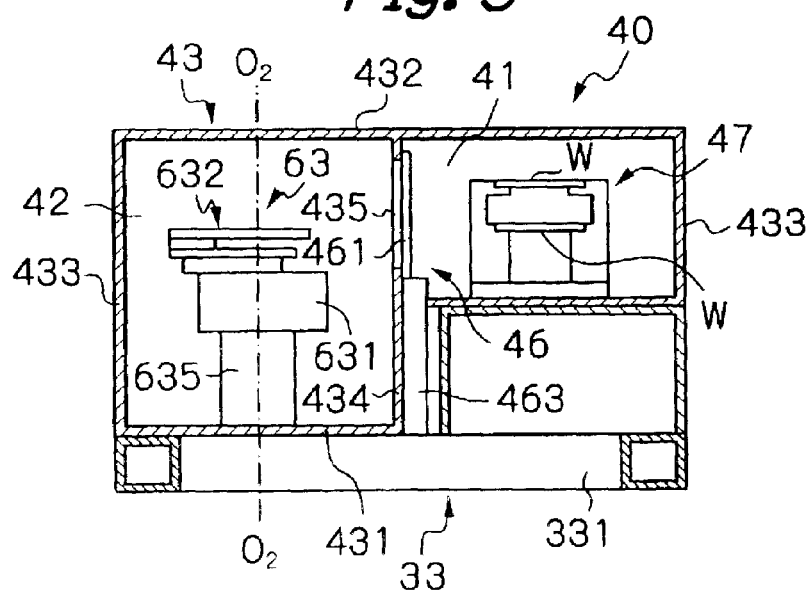
FIG. 5 is a cross sectional view taken along a line D—D of FIG. 2, illustrating a loader housing shown in FIG. 1.

In FIGS. 1, 2 and 5, the loader housing 40 comprises a housing body 43 which defines a first loading chamber 41 and a second loading chamber 42. The housing body 43 comprises a bottom wall 431; a top wall 432; a peripheral wall 433 which surrounds four sides of the housing body 43; and a partition wall 434 for partitioning the first loading chamber 41 and the second loading chamber 42 such that both the loading chambers can be isolated from the outside. The partition wall 434 is formed with an aperture, i.e., an access port 435 for passing a wafer between both the loading chambers. Also, portions of the peripheral wall 433 that adjoin the mini-environment chamber 20 and the main housing 30 is formed with access ports 436 and 437, respectively. The housing body 43 of the loader housing 40 is carried on and supported by the frame structure 331 of the housing supporting device 33. This prevents the vibrations of the floor from being transmitted to the loader housing 40 as well. The access port 436 of the loader housing 40 is in alignment with the access port 226 of the housing 22 of the mini-environment chamber 20, and a gate valve 27 is provided for selectively isolating a interaction between the mini-environment space 21 and the first loading chamber 41. The gate valve 27 has a sealing material 271 which surrounds the peripheries of the access ports 226, 436 and is fixed to the side wall 433 in close contact therewith; a door 272 for isolating air from flowing through the access ports in cooperation with the sealing material 271; and an actuator 273 for moving the door 272. Likewise, the access port 437 of the loader housing 40 is in alignment with the access port 325 of the housing body 32, and a gate valve 45 is provided for selectively isolating a intraction between the second loading chamber 42 and the working chamber 31 in a hermetic manner. The gate valve 45 comprises a sealing material 451 which surrounds the peripheries of the access ports 437 and 325 and is fixed to side walls 433 and 323 in close contact therewith; a door 452 for isolating air from flowing through the access ports in cooperation with the sealing material 451; and an actuator 453 for moving the door 452. Further, the aperture formed through the partition wall 434 is provided with a gate valve 46 for closing the aperture with the door 461 to selectively isolating a interaction between the first and second loading chambers in a hermetic manner. These gate valve 27, 45, 46 are configured to provide air-tight sealing for the respective chambers when they are in a closed state. Since these gate valve may be implemented by known ones, detailed description on their structures and operations is omitted. It should be noted that a method of supporting the housing 22 of the mini-environment chamber 20 is different from a method of supporting the loader housing 40. Therefore, for preventing vibrations from being transmitted from the floor through the mini-environment chamber 20 to the loader housing 40 and the main housing 30, a vibration-absorption damping material may be disposed between the housing 22 and the loader housing 40 to provide air-tight sealing for the peripheries of the access ports.

Figure 6A:
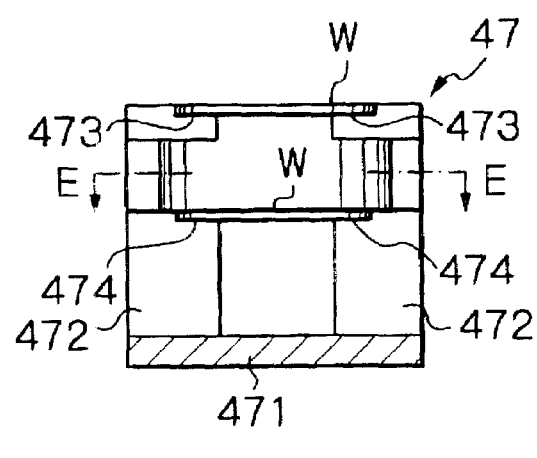
FIG. 6 is an enlarged view of a wafer rack, wherein (A) is a side elevational view and (B) is a cross sectional view taken along a line E—E of (A)
Figure 6B:
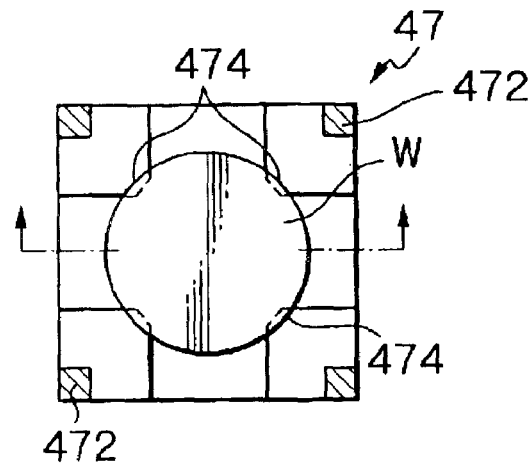

Within the first loading chamber 41, a wafer rack 47 is disposed for supporting a plurality (two in this embodiment) of wafers spaced in the vertical direction and maintained in a horizontal position. As illustrated in FIG. 6, the wafer rack 47 comprises posts 472 fixed at four corners of a rectangular substrate 471, spaced from one another, in an upright position. Each of the posts 472 is formed with supporting devices 473 and 474 in two stages, such that peripheral edges of wafers W are carried on and held by these supporting devices. Then, leading ends of arms of the first and second carrier units, later described, are brought closer to wafers from adjacent posts and grab the wafers.

The loading chambers 41 and 42 can be controlled for the atmosphere to be maintained in a high vacuum condition (at a pressure of $10^{-5}$ to $10^{-6}$ Pa) by a pumping system (not shown) in a known structure including a vacuum pump for the working chamber, not shown. In this event, the first loading chamber 41 may be held in a low vacuum condition as a low vacuum chamber, while the second loading chamber 42 may be held in a high vacuum condition as a high vacuum chamber, to effectively prevent contamination of wafers. The employment of such a structure allows a wafer, which is accommodated in the loading chamber and is next subjected to the defect testing, to be carried into the working chamber without delay. The employment of such a loading chambers provides for an improved throughput for the defect testing, and the highest possible vacuum condition around the electron source which is required to be kept in a high vacuum condition, together with the principle of a multi-beam type electron system, later described.

The first and second loading chambers 41 and 42 are connected to a vacuum exhaust pipe and a vent pipe for an inert gas (for example, dried pure nitrogen) (neither of which are shown), respectively. In this way, the atmospheric state within each loading chamber is attained by an inert gas vent (which injects an inert gas to prevent an oxygen gas and so on other than the inert gas from attaching on the surface). Since an apparatus itself for implementing the inert gas vent is known in structure, detailed description thereon is omitted.

In the testing apparatus according to the present invention which uses an electron beam, when representative lanthanum hexaboride ($LaB_6$) used as an electron source for an electro-optical system, later described, is once heated to such a high temperature that causes emission of thermal electrons, it should not be exposed to oxygen within the limits of possibility so as not to shorten the lifetime. The exposure to oxygen can be prevented without fail by carrying out the atmosphere control as mentioned above at a stage before loading a wafer into the working chamber in which the electron-optical system is disposed.

Stage Device

The stage device 50 comprises a fixed table 51 disposed on the bottom wall 301 of the main housing 30: a Y-table 52 movable in a Y-direction on the fixed table 51 (the direction vertical to the drawing sheet in FIG. 1); an X-table 54 movable in an X-direction on the Y-table 52 (in the left-to-right direction in FIG. 1); a turntable 56 rotatable on the X-table; and a holder 57 disposed on the turntable 56. A wafer is releasably held on a wafer carrying surface 571 of the holder 57. The holder 57 may be of a known structure which is capable of releasably grabbing a wafer by means of a mechanical or electrostatic chuck feature. The stage device 50 uses servo motors, encoders and a variety of sensors (not shown) to operate a plurality of tables as mentioned above to permit highly accurate alignment of a wafer held on the carrying surface 571 by the holder 57 in the X-direction, Y-direction and Z-direction (in the up-down direction in FIG. 1) with respect to an electron beam irradiated from the electro-optical device, and in a direction about the axis normal to the wafer supporting surface (θ direction). The alignment in the Z-direction may be made such that the position on the carrying surface of the holder, for example, can be finely adjusted in the Z-direction. In this event, a reference position on the carrying surface is sensed by a position measuring device using a laser of an extremely small diameter (a laser interferometer) to control the position by a feedback circuit, not shown. Additionally or alternatively, the position of a notch or an orientation flat of a wafer is measured to sense a plane position or a rotational position of the wafer relative to the electron beam to control the position of the wafer by rotating the turntable 54 by a stepping motor which can be controlled in extremely small angular increments. In order to maximally prevent particle produced within the working chamber, servo motors 531, 531 and encoders 522, 532 for the stage device 50 are disposed outside the main housing 30. Since the stage device 50 may be of a known structure used, for example, in steppers and so on, detailed description on its structure and operation is omitted. Likewise, since the laser interferometer may also be of a known structure, detailed description on its structure and operation is omitted.

It is also possible to establish a basis for signals which are generated by previously inputting a rotational position, and X-, Y-positions of a wafer relative to the electron beam in a signal detecting system or an image processing system, later described. The wafer chucking mechanism provided in the holder is configured to apply a voltage for chucking a wafer to an electrode of an electrostatic chuck, and the alignment is made by pinning three points on the outer periphery of the wafer (preferably spaced equally in the circumferential direction). The wafer chucking mechanism comprises two fixed aligning pins and a push-type clamp pin. The clamp pin can implement automatic chucking and automatic releasing, and constitutes a conducting spot for applying the voltage. While in this embodiment, the X-table is defined as a table which is movable in the left-to-right direction in FIG. 2; and the Y-table as a table which is movable in the up-down direction, a table movable in the left-to-right direction in FIG. 2 may be defined as the Y-table; and a table movable in the up-down direction as the X-table.

Loader

The loader 60 comprises a robot-type first carrier unit 61 disposed within the housing 22 of the mini-environment chamber 20; and a robot-type second carrier unit 63 disposed within the second loading chamber 42.

The first carrier unit 61 comprises a multi-node arm 612 rotatable about an axis $O_1$—$O_1$ with respect to an actuator 611. While an arbitrary structure may be used for the multi-node arm, the multi-node arm in this embodiment has three parts which are pivotably attached to each other. One part of the arm 612 of the first carrier unit 61, i.e., the first part closest to the actuator 611 is attached to a rotatable shaft 613 by a driving mechanism (not shown) of a known structure, disposed within the actuator 611. The arm 612 is pivotable about the axis $O_1$—$O_1$ by means of the shaft 613, and radially telescopic as a whole with respect to the axis $O_1$—$O_1$ through relative rotations among the parts. At a leading end of the third part of the arm 612 furthest away from the shaft 613, a holding device 616 in a known structure for holding a wafer, such as a mechanical chuck or an electrostatic chuck, is disposed. The actuator 611 is movable in the vertical direction by an elevating mechanism 615 in a known structure.

The first carrier unit 61 extends the arm 612 in either a direction M1 or a direction M2 of two cassettes 14 held in the cassette holder 10, and removes a wafer accommodated in a cassette 14 by carrying the wafer on the arm or by grabbing the wafer with the chuck (not shown) attached at the leading end of the arm. Subsequently, the arm is retracted (in a position as illustrated in FIG. 2), and then rotated to a position at which the arm can extend in a direction M3 toward the prealigner 25, and stopped at this position. Then, the arm is again extended to transfer the wafer held on the arm to the prealigner 25. After receiving a wafer from the prealigner 25, contrary to the foregoing, the arm is further rotated and stopped at a position at which it can extend to the second loading chamber 41 (in the direction M3), and transfers the wafer to a wafer rack 47 within the second loading chamber 41. For mechanically grabbing a wafer, the wafer should be grabbed on a peripheral region (in a range of approximately 5 mm from the peripheral edge). This is because the wafer is formed with device construction (circuit patterns) over the entire surface except for the peripheral region, and grabbing the inner region would result in failed or defective devices.

The second carrier unit 63 is basically identical to the first carrier unit 61 in structure except that the second carrier unit 63 carries a wafer between the wafer rack 47 and the carrying surface of the stage device 50, so that detailed description thereon is omitted.

In the loader 60, the first and second carrier units 61 and 63 each carry a wafer from a cassette held in the cassette holder 10 to the stage device 50 disposed in the working chamber 31 and vice versa, while remaining substantially in a horizontal position. The arms of the carrier units are moved in the vertical direction only when a wafer is removed from and inserted into a cassette, when a wafer is carried on and removed from the wafer rack, and when a wafer is carried on and removed from the stage device 50. It is therefore possible to smoothly carry a larger wafer, for example, a wafer having a diameter of 30 cm.

Next, how a wafer is carried will be described in sequence from the cassette 14 held by the cassette holder 10 to the stage device 50 disposed in the working chamber 31.

As described above, when the cassette is manually set, the cassette holder 10 having a structure adapted to the manual setting is used, and when the cassette is automatically set, the cassette holder 10 having a structure adapted to the automatic setting is used. In this embodiment, as the cassette 14 is set on the up/down table 11 of the cassette holder 10, the up/down table 11 is moved down by the elevating mechanism 12 to align the cassette c with the access port 225.

As the cassette is aligned with the access port 225, a cover (not shown) provided for the cassette is opened, and a cylindrical cover is applied between the cassette 14 and the access port 225 of the mini-environment to block the cassette and the mini-environment space 21 from the outside. Since these structures are known, detailed description on their structures and operations is omitted. When the mini-environment chamber 20 is provided with a gate for opening and closing the access port 225, the gate is operated to open the access port 225.

On the other hand, the arm 612 of the first carrier unit 61 remains oriented in either the direction M1 or M2 (in the direction M1 in this description). As the access port 225 is opened, the arm 612 extends to receive one of wafers accommodated in the cassette at the leading end. While the arm and a wafer to be removed from the cassette are adjusted in the vertical position by moving up or down the actuator 611 of the first carrier unit 61 and the arm 612 in this embodiment, the adjustment may be performed by moving up and down the up/down table 11 of the cassette holder 10, or performed by both.

As the arm 612 has received the wafer, the arm 621 is retracted, and the gate is operated to close the access port (when the gate is provided). Next, the arm 612 is pivoted about the axis $O_1$—$O_1$ such that it can extend in the direction M3. Then, the arm 612 is extended and transfers the wafer carried at the leading end or grabbed by the chuck onto the prealigner 25 which aligns the orientation of the rotating direction of the wafer (the rotational direction about the central axis vertical to the wafer plane) within a predetermined range. Upon completion of the alignment, the carrier unit 61 retracts the arm 612 after a wafer has been received from the prealigner 25 to the leading end of the arm 612, and takes a posture in which the arm 612 can be extended in a direction M4. Then, the door 272 of the gate valve 27 is operated to open the access ports 223, 236, and the arm 612 is extended to place the wafer on the upper stage or the lower stage of the wafer rack 47 within the first loading chamber 41. It should be noted that before the gate valve 27 opens the access ports to transfer the wafer to the wafer rack 47, the aperture 435 formed through the partition wall 434 is closed by the door 461 of the gate valve 46 in an air-tight state.

In the process of carrying a wafer by the first carrier unit, clean air flows (as a downflow) in laminar flow from the gas supply unit 231 disposed on the housing of the mini-environment chamber to prevent particle from attaching on the upper surface of the wafer during the carriage. A portion of the air near the carrier unit (in this embodiment, about 20% of the air supplied from the supply unit 231, mainly contaminated air) is drawn from the suction duct 241 of the discharging device 24 and emitted outside the housing. The remaining air is recovered through the recovery duct 232 disposed on the bottom of the housing and returned again to the gas supply unit 231.

As the wafer is placed into the wafer rack 47 within the first loading chamber 41 of the loader housing 40 by the first carrier unit 61, the gate valve 27 is closed to seal the loading chamber 41. Then, the first loading chamber 41 is filled with an inert gas to expel air. Subsequently, the inert gas is also evacuated so that a vacuum atmosphere dominates within the loading chamber 41. The vacuum atmosphere within the loading chamber 41 may be at a low vacuum degree. When a certain degree of vacuum is provided within the loading chamber 41, the gate valve 46 is operated to open the access port 434 which has been sealed by the door 461, and the arm 632 of the second carrier unit 63 is extended to receive one wafer from the wafer receiver 47 with the holding device at the leading end (the wafer is carried on the leading end or held by the chuck attached to the leading end). Upon completion of the receipt of the wafer, the arm 632 is retracted, followed by the gate 46 again operated to close the access port 435 by the door 461. It should be noted that the arm 632 has previously taken a posture in which it can extend in the direction N1 of the wafer rack 47 before the gate 46 is operated to open the access port 435. Also, as described above, the access ports 437, 325 have been closed by the door 452 of the gate valve 45 before the gate valve 46 is operated to block the interaction between the second loading chamber 42 and the working chamber 31 in an air-tight condition, so that the second loading chamber 42 is evacuated.

As the gate valve 46 is operated to close the access port 435, the second loading chamber 42 is again evacuated at a higher degree of vacuum than the first loading chamber 41. Meanwhile, the arm of the second carrier unit 61 is rotated to a position at which it can extend toward the stage device 50 within the working chamber 31. On the other hand, in the stage device 50 within the working chamber 31, the Y-table 52 is moved upward, as viewed in FIG. 2, to a position at which the center line $X_0$—$X_0$ of the X-table 54 substantially matches an X-axis $X_1$—$X_1$ which passes a pivotal axis $O_2$— $O_2$ of the second carrier unit 63. The X-table 54 in turn is moved to the position closest to the leftmost position in FIG. 2, and remains awaiting at this position. When the second loading chamber 42 is evacuated to substantially the same degree of vacuum as the working chamber 31, the door 452 of the gate valve 45 is moved to open the access ports 437, 325, allowing the arm 632 to extend so that the leading end of the arm 632, which holds a wafer, approaches the stage device 50 within the working chamber 31. Then, the wafer is placed on the carrying surface 571 of the stage device 50. As the wafer has been placed on the carrying surface 571, the arm is retracted, followed by the gate valve 45 operated to close the access ports 437, 325.

The foregoing description has been made on the operation until a wafer in the cassette 14 is carried and placed on the stage device. For returning a wafer, which has been carried on the stage device and processed, from the stage device to the cassette 14, the operation reverse to the foregoing is performed. Since a plurality of wafers are stored in the wafer rack 47, the first carrier unit 61 can carry a wafer between the cassette and the wafer rack 47 while the second carrier unit 63 is carrying a wafer between the wafer rack 47 and the stage device 50, so that the testing operation can be efficiently carried out.

In specific, when there are a wafer W, which has been already processed, and a wafer W, which has not yet been processed, in a wafer rack 47 in the first loading chamber, at first, the wafer which has not yet been processed is transferred to the stage 50 and the processing is started. During this processing, the wafer which has already been processed is transferred from the stage 50 to the wafer rack 47. On the other hand, the other which has not yet been processed is picked up from the wafer rack 47 again by the arm, which after having been positioned by a pre-aligner, is further transferred to the wafer rack 47 of a loading chamber 41. This procedure may allow, in the wafer rack 47, the wafer A which has already been processed to be substituted by the wafer which has not yet been processed, during the wafer being processed.

Alternatively, depending on the way how to use such an apparatus for executing an inspection and/or an evaluation, a plurality of stage units 50 may be arranged in parallel, so that the wafers may be transferred from one wafer rack 47 to each of the stage units 50 thereby applying a similar processing to a plurality of wafers.

Modifications of Main Housing

Figure 7A:
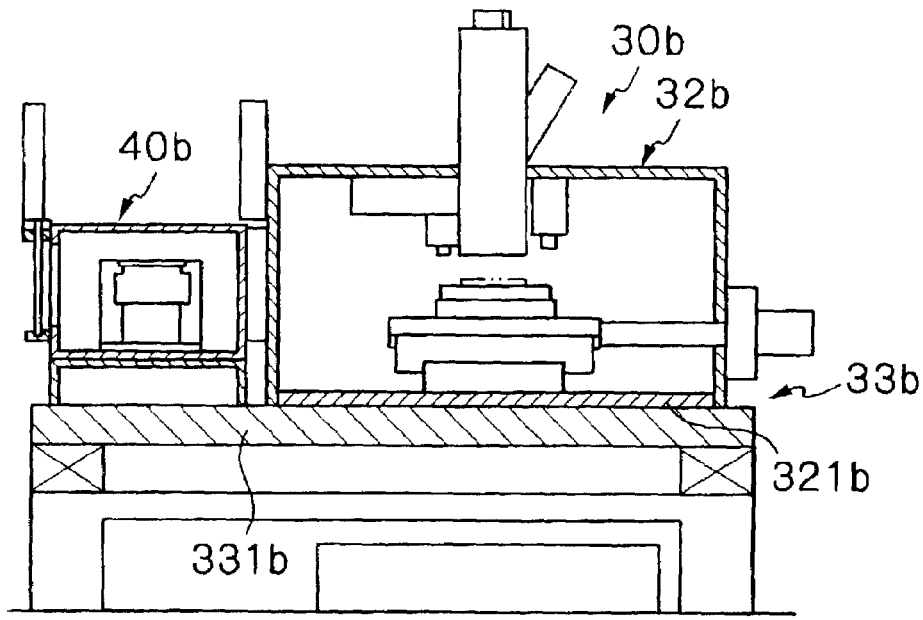
FIG. 7 shows an alternative embodiment of a main housing support system.
Figure 7B:
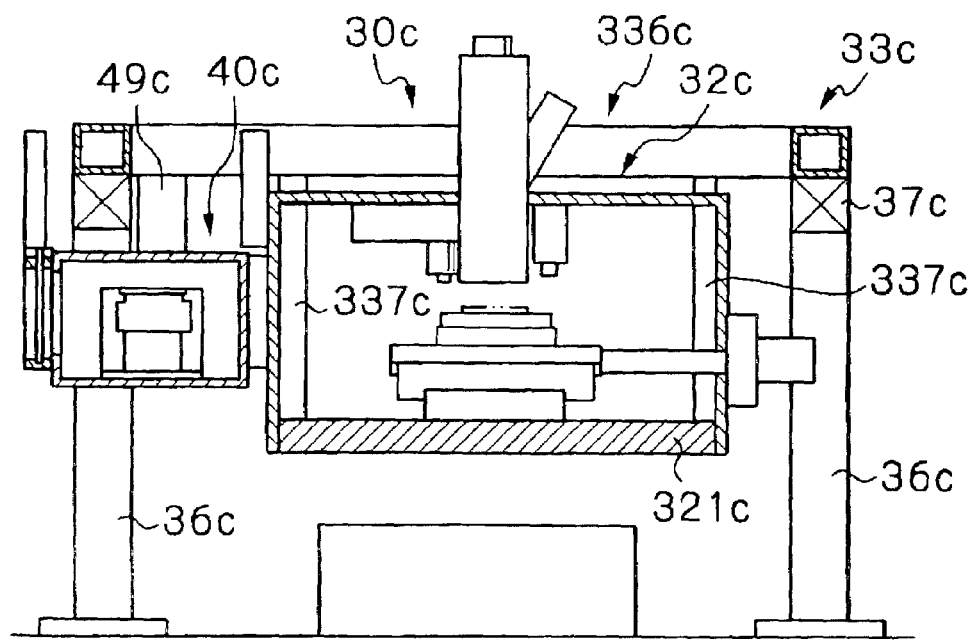

FIG. 7 illustrate exemplary modifications to the method of supporting the main housing 30. In an exemplary modification illustrated in FIG. 7(B), a housing supporting device 33c is made of a thick rectangular steel plate 331c, and a housing body 32c is placed on the steel plate. Therefore, the bottom wall 321c of the housing body 32c is thinner than the bottom wall 222 of the housing body 32 in the foregoing embodiment. In an exemplary modification illustrated in FIG. 7(B), a housing body 32c and a loader housing 40c are suspended by a frame structure 336c of a housing supporting device 33c. Lower ends of a plurality of vertical frames 337c fixed to the frame structure 336c are fixed to four corners of a bottom wall 321c of the housing body 32c, such that the peripheral wall and the top wall are supported by the bottom wall. A vibration isolator 37c is disposed between the frame structure 336c and a base frame 36c. Likewise, the loader housing 40 is suspended by a suspending member 49c fixed to the frame structure 336. In the exemplary modification of the housing body 32c illustrated in FIG. 7(B), the housing body 32c is supported in suspension, the general center of gravity of the main housing and a variety of devices disposed therein can be brought downward. The methods of supporting the main housing and the loader housing, including the exemplary modifications described above, are configured to prevent vibrations from being transmitted from the floor to the main housing and the loader housing.

In another exemplary modification, not shown, the housing body of the main housing is only supported by the housing supporting device from below, while the loader housing may be placed on the floor in the same way as the adjacent mini-environment chamber. Alternatively, in a further exemplary modification, not shown, the housing body of the main housing is only supported by the frame structure in suspension, while the loader housing may be placed on the floor in the same way as the adjacent mini-environment chamber.

Electron Beam Apparatus

Figure 8:
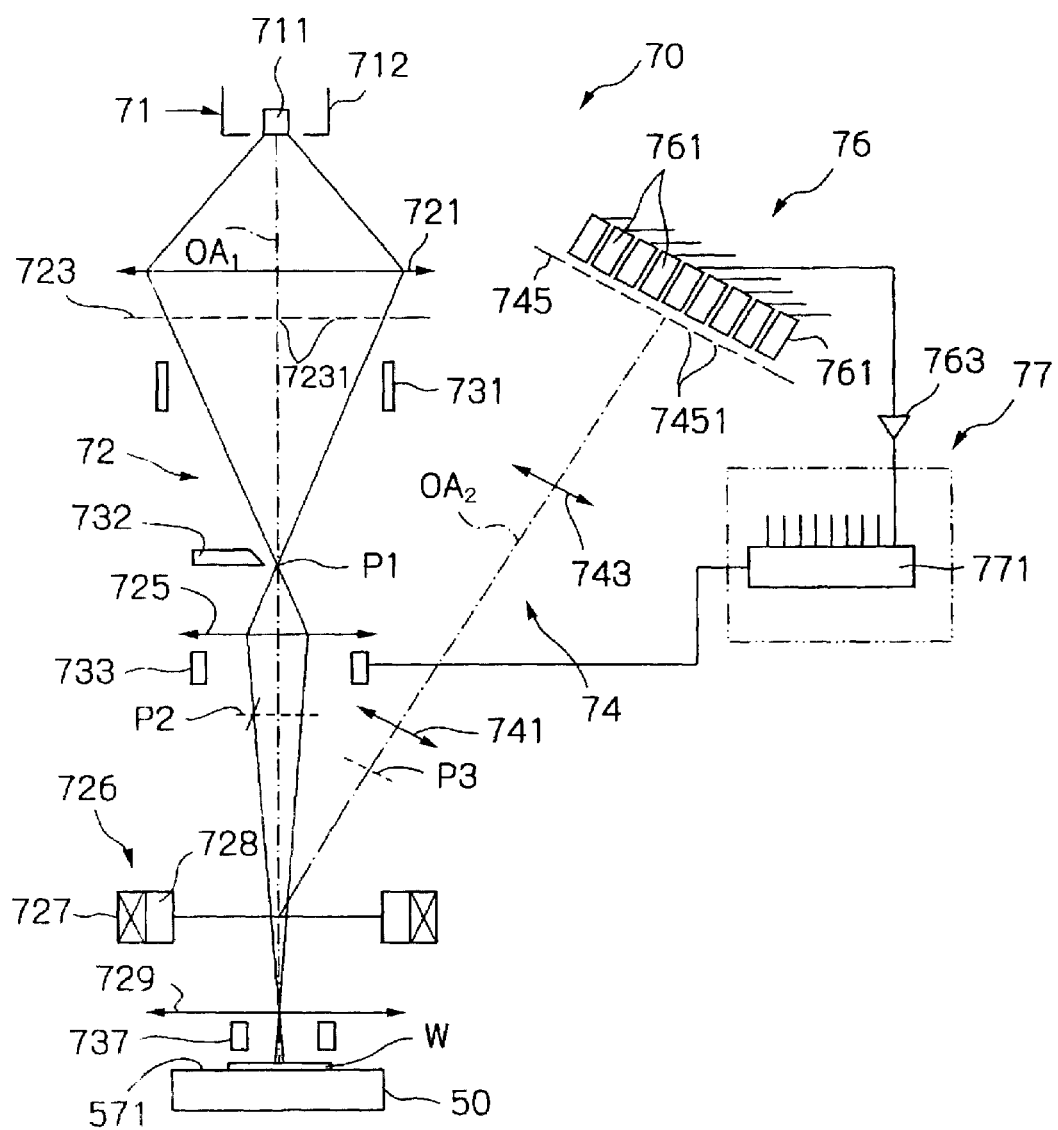
FIG. 8 is a diagram illustrating a general configuration of an electronic optical system of the inspection apparatus shown in FIG. 1.
Figure 9:
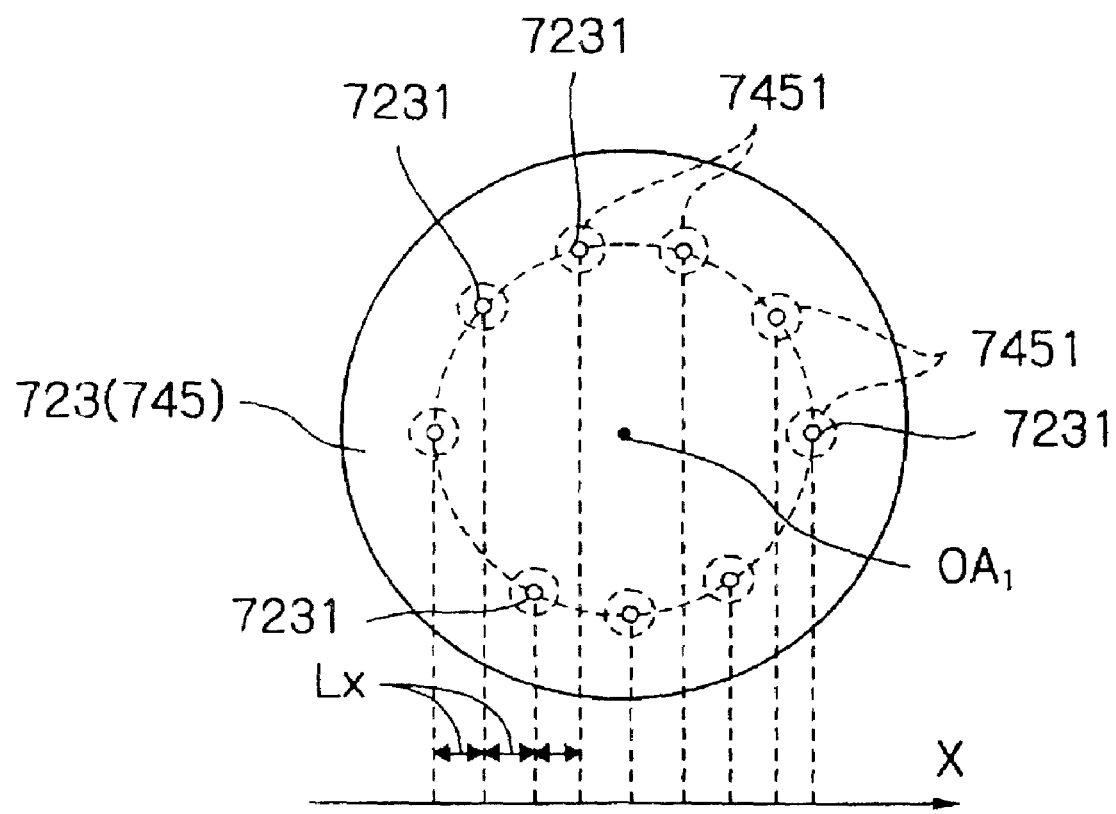
FIG. 9 shows a positional relationship between apertures in a multi aperture plate used in an primary optical system of the electron optical system shown in FIG. 8.

An electron optical apparatus 70 (hereafter simply refer to an electron beam apparatus) of this embodiment will be explained hereafter. The electron beam apparatus 70 comprises a optical column 701 fixedly mounted to a housing 32, said optical column containing an electron gun 71a as a device for emitting a charge particle beam, a primary electron optical system 72 (hereafter simply referred to as a primary optical system) for irradiating a electron beam (hereafter, a electron beam is used for one example of a charge particle beam) emitted from the electron gun 71 to a sample or substrate and a secondary electron optical system 74 (hereafter simply referred to as a secondary optical system) to which a secondary electron emitted from the substrate is introduced, a detecting system 76, and a process control system, as schematically illustrated in FIGS. 8 and 9.

A thermal electron beam source is employed as an electron beam source. An electron emitting member (emitter) is made of $LaB_6$. Other material may be used for the electron emitting member so far as it has a high melting point (low vapor pressure at high temperature) and a small work function. In order to generate a plurality of electron beams, two kinds of method may be used. One is such a method in which firstly a single electron beam is emitted from a single emitter (having a single projection) and then is passed through a thin plate with a plurality of apertures formed therein (aperture plate) to generate a plurality of electron beams, while in the other method, a plurality of projections is formed on the emitter so that a single electron beam may be emitted from a single projection and thereby a plurality of electron beams may be emitted as a whole. In either method, the electron beam is generated by taking advantage of such a nature that the projection facilitates a high intensity discharge occurs at a tip thereof. The electron beam generated in the other types of electron beam source such as a thermal field emission type electron beam source may be used.

It is to be noted that the thermal electron beam source is of such a method in which the electron emitting member is heated to emit electrons, while the thermal field emission electron beam source is of such a method in which a high electric field is applied to the electron emitting member to emit an electron and further the electron beam emitting section is heated so as to stabilize the electron emission.

The present invention has paid attention to the fact that a shot noise in the secondary electron can be reduced by lowering the shot noise in the primary electron beam because a main part of the shot noise in the secondary electron comes from that of the primary electron beam, and accordingly the electron gun 71 of this embodiment is constructed so that a desired degree of S/N ratio of the detection signal of the secondary electron may be accomplished even if a quantity of radiation of the primary electron beam is rather small.

A method for reducing the shot noise in the primary electron beam will be described below.

Under a condition where the electron gun is controlled by a cathode temperature, that is, the electron gun is operating in a temperature limited region, a shot noise $i_n$ emitted from the electron gun may be represented by the expression below: (See "Communication engineering handbook" edited by The Institution of Telecommunications Engineers, 1957, p. 471.)

$$i_n^2 = 2e \cdot I_p \cdot B_f \quad (1)$$

where, $i_n^2$ is a mean square of a noise current, e is a charge of an electron, $I_p$ is an anode current and $B_f$ is a frequency bandwidth of a signal amplifier. When the electron flow is in a space charge limited region, the expression (1) may be rewritten as:

$$i_n^2 = \Gamma^2 2e \cdot I_p \cdot B_f \quad (2)$$

where, $\Gamma^2$ is a shot noise reduction factor and is smaller than 1.

When the cathode temperature is high enough, $\Gamma^2$ moves to about 0.018 at the lowest, and the noise current lowers down to 13% of that in the case of the temperature limited region. Assuming that the secondary electron is nearly equal to the primary electron (secondary electron ≈ primary electron), the S/N ratio in this case may be expressed as:

$$S/N = I_p / \{\Gamma(2e \cdot I_p \cdot B_f)^{1/2}\}$$

$$= 1/\Gamma \cdot \{I_p/(2e \cdot B_f)^{1/2}\}$$

$$= n^{1/2}/(\Gamma \cdot 2^{1/2}) \quad (3)$$

When $\Gamma = 0.13$ is applied to the expression (3), the S/N ratio can be expressed as:

$$S/N = 7.7(n/2)^{1/2} \quad (4)$$

where, n is a number of the secondary electrons per pixel.

That is, the electron gun operating in the space charge limited region exhibits a performance equivalent to that in the case where, in comparison with the case of the electron gun operating in the temperature limited region (TFE case), the 59 ($=1/\Gamma^2=1/0.13^2$) times as much as electrons may be required per pixel. Since the latter has higher intensity than that of the former by approximately two digits, the latter has a possibility to be required larger beam current than the former by two digits when assuming the same beam diameter and the same optical system for both of them, but when a new optical system suitable for the former is designed, the latter may provide the beam current larger than that of the former by one digit. The S/N ratio of the latter is 1/55 of that of the former. In other words, in the electron gun in the space charge limited region, the measuring time and the dose may be as small as 0.18 times (10/55≈0.18) and 1/55 of those of the electron gun in the temperature limited region, respectively.

Whether or not the electron gun is operating in the space charge limited region can be examined by a method described below with reference to FIG. 10.

Figure 10A:
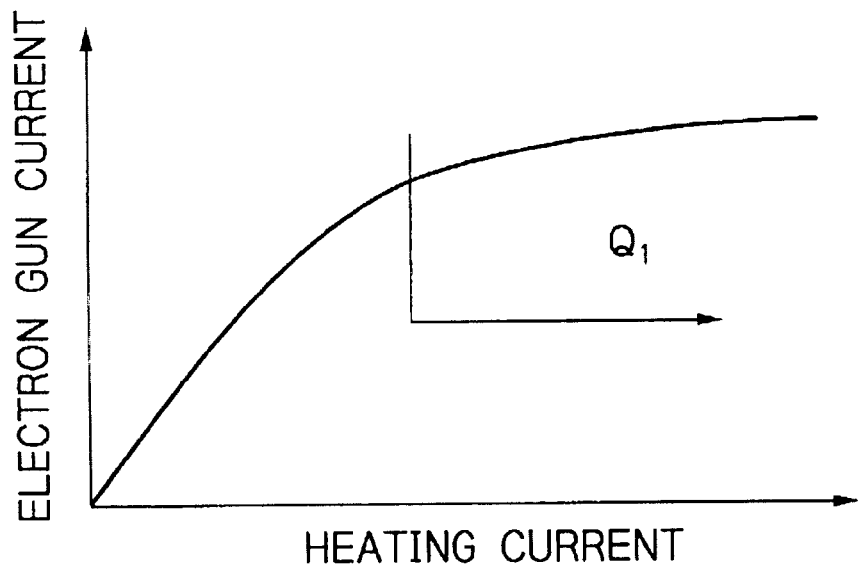
FIG. 10 illustrates an electron gun operating condition of the electron optical system shown in FIG. 8.

FIG. 10[A] shows a relation between an electron gun current and a cathode heating current. In FIG. 10(A), a region $Q_1$ is the region wherein the electron gun current hardly increases in response to an increase of the cathode heating current, that is, this region $Q_1$ is the space charge limited region.

Figure 10B:
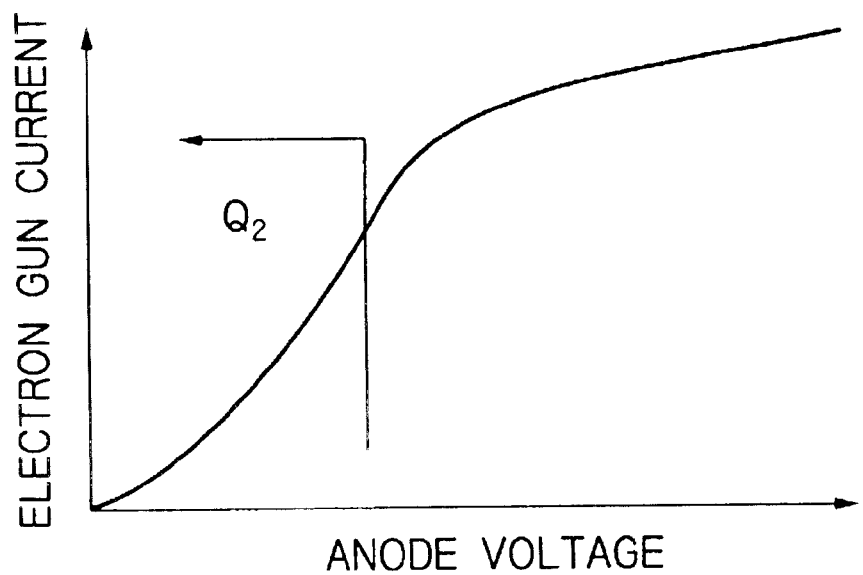

On the other hand, FIG. 10[B] shows a relation between the electron gun current and an anode voltage. In FIG. 10(B) a region $Q_2$ is the region wherein the electron gun current sharply increases in response to an increase of the anode voltage, that is, this region $Q_2$ is also the space charge limited region.

As is obvious from the above description, the electron gun may be determined to be operating in the space charge limited region if the cathode heating current of the electron gun is increased to measure the electron gun current and said electron gun current is observed to be in the saturated condition, the region Q1, or if the anode voltage of the electron gun is increased to measure the electron gun current and said electron gun current is observed to be in the steeply changing region. Accordingly, the condition for operating the electron gun in the space charge limited region may be determined.

In the electron gun 71, the heating current or the anode voltage (voltage applied to an anode 712) is set such that the electron gun 71 may operate in the space charge limited region, as described above. A cathode 711 of the electron beam 71 is made of monocrystal $LaB_6$ and has nine projections each provided with a tip of trapezoidal cone shape, though not shown. These projections are arranged along a circle so that each of them corresponds to each of a plurality of apertures in a first multi aperture plate, which will be described later with reference to FIG. 9. Each tip of these projections has a curvature of radius of about 30 μm. Since each electron beam is emitted only from a vicinity of the tip of trapezoidal cone projection, in the case of relatively high electron gun current such as about 1 mA, for the voltage of 1 kV, the intensity of $1 \times 10^4$ $A/cm^2$ sr (1 kV) may be obtained.

The primary optical system 72 serves to irradiate the primary electron beam emitted from the electron beam 71 onto a surface of a substrate or wafer W to be inspected, and comprises: an electrostatic lens or a condenser lens 721 for focusing the primary electron beam; a first multi aperture plate 723 disposed below said condenser lens 721 and provided with a plurality of apertures formed therein for forming the primary electron beam into a plurality of electron beams or multi-beams; another electrostatic lens or a reduction lens 725 for reducing the primary electron beams; an ExB separator 726 including an electromagnetic deflector 727 and an electrostatic deflector 728; and an objective lens 729, each being arranged in this order placing the condenser lens 721 at a top position as shown in FIG. 8 such that an optical axis $OA_1$ of the primary electron beam emitted from the electron gun is perpendicular to the surface of the object or wafer W to be inspected.

In order to eliminate an effect of field curvature aberration possibly caused by the reduction lens 725 and the objective lens 729, a plurality of apertures 7231 (nine apertures in this embodiment) formed in the multi aperture plate 723 is arranged along a circle around a center of the optical axis $OA_1$, such that projected points of the apertures onto X-axis may be equally spaced by Lx, as shown in FIG. 9. Each of the apertures may be, for example, a circle with a diameter of about 1 to 10 microns, and also it may be of square shape. Further, a position of the first multi aperture plate 723 is necessary to be adjusted such that the aperture may be positioned in a point where the primary electron beam emitted from the electron beam 71 has the greatest intensity. For this purpose, the multi aperture plate 723 is mounted on at least one stage of an XY stage allowing a movement in a plane including the multi aperture plate 723, a Z stage allowing a movement in a direction perpendicular to the plane including the multi aperture plate 723 and a θ stage allowing a rotation of the plane including the multi aperture plate 723, and at least one stage of the XY stage, the Z stage and the θ stage each holding the multi aperture plate is adjusted such that the intensity of the plurality of electron beams formed by the multi aperture plate 723 should be uniform and greatest.

The primary optical system 72 further comprises: an electrostatic deflector 731 for blanking; an electrostatic deflector 733 for deflecting the primary electron beam so as to cause a scanning motion; a knife edge 732 for blanking; and an axially symmetric electrode 737 disposed between the objective lens 729 and the wafer W. The axially symmetric electrode 737 is held to be, for example, a potential of −10V with respect to a potential 0V of the wafer.

Figure 11A:
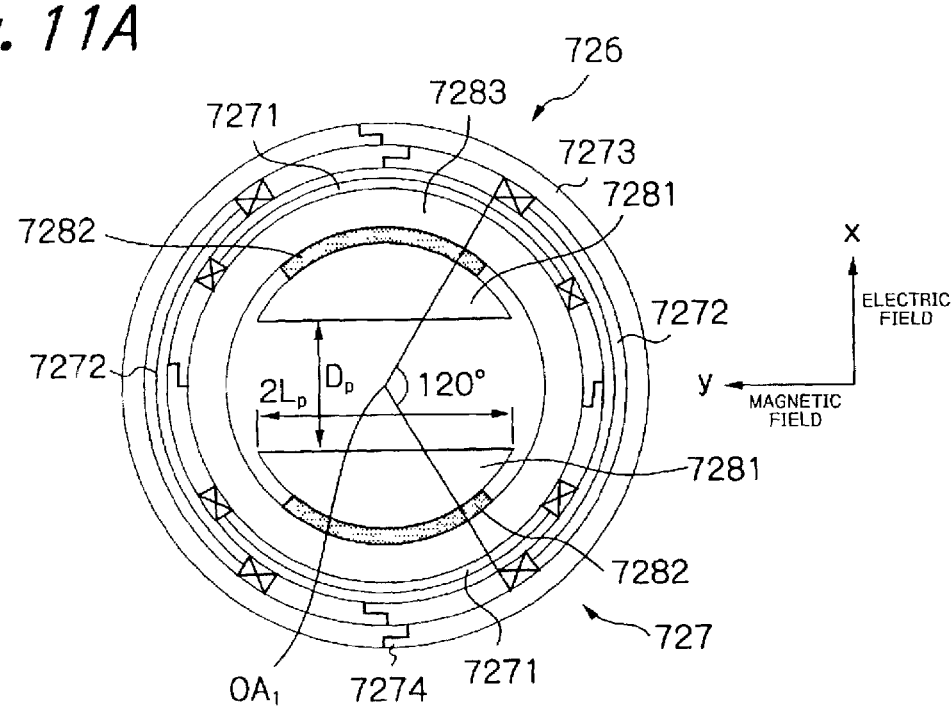
FIG. 11 illustrates an ExB separator.
Figure 11B:
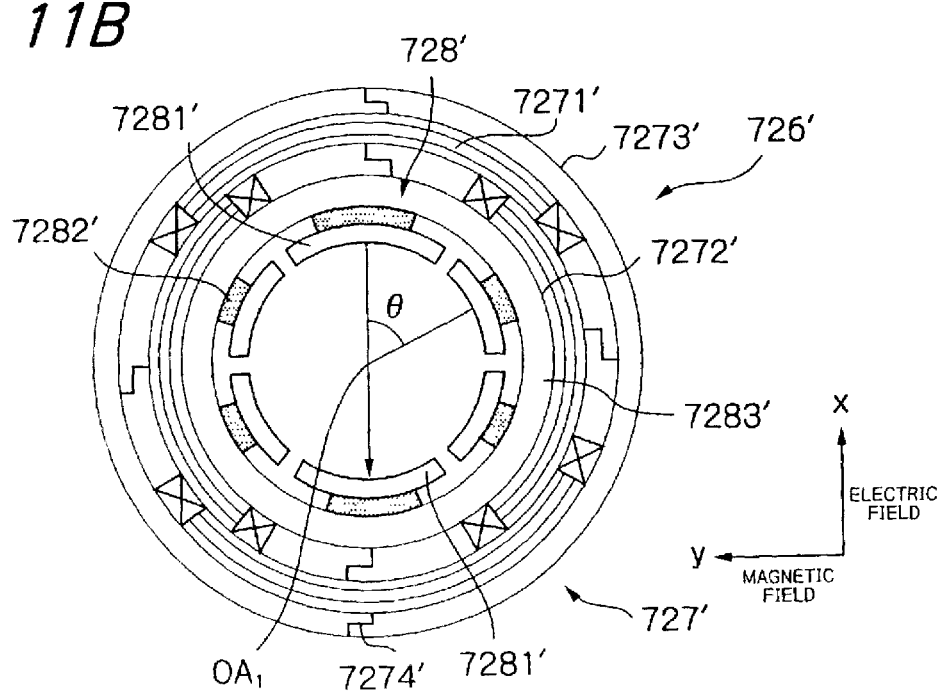

Then the ExB separator 726 will be described with reference to FIG. 11. FIG. 11[A] shows an ExB separator according to a first embodiment of the present invention. This separator consists of the electrostatic deflector 728 and the electromagnetic deflector 727, and is shown in FIG. 11 by a cross sectional views projected onto an X-Y plane perpendicular to the optical axis $OA_1$ (perpendicular to the paper of the drawing).

The electrostatic deflector 728 comprises a pair of electrodes (electrostatic deflecting electrodes) 7281 disposed in a vacuum container and generates an electric field in the X-direction. Each of these electrostatic deflecting electrodes 7281 is mounted to a vacuum wall 7283 of the vacuum container via an insulating spacer 7282, and a distance Dp between these electrodes is designed to be shorter than a length 2 Lp along the Y-direction of the electrostatic deflecting electrodes 7281. Owing to this design, an area where an electric field intensity generated around a Z axis or the optical axis $OA_1$ is uniform may be made relatively wider, wherein ideally if Dp<Lp, the area with uniform electric field intensity could be made further wider.

That is, since in an area within a distance of Dp/2 from an end of the electrode, the electric field intensity is not uniform, the area with almost uniform electric field intensity is in a central area or 2Lp-Dp area which excludes the end areas with non-uniform electric field intensity. This means that a condition of existence of the uniform electric field intensity is 2Lp>Dp, and in addition, designing to be Lp>Dp makes the uniform electric field area further wider.

On an outside of the vacuum wall 7283 is provided an magnetic deflector for generating a magnetic field in the Y-direction. The magnetic deflector 727 comprises an magnetic coil 7271 and another magnetic coil 7272, wherein each of these coils generates a magnetic field in the X- and the Y-directions respectively. It is to be noted that although the magnetic field in the Y-direction can be generated only by the coil 7272, the coil 7271 for generating the magnetic field in the X-direction is also mounted in order to improve an orthogonality between the electric field and the magnetic field. That is, the orthogonality between the electric field and the magnetic field can be improved by offsetting a magnetic field component in the +X direction generated by the coil 7272 with a magnetic field component in the −X direction generated by the coil 7271.

Each of these coils 7271 and 7272 for generating magnetic field is constituted of two pieces in order to be arranged on the outside of the vacuum container, so that these two pieces may be attached onto the vacuum wall 7283 from both sides respectively and may be clamped tightly by screw or the like at a portion 7 so as to be made into one unit.

An outermost layer 7273 of the ExB separator is constructed as a yoke made of permalloy or ferrite. Similar to the coils 7271 and 7272, the outermost layer 7273 may be made as two pieces and attached onto an outside of the coil 7272 to be formed into one unit by screwing at a portion 7274.

FIG. 11[B] shows another ExB separator according to a second embodiment of the present invention by a cross sectional view projected on a plane orthogonal to the optical axis. This ExB separator according to the second embodiment is different from that of the first embodiment shown in FIG. 11[A] in that six poles of electrostatic deflecting electrodes 7281' are provided therein. In FIG. 11[B], any components corresponding to those of the ExB separator shown in FIG. 11[A] will be designated by the same reference numerals added by "'" (dash), and the description therefor will be omitted. To each of these electrostatic deflecting electrodes 7281' is applied a voltage proportional to $\cos\theta_i$, which is represented as $k\cdot\cos\theta_i$ (k is constant), where $\theta_i$ (i=0, 1, 2, 3, 4, 5) is an angle formed between a line connecting a center of each electrode to the optical axis and a direction of the electric field (X-axis direction). It is to be noted that the $\theta_i$ is an arbitrary angle.

Since also the second embodiment shown in FIG. 11[B] can generate only the electric field in the X-axis direction similar to the first embodiment, coils 7271' and 7272' for generating the magnetic fields of X-axis direction and of Y-axis direction, respectively, are provided to correct the orthogonality.

The embodiment shown in FIG. 11[B] can make the area with uniform electric field intensity further wider than the embodiment shown in FIG. 11[A].

Although the coil for generating magnetic field has been formed into a saddle type in the embodiments shown in FIGS. 11[A] and 11[B], a coil of toroidal type may be employed.

The secondary optical system 74 comprises two magnifying lenses 741 and 743, which make up a two stage electrostatic lens, for passing therethrough a secondary electron separated from the primary optical system by the ExB separator 727, and a second multi aperture plate 745. Each of apertures 7451 formed in the second multi aperture plate 745 is adapted, as shown by a broken line in FIG. 9, to correspond one-to-one to each of the apertures 7231 formed in the first multi aperture plate 723 of the primary optical system, wherein the aperture 7451 of the second multi aperture plate 745 is a circular hole with a diameter larger than that of the aperture 7231 of the first multi aperture plate 723.

The detection system 76 comprises a plurality of detectors 761 (nine detectors in this embodiment) each disposed corresponding to and adjacent to each aperture 7451 of the second multi aperture plate 745 of the secondary optical system 74, and each of the detectors 761 is electrically connected to an image data processing section 771 of the process control system 77 via an A/D converter (including amplifier) 763. It is to be noted that though only one detector 761 has been connected to the image processing section 771 in FIG. 8, respective detectors are connected to the image data processing section via respective independent A/D converters 763. Further, the image processing section 771 is also connected to the electrostatic deflector 733 so that a scanning signal for deflecting the primary electron beam may be supplied to the electrostatic deflector 733. As an element for the detectors may be used, for example, a PN junction diode which directly detects an electron beam intensity or a PMT (photomultiplier) which detect a light emitting intensity through a scintillator which becomes luminous by electron.

The image processing section 771 may convert an electric signal supplied from respective A/D converter 763 to a binary information by setting an appropriate threshold voltage, and then may convert the binary signal into an image data. For this purpose, the scanning signal for deflecting the primary electron beam, which is supplied from the electrostatic deflector 733 to the image processing section 771, may be used. The image processing section 771 may compare the obtained image data with a reference circuit pattern, while storing thus obtained image data in an appropriate memory. Thereby, a plurality of circuit patterns, or the same number of circuit patterns with that of the primary electron beams, on the wafer W may be subjected to the inspection simultaneously.

It is to be noted that in the embodiment shown in FIG. 8, the image data processing section 771 can use various kinds of reference circuit patterns in order to compare therewith an image data representing a certain circuit pattern on the wafer W, that is, for example, an image data obtained in the same place on the other chip different from that scanned for generating said image data to be compared may be used.

An operation of the electron beam apparatus with an above configuration will now be described. The primary electron beam emitted from the electron gun 71 is converged by the condenser lens 721 in the primary optical system 72 to form a crossover at a point P1 of knife edge 732. On the other hand, the primary electron beam converged by the condenser lens 721 passes through the plurality of apertures 7231 of the multi-aperture plate 723 to form into a plurality of primary electron beams (nine beams in this embodiment), which are forcused by the reducing lens 725 so as to be projected onto a point P2. After being focused onto the point P2, the beams are further focused onto a surface of a wafer W by the objective lens 729. On the other hand, the deflecter 733 disposed between the reducing lens 725 and the objective lens 726 deflects the primary electron beams so as to scan the surface of the wafer W.

The plurality of focused primary electron beams are irradiated onto the wafer W at a plurality of points thereon, and secondary electrons are emitted from said plurality of points. Those secondary electrons are attracted by an electric field of the objective lens 729 to be converged narrower, and then deflected by the ExB separator 726 so as to be introduced into the secondary optical system 74. The secondary electron image is focused on a point P3 which is much closer to the deflector 726 than the point P2. This is because the primary electron beam has the energy of 500 eV on the surface of the wafer, while the secondary electron beam only has the energy of a few eV.

Each of the images of the secondary electrons focused at the point P3 is focused by the two-stage magnifying lenses 741 and 743 onto each of the corresponding apertures 7451 of the multi-aperture detection plate 745 to be formed into an image, so that each of the detectors 761 disposed correspondingly to each of the apertures 7451 detects the image. Each of the detectors 761 thus detects the electron beam and converts it into an electric signal representative of its intensity. The generated electric signals are output from respective detectors 761, and after being converted respectively into digital signals by the A/D converter 763, they are input to the image processing section 771 of the process control system 77. The image processing section 763 converts the input digital signals into image data. Since the image processing section 763 is further supplied with a scanning signal for deflecting the primary electron beam, the image processing section 763 can display an image representing the surface of the wafer. Comparing this image with a reference pattern that has been pre-set in a setting device (not shown) allows to determine whether or not the pattern on the wafer W being inspected (evaluated) is acceptable.

Further, the line width of the pattern formed on the surface of the wafer W can be measured in such a way that the pattern to be measured on the wafer W is moved by a registration to the proximity of the optical axis of the primary optical system, and the pattern is then line-scanned to extract the line width evaluation signal, which in turn is appropriately calibrated.

Figure 12:
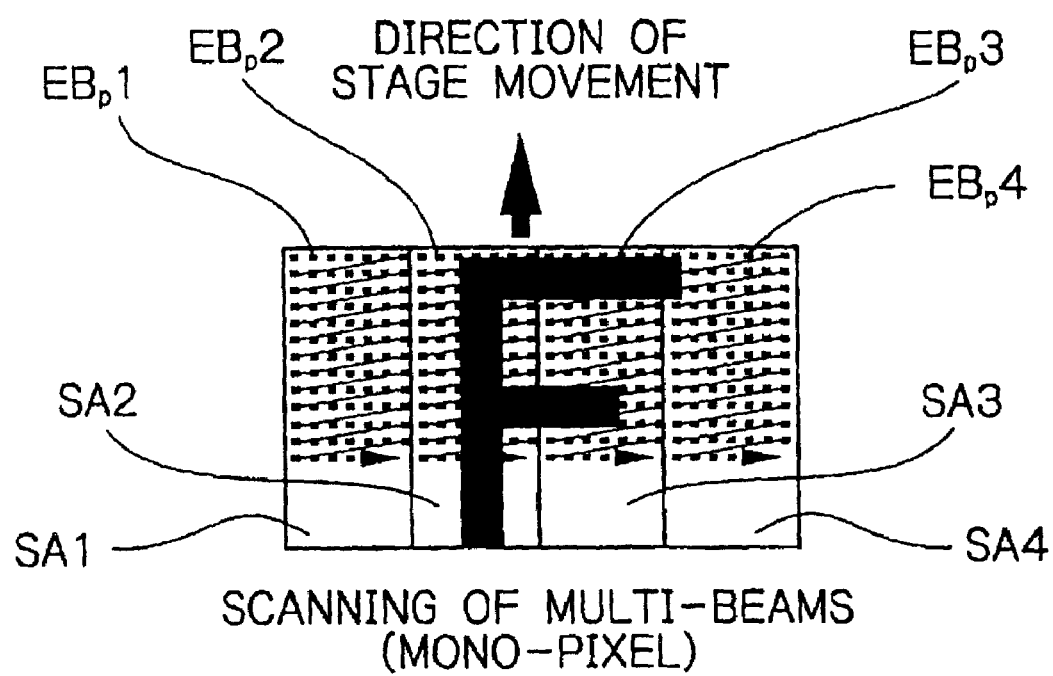
FIG. 12 illustrates a scanning/irradiating method of a primary electron beam on a wafer.

Irradiation of the primary electron beams onto a wafer while scanning them with respect to the wafer may be practiced as shown in FIG. 12. For simplicity of explanation, a case wherein the number of electron beams are four (EB1 to EB4) will be explained. Each irradiation point Ebp1 to Ebp4 of each primary electron beam designates the irradiating point of the primary electron beams which scans from the left side to the right side in the X direction in corresponding, respective scanning areas SA1 to SA2. The size of one electron beam is determined such that each primary electron beam can scan the area having a width of 50 μm. When the irradiation point of the electron beam reaches the right side in the corresponding scanning area, the irradiating point is moved back to the left side of the scanning area. On the other hand the stage device continuously moves the wafer with predetermined speed in the Y direction.

In this regard, it is required to make special arrangements in order to minimize the affection by the three aberrations, i.e., the distortion caused by the primary optical system, the axial chromatic aberration, and the filed astigmatism, when the primary electron beams passed through the apertures of the multi-aperture plate 723 in the primary optical system are focused onto the surface of the wafer W and then the secondary electrons emitted from the wafer W are formed into an image on the detector 761.

It is to be noticed that, with respect to the relationship between the spacing of a plurality of primary electron beams and the secondary optical system, any space between the primary electron beams made longer than the aberration by the secondary optical system may eliminate the cross talks among the plurality of beams.

Although there has been described above an example in which a plurality of tips of the cathode of the electron gun is arranged along a circle, the plurality of tips may be arranged on a line. In that case, the apertures formed on the first multi aperture plate 723 as well as those on the second multi aperture plate 745 must be arranged along respective lines at positions corresponding to the tips of the cathode.

According to an actual machine test having been conducted by using the electron beam apparatus shown in FIG. 8, a beam current of 3nA was obtained as a beam current for each of nine electron beams when a beam diameter of 10 nm was employed. In comparison with the beam current of 150 nA during an operation within the temperature limited region, the S/N ratio was in a comparative degree. Since a total beam current of the nine electron beams was 27 nA, which was small enough in comparison with the 150 nA, a beam blur possibly caused by the space charge effect had almost no effect. Further, because of nine electron beams being used, nine times as fast as inspection speed may be expected in comparison with a case of one electron beam.

Then, with reference to FIG. 13, a detailed configuration of the image data processing section 771 of the electron beam apparatus shown in FIG. 8 will be described. The image data processing section 771 comprises a sub-image data storage sub system 7711, an image data re-arranging sub system 7712, an inter-sub-image overlap processing sub system 7713, an inspection image data storage sub system 7714, a reference image data storage sub system 7715, and a comparison sub system 7716. The sub-image data storage sub system 7711 serves to receive and to store a sub-image data detected by each detector 761 for detecting the secondary electron, and has a storage area corresponding to each detector. The image data re-arranging sub system 7712 serves to re-arrange the sub-image data stored in the sub-image data storage sub system 7711 so as to match the X-Y coordinates of respective multi beams, while the inter-sub-image overlap processing sub system 7713 serves to determine a boundary between the sub-images and/or to decide either of the sub-image data should be employed. Re-arranged image data is stored in the inspection image data storage sub system 7714. The comparison sub system 7716 compares the image data stored in the inspection image data storage sub system 7714 with the reference image data stored in the reference image data storage sub system 7715, and outputs a result of the comparison.

Figure 13:
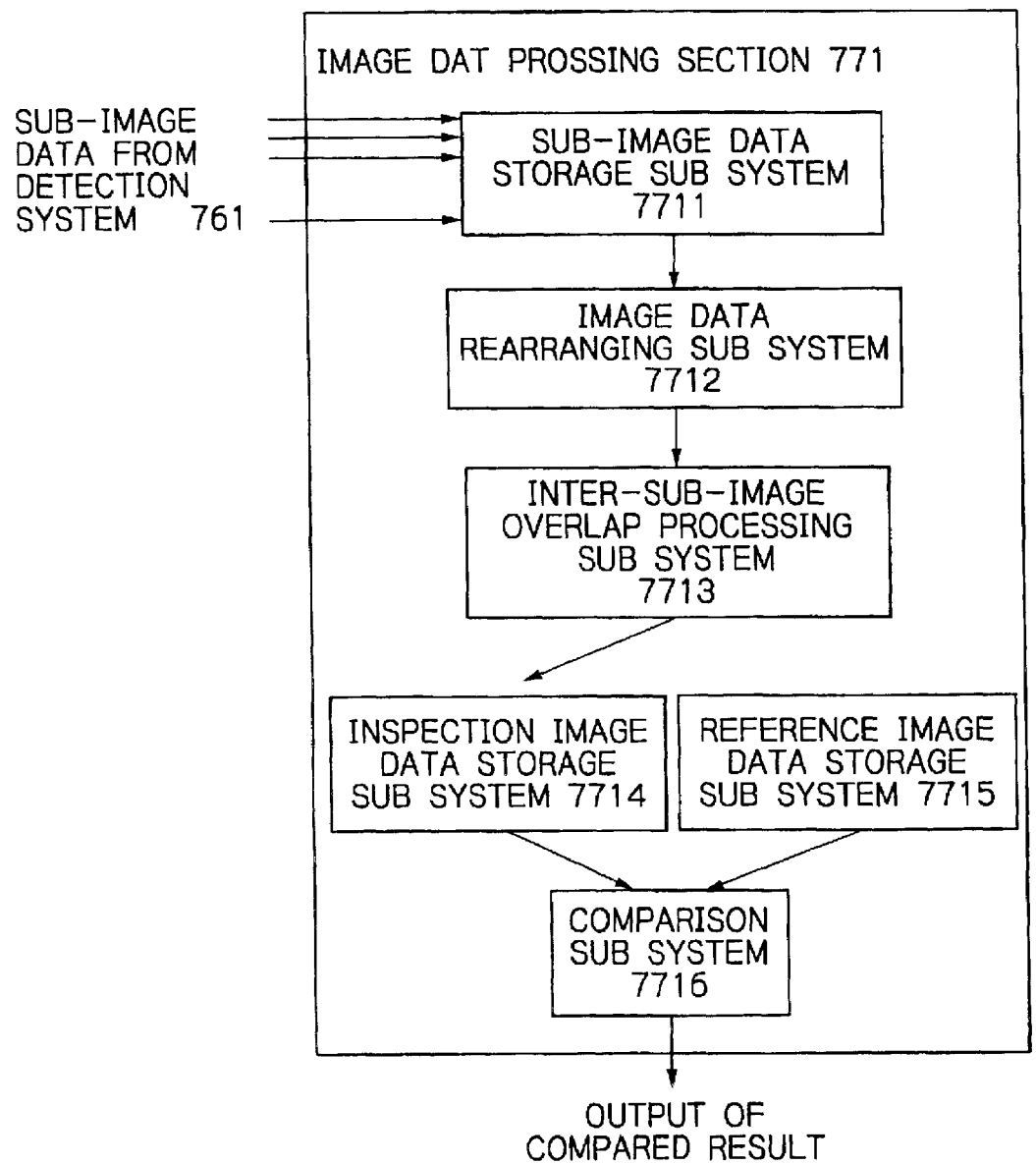
FIG. 13 is a block diagram illustrating a configuration of an image data processing section shown in FIG. 8.
Figure 14:
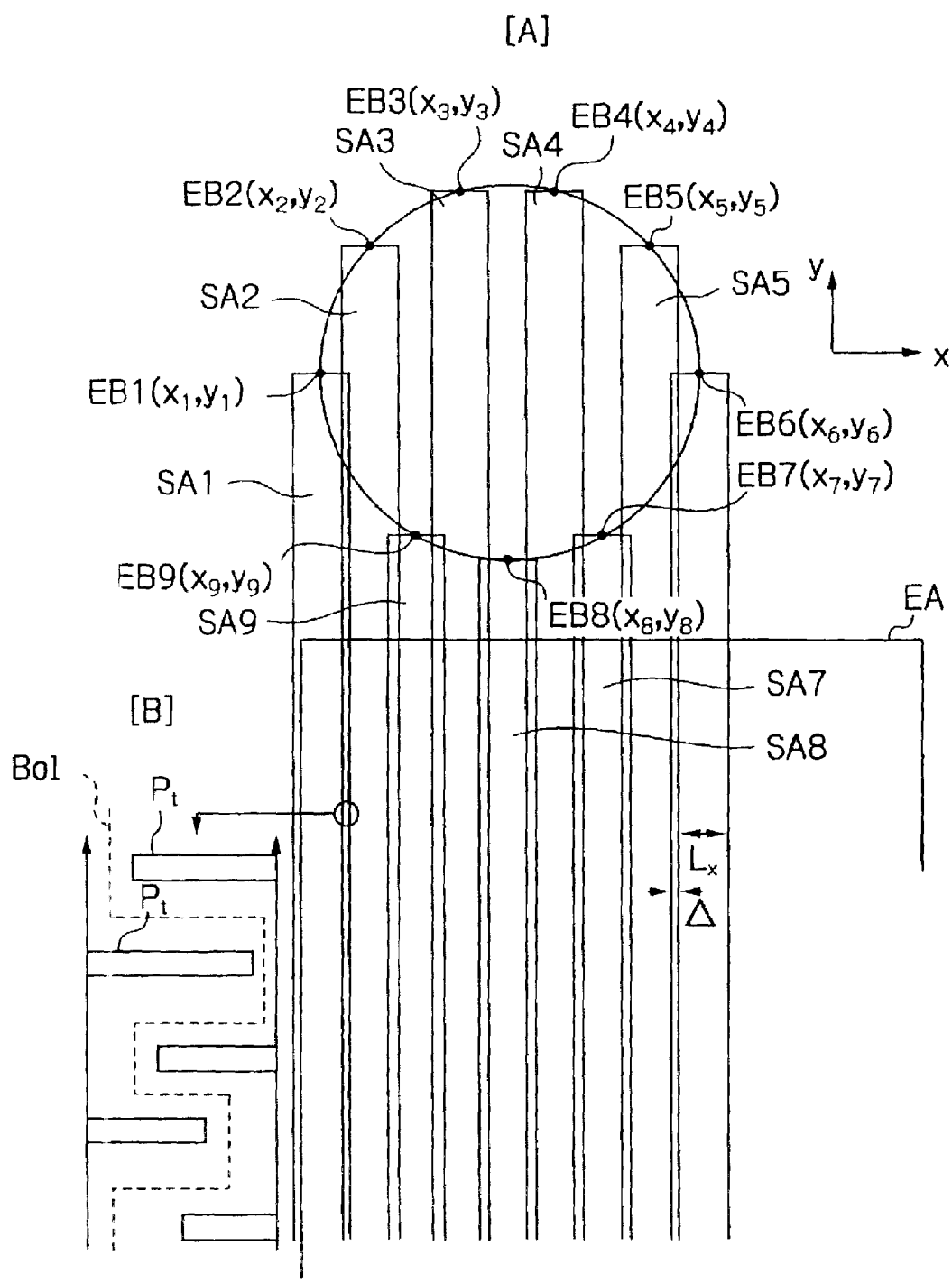
FIG. 14 illustrates an operation of an image data re-arranging device shown in FIG. 13.

FIG. 14 illustrates an operation of the image data re-arranging sub system 7712 shown in FIG. 13. As having been described with reference to FIG. 8, the first and the second multi aperture plates 723 and 745 are designed such that arrangement positions of the apertures in the first and the second multi aperture plates 723 and 745 (and the detectors 761) may relatively correspond to each other, and projected points on the X-axis of the beam spots irradiated through the apertures in the first multi aperture plate 723 onto the wafer W may be spaced with approximately equal distances. Therefore, the beam spots generated when the multi beams having passed through the plurality of apertures in the first multi aperture plate 723 are irradiated onto the wafer W are also spaced with approximately equal distances when they are projected onto the X-axis. That is, in FIG. 14, when the X-Y coordinates of the multi beams (i.e. beam spots) EB1 to EB9 formed along a circle around a center of the optical axis are designated by $(x_1, y_1) \sim (x_9, y_9)$, a relation thereof may be expressed as:

$$x_1-x_2 \approx x_2-x_9 \approx x_9-x_3 \approx x_3-x_8 \approx x_8-x_4 \approx x_4-x_7 \approx x_7-x_5 \approx x_5-x_6 \approx Lx \text{ (constant, as shown in FIG.9).}$$

When a sample or the wafer W is evaluated by using the electron beam apparatus shown in FIG. 8, the multi beams EB1 to EB 9 are simultaneously irradiated onto the wafer W while continuously moving the stage unit 50 on which the wafer W is mounted in the Y-axis direction and at the same time controlling the multi beams so as to scan in the X-direction by a line width d+Δ. That is, adjacent two beams are controlled so as for their scanning areas to overlap with each other in the X-direction by Δ. Thus, when the areas scanned by the multi beams EB1 to EB9 are designated by SA1 to SA9, the multi beams EB1 to EB9 raster-scan the corresponding areas SA1 to SA9 respectively.

The secondary electron beams emitted from a surface of the wafer W by an irradiation of the multi beams are passed through the apertures of the second multi aperture plate 745 to be detected by the corresponding detectors 761 for detecting the secondary electrons, and what are detected by the detectors 761 are stored in the respective storage areas in the sub-image data storage sub system 7711 as the sub-image data. The image re-arranging sub system 7712 re-arranges the sub-image data stored in the storage sub system 7711 so as to be arranged in a order of the detectors from 761-1 to 761-9 (wherein, the detectors 761-1 to 761-9 correspond to the multi beams EB1 to EB9 respectively), that is, in the area order of SA1, SA2, SA9, SA3, SA8, SA4, SA7, SA5, and then SA6.

At that time, the displacement of the detectors 761-1 to 761-9 in the Y-axis direction should be taken into account. For example, as to the detectors 761-1 and 761-2, time T necessary for the movement of the stage unit 50 by a distance $y_2-y_1$ is measured in advance and arranges the image data rearranging sub system 7712, adjacent to a sub-image data from the detector 761-1 obtained by a certain scanning in the X-axis direction, another sub-image data obtained from the detector 761-2 at the time T after said certain scanning. Thereby, not only an arrangement relation of the X coordinate but also the Y coordinate value of the image data adjacently arranged in the X-direction can be made coincident with each other. Alternative method may be employed in which the distance $y_2-y_1$ is converted into a number of the pixels so as to displace their position by that number of pixels.

The overlap Δ between adjacent two areas is determined by the inter-sub-image overlap processing sub system 7653, for example, in such a manner as described below. An area (B) in FIG. 14 designates the overlap between the areas SA1 and SA2, and Pt in the area (B) in FIG. 14 designates a pattern to be evaluated, wherein a boundary line Bol is determined within the overlap Δ so as not to cross the pattern such that a sub-image data from the detector 761-1 corresponding to the beam EB1 is employed for a right side area of the boundary Bol and anther sub-image data from the detector 761-2 corresponding to the beam EB2 is employed for a left side area of the boundary Bol, and then these sub-image data are combined. That is, the boundary is determined in such a manner that the crossing of the boundary between the sub-images with the patterns may be minimized. Other overlaps may be processed in the same manner.

Among these image data combined in the manner described above, only the image data within an area to be inspected EA of the wafer W are stored in the inspection image data storage sub system 7714.

When all the image data within an area to be inspected EA on the wafer W cannot be obtained by a single scanning, that is, as shown in FIG. 14, when there still exists an area to be scanned in the right side of the area SA6, the stage unit 50 may be shifted in the X-axis direction so that the new area adjacent to the area SA6 can be scanned by the beam EB1 to obtain the image data in the same manner as described above.

When any defects is to be detected, the comparison sub system 7716 compares the image data stored in the inspection image data storage sub system 7714 with the reference image data stored in the reference image data storage sub system 7715, so that the defect on the wafer W may be detected. Alternatively, a plurality of combined images for a plurality of wafer expected to have the same pattern may be obtained to compare the image data with each other, thereby determining there being the defect at a portion of a certain wafer when said portion exhibits an image data different from other most image data.

When a line width is to be detected, an appropriate method may be employed to measure the line width.

Although there has been described the case where the X coordinates of the beam spots of the primary electron beams are spaced with approximately equal distances, they may not be necessarily spaced with equal distance. Alternatively, for example, distances between beams in the X-axis direction may be measured to be converted into a number of pixels, thereby shifting the images by this number of pixels. In this case, the distance on the X coordinate between the irradiation spots may be varied.

Pre-Charge Unit

As shown in FIG. 1, a pre-charge unit 81 is disposed in a working chamber 31, adjacent to a optical column 701 of an electronic optical apparatus 70. Since this inspection apparatus is of a type in which an electron beam is irradiated a substrate or wafer to be inspected by scanning it, and thereby a device pattern or the like formed on a surface of the wafer is inspected, information such as secondary electrons emitted by the irradiation of the electron beam is utilized as an information of the wafer surface. Sometimes, depending on a condition including a material of the wafer, an energy level of the irradiated electron or the like, the wafer surface may be charged-up. Further, depending on the locations on the wafer, some locations might be more strongly charged-up than other locations. If there are non-uniform distribution in a charging amount on the wafer, the information of the secondary electron beam is made to be non-uniform, which makes it hard to obtain an accurate information.

Accordingly, in the present embodiment, there is provided a pre-charge unit 81 having a charged particle irradiating section 811 in order to prevent this non-uniform distribution. In order to prevent a non-uniform distribution in charging, before the electrons for inspection being irradiated onto a predetermined location of the wafer to be inspected, the charged particles are irradiated from the charged particle irradiating section 811 of the pre-charge unit thereto, thus preventing the non-uniform charging from occurring. The charging on the wafer surface is detected by forming and evaluating an image of the wafer surface in advance, and based on a result of the detection, the pre-charge unit 81 is operated. Further, in this pre-charge unit, the primary electron beam may be irradiated with some gradation.

In this pre-charge unit, the primary electron beam may be irradiated with an out of focus condition.

In some method for inspecting a sample for any electric defects, such a fact may be used that when a portion to be insulated is not in the insulated condition by some reason, a voltage in that portion is different from that in the insulated condition.

This is conducted in such a manner that firstly a voltage difference is generated between a voltage in a portion to be insulated essentially and that of another portion which should have been insulated but is not in the insulated condition due to some reason, by applying a charge to the sample in advance; secondly the data with voltage difference is obtained by irradiating the beam according to the present invention; and finally a non-insulated condition is detected by analyzing the obtained data.

Potential Applying Mechanism

Figure 15:
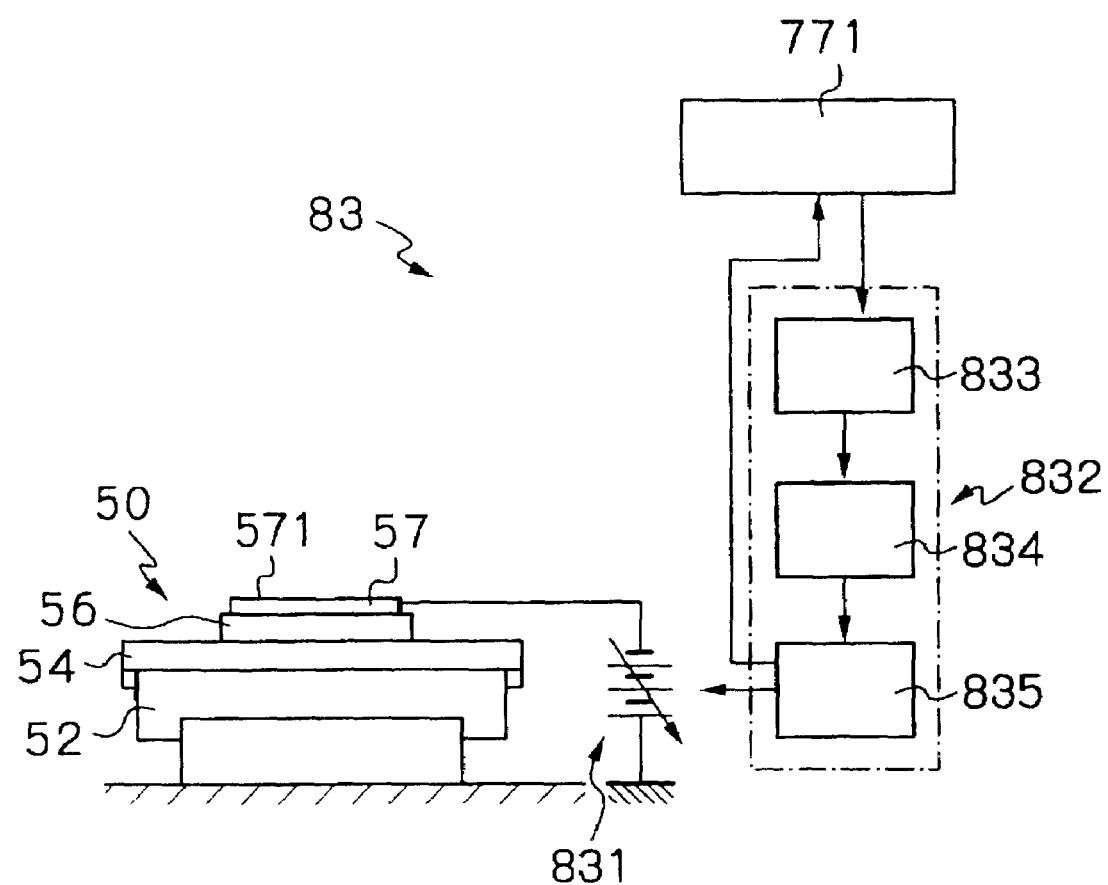
FIG. 15 shows a potential applying mechanism.

Referring next to FIG. 15, the potential applying mechanism 83 applies a potential of plus or minus several volts to a carrier of a stage, on which the wafer is placed, to control the generation of secondary electrons based on the fact that the information on the secondary electrons emitted from the wafer (secondary electron yield) depend on the potential on the wafer. The potential applying mechanism 83 also serves to decelerate the energy originally possessed by irradiated electrons to provide the wafer with irradiated electron energy of approximately 100 to 500 eV.

As illustrated in FIG. 15, the potential applying mechanism 83 comprises a voltage applying device 831 electrically connected to the carrying surface 571 of the stage device 50; and a charging detection/voltage determining system (hereinafter detection/determining system) 832. The detection/determining system 832 comprises a monitor 833 electrically connected to an image forming unit 771 of the detecting system 76 in the electron beam apparatus 70; an operator 834 connected to the monitor 833; and a CPU 835 connected to the operator 834. The CPU 835 supplies a signal to the voltage applying device 831.

The potential applying mechanism 83 is designed to find a potential at which the wafer under testing is hardly charged, and to apply such potential to the carrying surface 541.

Electron Beam Calibration Mechanism

Referring next to FIG. 16, the electron beam calibration mechanism 85 comprises a plurality of Faraday cups 851, 852 for measuring a beam current, disposed at a plurality of positions in a lateral region of the wafer carrying surface 541 on the turntable. The Faraday cups 851 are used for a fine beam (approximately Φ 2 μm), while the Faraday cups 852 are used for thick beams (approximately Φ 30 μm). The Faraday cups 851 for a fine beam measures a beam profile by driving the turntable step by step, while the Faraday cups 852 for a wide beam measure a total amount of currents. The Faraday cups 851, 852 are mounted on the wafer carrying surface 541 such that their top surfaces are coplanar with the upper surface of the wafer W carried on the carrying surface 541. In this way, the primary electron beam emitted from the electron gun is monitored at all times. This is because the electron gun cannot emit a constant electron beam at all times but varies in the emitting amount as it is used over time.

Alignment Controller

The alignment controller 87, which aligns the wafer W with the electron optical apparatus 70 using the stage system 50, performs the control for rough alignment through wide field observation using the optical microscope 871 (a measurement with a lower magnification than a measurement made by the electron optical system); high magnification alignment using the electron optical system of the electron optical apparatus 70; focus adjustment; testing region setting; pattern alignment; and so on. The wafer is tested at a low magnification using the optical system in this way because an alignment mark must be readily detected by an electron beam when the wafer is aligned by observing patterns on the wafer in a narrow field using the electron beam for automatically testing the wafer for patterns thereon.

The optical microscope 871 is disposed on the housing 30 (alternatively, may be movably disposed within the housing 30), with a light source, not shown, being additionally disposed within the housing 30 for operating the optical microscope. The electron optical system for observing the wafer at a high magnification shares the electron optical systems (primary optical system 72 and secondary optical system 74) of the electron optical apparatus 70. The configuration may be generally illustrated in FIG. 17. For observing a point to be observed on a wafer at a low magnification, the X-stage 54 of the stage device 50 is moved in the X-direction to move the point to be observed on the wafer into a view field of the optical microscope 871. The wafer is viewed in a wide field by the optical microscope 871, and the point to be observed on the wafer is displayed on a monitor 873 through a CCD 872 to roughly determine a position to be observed. In this event, the magnification of the optical microscope may be changed from a low magnification to a high magnification.

Next, the stage device 50 is moved by a distance corresponding to a spacing δx between the optical axis of the electron optical apparatus 70 and the optical axis of the optical microscope 871 to move the point to be observed on the wafer, previously determined by the optical microscope 871, to a point in the field of the electron optical apparatus 70. The distance δx between the axis $O_3$—$O_3$ of the electron optical apparatus and the axis $O_4$—$O_4$ of the optical microscope 871 is previously known (while it is assumed that the electron-optical system 70 is deviated from the optical microscope 871 in the direction along the X-axis in this embodiment, they may be deviated in the Y-axis direction as well as in the X-axis direction), such that the point to be observed can be moved to the viewing position by moving the stage device 50 by the distance δx. The point to be observed has been moved to the viewing position of the electron optical apparatus 70, the point to be observed is imaged by the electron optical system at a high magnification for storing a resulting image or displaying the image on the monitor 765 through the CCD 761.

After the point to be observed on the wafer imaged by the electron optical system at a high magnification is displayed on the monitor 765, displacement of the stage device 50 with respect to the center of rotation of the turntable 54 in the wafer rotating direction, that is displacement δθ of the stage device 50 with respect to the optical axis $O_3$—$O_3$ of the electron optical system in the wafer rotating direction are detected in a known method, and displacement of a predetermined pattern with respect to the electron optical apparatus in the X-axis and Y-axis is also detected. Then, the operation of the stage device 50 is controlled to align the wafer based on the detected values and data on a testing mark attached on the wafer or data on the shape of the patterns on the wafer which have been acquired in separation.

Control System

A control system comprises a main controller, a controlling controller, and a stage controller as main components, though not shown.

The main controller is provided with a man-machine interface through which an operator manipulates the main controller (a variety of commands/instructions, an entry of recipe and the like, direction of inspection start, switching between an automatic and a manual inspection modes, an input of all of the commands required in the manual inspection mode and so forth). In addition, the main controller also performs such jobs as: a communication with a host computer in a plant; a control of the vacuum evacuating system; a transfer of a sample such as a wafer; a control of position alignment; a transmission of commands or information to other controlling controllers or the stage controller; and a receipt of information or the like. Further, the main controller also is in charge of such functions as: an acquisition of an image signal from an optical microscope; a stage vibration compensating function for compensating for possible deterioration in image by feeding back a fluctuating signal of the stage to the electronic optical system; and an automatic focal point compensating function for detecting a displacement of a usage observation point in the Z direction (the direction along the optical axis $OA_1$ of the first optical system) and feeding it back to the electron optical system so as to automatically compensating for the focal point. The transmitting/ receiving operation of the feedback signal or the like to/from the electronic optical system as well as the transmitting/receiving operation of the signal to/from the stage are performed via the controlling controller or the stage controller respectively.

The controlling controller is mainly in charge of a control of the electron optical system (such as a control of high precision power source for the electron gun, the lenses, the aligner, the Wien filter or the like). In specific, the controlling controller performs, for example, such a control (continuous control) operation as an automatic voltage setting for respective lens systems and the aligner in response to respective operation modes, so that a constant electron current may be regularly irradiated onto the irradiation region even if the magnification is changed, and the voltage to be applied to respective lens systems, the aligner or the like may be automatically set in response to the magnification.

The stage controller is mainly in charge of a control for a movement of the stage to allow a precise movement in the X- and the Y-directions on the order of μm (with tolerance of about +/−0.5 μm). Further, in the present stage, a control in the rotational direction (θ control) is also performed with a tolerance equal to or less than about +/−0.3 seconds.

Inspection Procedure

Generally, since an inspection apparatus using an electron beam is rather expensive and also the throughput thereof is rather lower than that provided by other processing apparatuses, this type of inspection apparatus is currently applied to a wafer after an important process (for example, etching, film deposition, or CMP (chemical and mechanical polishing) planarization process) which is considered that the inspection is required most.

Figure 18:
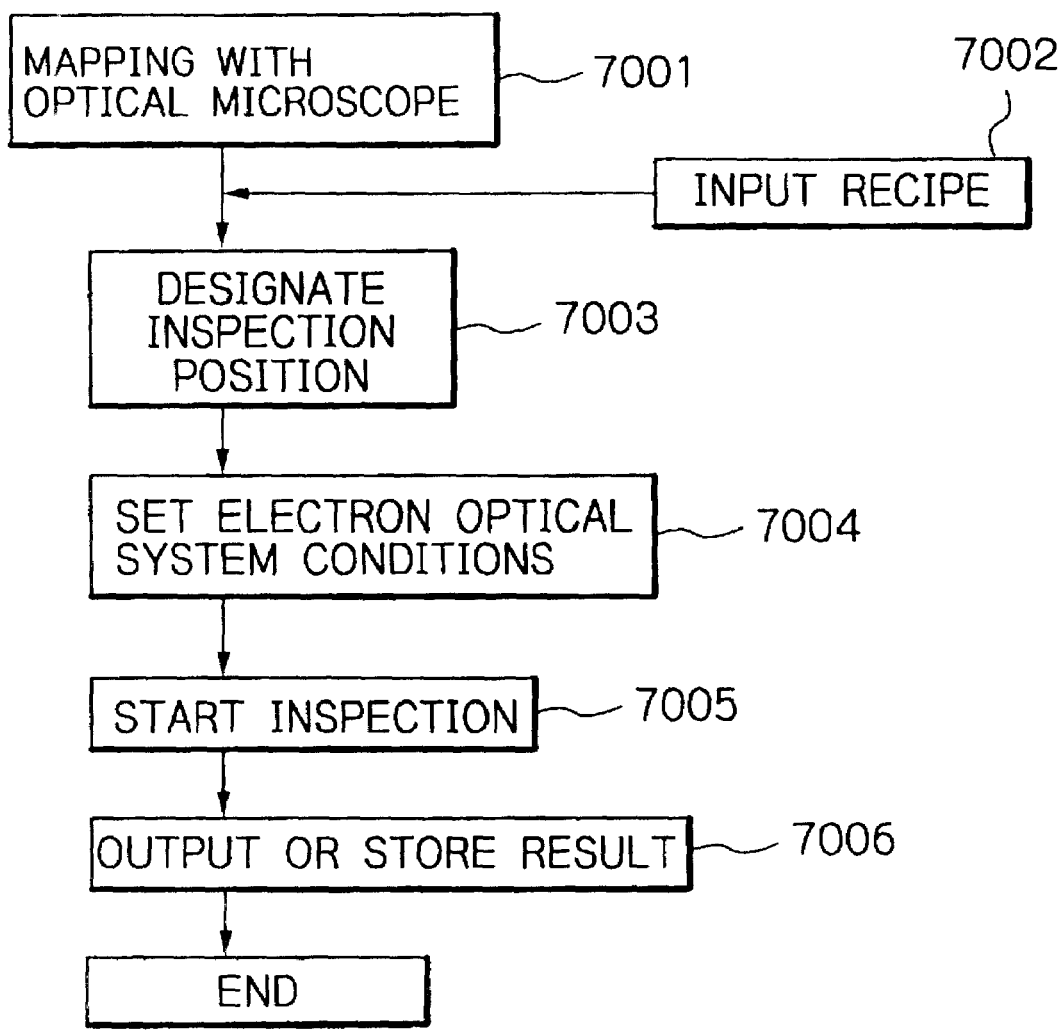
FIG. 18 is a block diagram illustrating a flow of inspection algorism.

A wafer W to be inspected is, after having been positioned on an ultra precise stage unit through a loading chamber, secured by an electrostatic chucking mechanism or the like, and then a detect inspection is conducted according to a procedure (inspection flow) shown in FIG. 18. At first, if necessary, a position of each of dice is checked and/or a height of each location is sensed, and those values are stored. Adding to that, an optical microscope is used to obtain an optical microscope image in an area to be observed possibly including defects or the like, which may also be used in, for example, the comparison with an electron beam image. Then, recipe information corresponding to the kind of the wafer (for example, after which process the inspection should be applied; which is the wafer size, 200 mm or 300 mm, and so on) is entered into the apparatus, and subsequently, after a designation of an inspection place, a setting of an electronic optical system and a setting of an inspection condition having being executed, a defect inspection is conducted typically at real time while simultaneously obtaining the image. A fast data processing system with an algorithm installed therein executes an inspection, such as the comparisons between cells, between dice or the like, and any results would be output to a CRT or the like and stored in a memory, if desired. Those defects include a particle defect, an irregular shape (a pattern defect) and an electric defect (a broken wire or via, a bad continuity or the like), and the fast data processing system also can automatically and at real-time distinguish and categorize them according to a defect size, or whether their being a killer defect (a critical defect or the like which disables a chip). The detection of the electric defect may be accomplished by detecting an irregular contrast. For example, since a location having a bad continuity would generally be charged into positive level by an electron beam irradiation (about 500 eV) and thereby its contrast would be decreased, the location of bad continuity can be distinguished from normal locations. The electron beam irradiation device in that case designates an electron beam source (source for generating thermoelectron, UV/photoelectron) with lower potential (energy) arranged in order to emphasize the contrast by a potential difference, in addition to the electron beam irradiation device used for a regular inspection. Before the electron beam for inspection being irradiated against the objective region for inspection, the electron beam having that lower potential energy is generated and irradiated.

Cleaning of Electrode

As the electron beam apparatus according to the present invention being operated for a long time, an organic substance would be deposited on a variety of electrodes used for forming or changing the electron beam. Since the insulating material gradually depositing on the surface of the electrodes by the electric charge affects reversely on the forming or deflecting mechanism for the electron beam, accordingly those deposited insulating material must be removed periodically. To remove the insulating material periodically, an electrode adjacent to the region where the insulating material has been deposited is used to generate the plasma of hydrogen, oxygen, fluorine or compound including them (HF, $O_2$, $H_2O$, $C_MF_N$ or the like) in the vacuum and to control the plasma potential in the space to be a potential level (several kV, for example, 20V-5 kV) where the spatter would be generated on the electrode surface, thereby allowing only the organic substance to be oxidized, hydrogenated or fluorinated and thereby removed.

Next, an embodiment of a method of manufacturing a semiconductor device according to the present invention will be described with reference to FIGS. 19 and 20.

Figure 19:
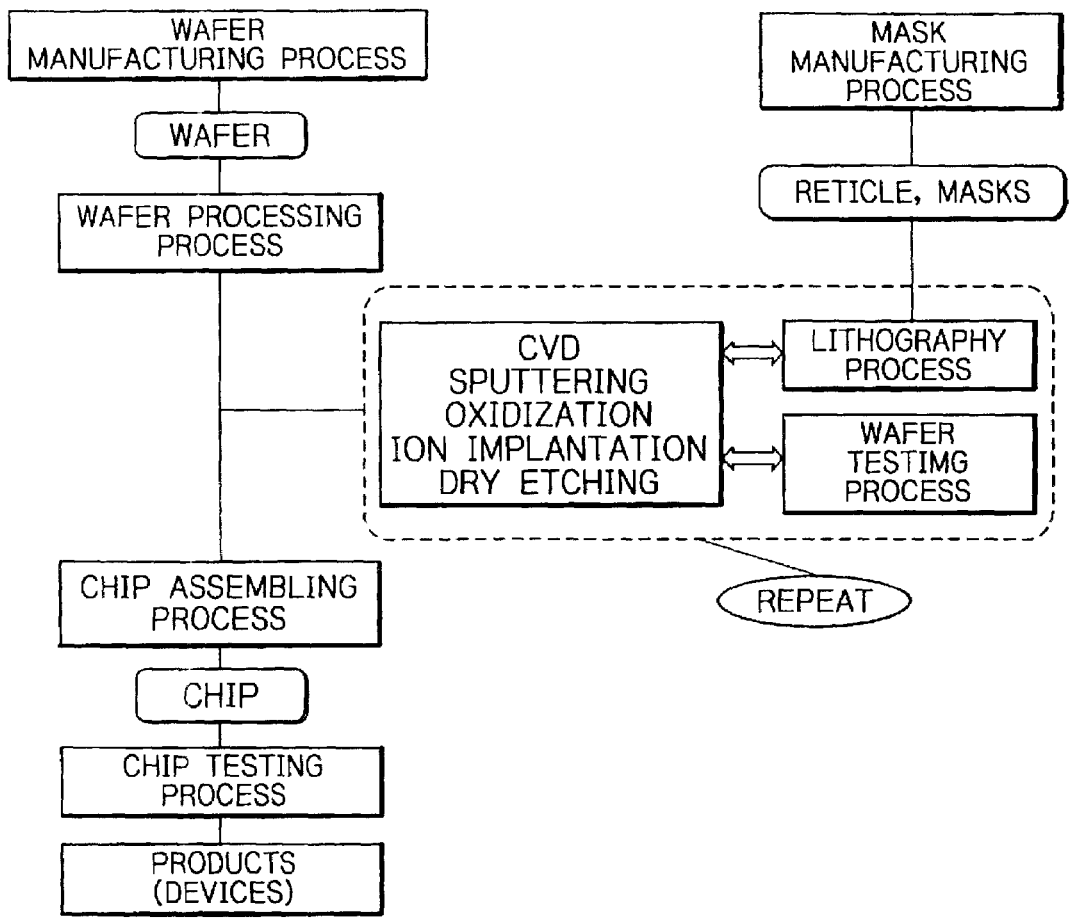
FIG. 19 is a flow chart illustrating an embodiment of a semiconductor device manufacturing method according to the present invention.

FIG. 19 is a flow chart illustrating an embodiment of a method of manufacturing a semiconductor device according to the present invention. Manufacturing processes of this embodiment include the following main processes:

(1) a wafer manufacturing process for manufacturing a wafer (or a wafer preparing process for preparing a wafer);

(2) a mask manufacturing process for manufacturing masks for use in exposure (or mask preparing process for preparing masks);

(3) a wafer processing process for performing processing required to the wafer;

(4) a chip assembling process for cutting one by one chips formed on the wafer and making them operable; and (5) a chip testing process for testing complete chips.

The respective main processes are further comprised of several sub-processes.

Among these main processes, the wafer fabricating process set forth in (3) exerts critical affections to the performance of resulting semiconductor devices. This process involves sequentially laminating designed circuit patterns on the wafer to form a large number of chips which operate as memories, MPUs and so on. The wafer fabricating process includes the following sub-processes:

(A) a thin film forming sub-process for forming dielectric thin films serving as insulating layers, metal thin films for forming wirings or electrodes, and so on (using CVD, sputtering and so on);

(B) an oxidation sub-process for oxidizing the thin film layers and the wafer substrate;

(C) a lithography sub-process for forming a resist pattern using masks (reticles) for selectively fabricating the thin film layers and the wafer substrate;

(D) an etching sub-process for fabricating the thin film layers and the substrate in conformity to the resist pattern (using, for example, dry etching techniques);

(E) an ion/impurity inplantation/diffusion subprocess;

(F) a resist striping sub-process; and (G) a sub-process for testing the fabricated wafer;

As appreciated, the wafer fabrication process is repeated a number of times equal to the number of required layers to manufacture semiconductor devices which operate as designed.

Figure 20:
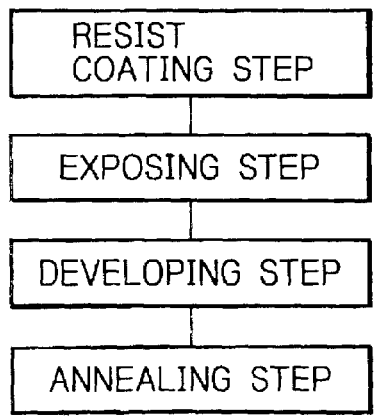
FIG. 20 is a flow chart illustrating a lithography process, a core process in a wafer processing processes of FIG. 19.

FIG. 20 is a flow chart illustrating the lithography sub-process which forms the core of the wafer processing process in FIG. 12. The lithography sub-process includes the following steps:

(a) a resist coating step for coating a resist on the wafer on which circuit patterns have been formed in the previous process;

(b) a resist exposing step;

(c) a developing step for developing the exposed resist to produce a resist pattern; and (d) an annealing step for stabilizing the developed resist pattern.

Since the aforementioned semiconductor device manufacturing process, wafer fabrication process and lithography process are well known, and therefore no further description will be required.

When the defect testing method and defect testing apparatus according to the present invention are used in the testing sub-process set forth in (G), any semiconductor devices even having submicron (sized) patterns can be tested at a high throughput, so that a total inspection can also be conducted, thereby making it possible to improve the yield rate of products and prevent defective products from being shipped.

It is to be noted that although in the above embodiment, there has been described an example shown in FIGS. 1 and 2 where only a single electron beam apparatus 70 is installed, a plurality of electron beam apparatuses may be arranged side-by-side, as shown in FIG. 21, to inspect a plurality of regions simultaneously.

Figure 21A:
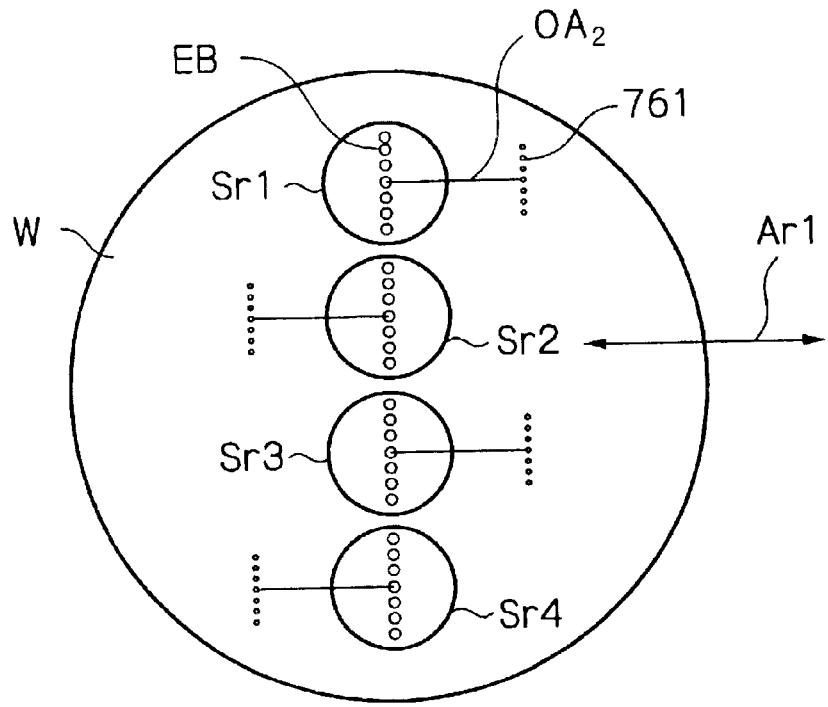
FIG. 21 illustrates an arrangement of optical columns barrels in the electron beam apparatus.
Figure 21B:
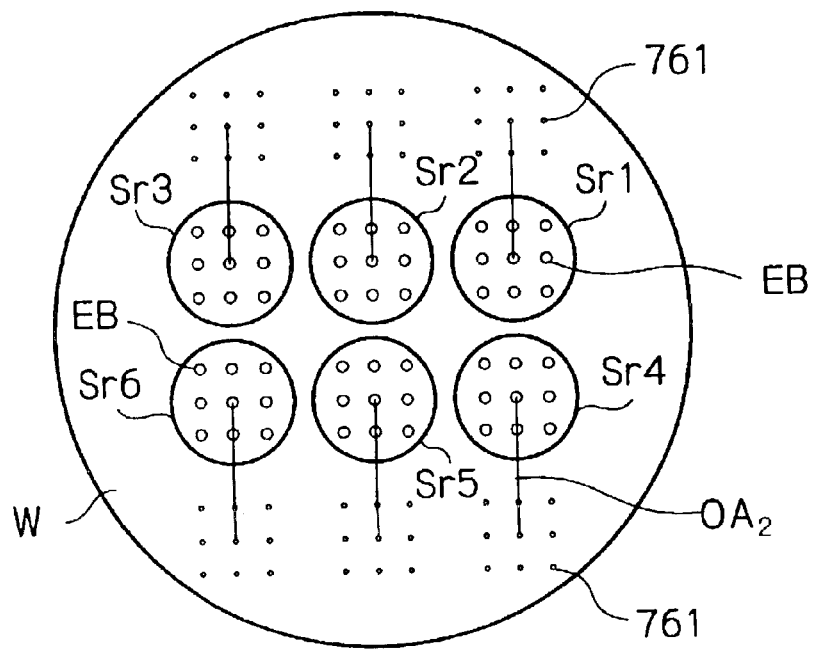

That is, FIG. 21(A) is a plan view of an example of arrangement where four optical columns (each optical column includes one electron beam apparatus respectively) are arranged on a line, while FIG. 21(B) is a plan view of another example of arrangement where six optical columns, each having an optical axis $OA_2$, are arranged in a matrix of two rows by three columns. In the examples shown in FIGS. 21(A) and 21(B), a single optical columns irradiates a plurality of electron beams (each one is designated by a symbol "EB"), which is then detected by a multi detector. The multi detector comprises a plurality of detector elements 761, each detecting a single electron beam EB. A maximum outer diameter of an area on a wafer surface irradiated by a plurality of electron beams of one optical column is designated respectively by symbols Sr1 to Sr6. In the examples shown in FIGS. 21(A) and 21(B), each of the plurality of optical columns is arranged so as not to interface with each other, so that a wide area of wafer surface may be inspected by a number of optical columns at once, thereby accomplishing high throughput in the wafer inspection process. In the example shown in FIG. 21(A), the wafer surface is continuously moved in a direction perpendicular to the row of the optical columns (designated by an arrow Ar1) in order to inspect entire wafer W.

Variation of the Inspection Apparatus

Figure 22:
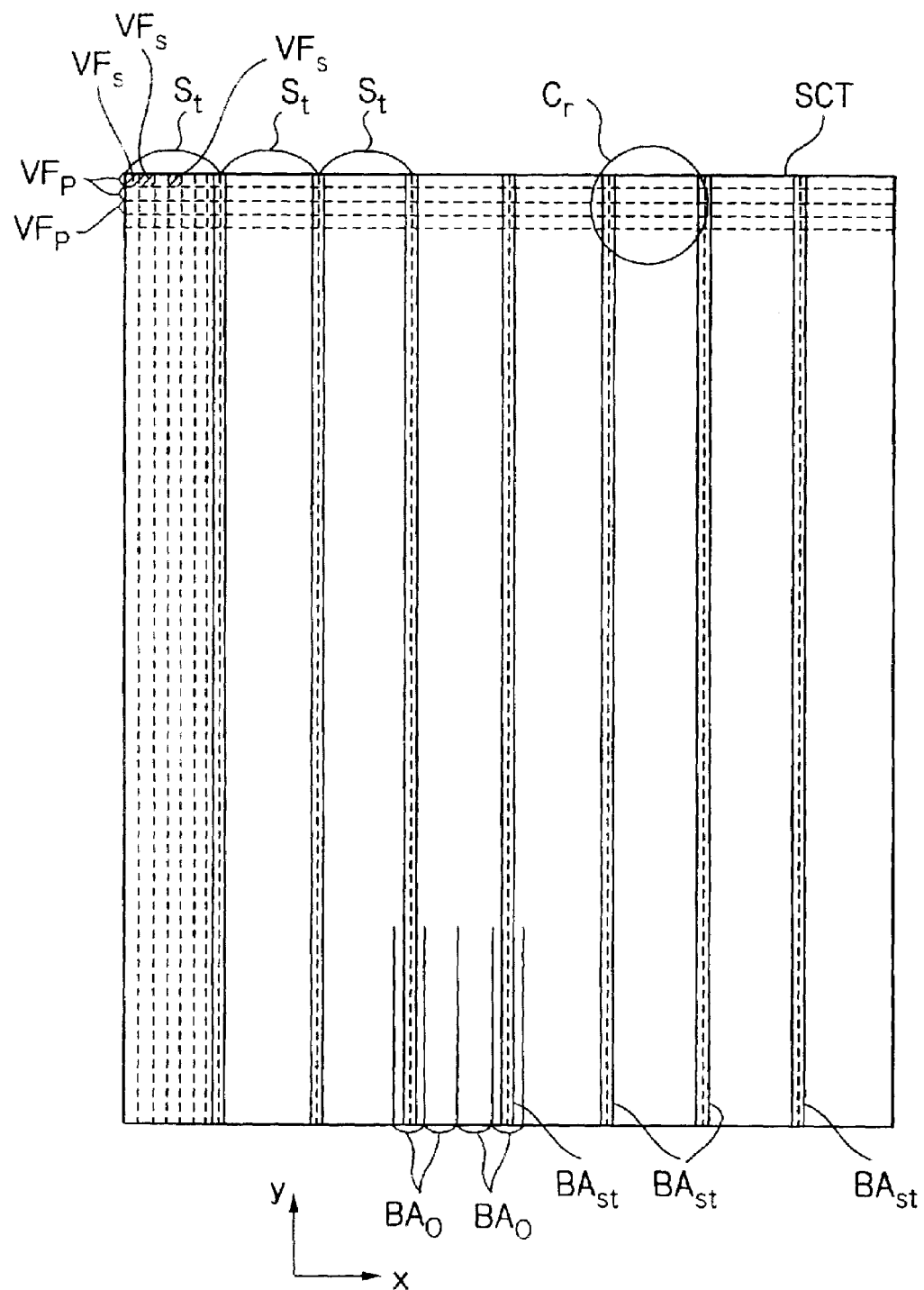
FIG. 22 illustrates an evaluation region in an alternative embodiment of the inspection method.
Figure 23:
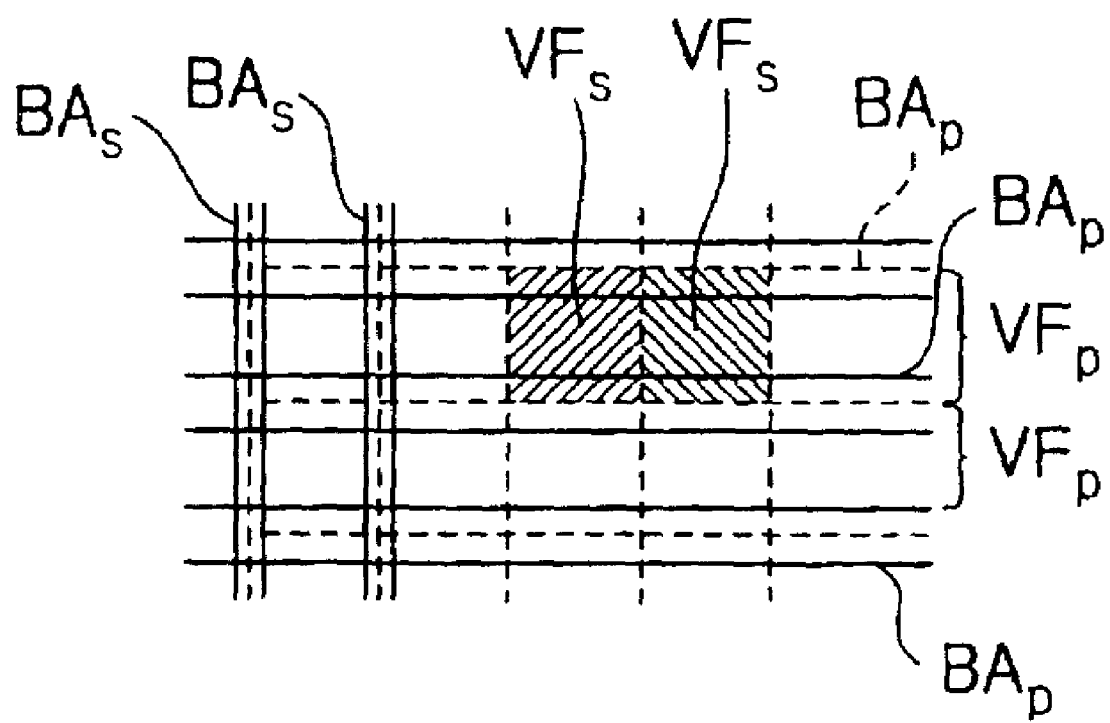
FIG. 23 is an enlarged view of an area encircled by a circle Cr of FIG. 22.

Then, a specific example of an inspection method of a circuit pattern formed on a substrate or the wafer W will be described. FIGS. 22 and 23 show typical example in the case of forming a circuit pattern by using an electron beam lithography. That is, a semiconductor chip SCT is divided into a plurality of stripes St extending in a Y-axis direction with a width in a X-direction of, for example, 5 mm, and a mask pattern is transferred onto the wafer while continuously moving the stage unit 50 with said semiconductor chip mounted thereon along each stripe in the Y-direction. Further, one stripe is divided into a plurality of primary fields of views, each being defined by a Y-direction size of 250 μm and an X-direction size of 5 mm and designated by VFp, which in turn is further divided into a plurality of secondary fields of view, each being defined by 250 μm square and designated by VFs, wherein the transfer is executed for each secondary field of view. That is, one mask is prepared for each secondary field of view, which is a component of the primary field of view, and a circuit portion is transferred by scanning with the beam each secondary field of view one-by-one.

When the circuit pattern is formed by the above-described method, a portion where the defect is most likely to occur is in a boundary between one stripe St and an adjacent stripe St, a portion where the defect is second-most likely to occur is in a boundary between the primary fields of view VFps, and a portion where the defect is third-most likely to occur is in a boundary between the secondary fields of view VFss. A portion with the widest fluctuation exhibits in the same order of boundary portion between stripes, that between the primary fields of view, and that between the secondary fields of view.

Accordingly, in this embodiment, an evaluation apparatus is equipped with an inspection mode for inspecting each boundary between the stripes designated by BAst with a width of 200 μm (seven portions in FIG. 22). When more precise evaluation is expected, a mode for inspecting a boundary area between the primary fields of view designated as BAp should be employed, and more preferably a mode for inspecting a boundary area between the secondary fields of view designated as BAs should be employed additionally. Applying a sampling inspection with a certain priority as described above allows most defects to be detected while reducing an inspection time to be several to several ten percents in comparison with the case of 100% inspection.

In the electron beam apparatus, the optical system has small aberration and distortion in a central portion of the field of view, and accordingly a reliable evaluation may be accomplished when the central portion of the field of view is used for the measurement. That is, a probability of missing any defects may be made lower when the boundary area could be necessarily evaluated by using the central portion of the field of view, as showing the stripe width by BAo, even if both of the boundary area and the other areas are to be inspected together. Moreover, a probability of detrmining normal patterns as defects may be made lower.

The deflectors for scanning 733 and 728 are adapted to scan the surface of the wafer W with the irradiation points of the primary electron beam in the X-direction, and a scanning distance is controlled to be "an X-directional distance between irradiation points of the primary electron beams plus α". That is, the α designates a dimension in the X-direction of the area to be double scanned, which is 0.3 to 3 mm.

When the boundary between the stripes on the surface of the wafer W is to be inspected in this electron beam apparatus, the stage unit 50 continuously moves the wafer in the Y-direction for the inspection. During this operation, the scanning deflectors 733 and 728 control the irradiation point of each primary electron beam to scan in the X-direction by the X-directional distance between the electron beams plus α. For example, the boundary between the stripes described above is to be inspected by a width of 200 μm, the X-directional distance between the primary electron beam irradiation points is set to be 23 μm, then each primary electron beam irradiation point scans a width of 23+α, and as a whole, an inspection width of 23×9+α (=200 μm+α) may be accomplished.

Upon executing a defect inspection, the image obtained by scanning as described above is compared with an image without defect, which has been stored previously in a memory, to detect any defective portions automatically.

Figure 24A:
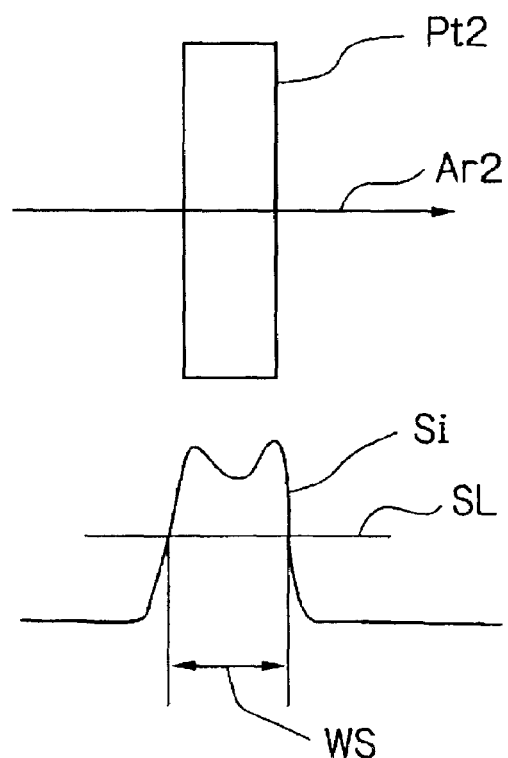
FIG. 24(A) is a diagram for illustrating a pattern line width inspection.

FIG. 24(A) shows an example for measuring a line width. An actually formed pattern Pt2 is scanned in an Ar2 direction to obtain an actual intensity signal of secondary electron Si, wherein a width ws of this signal continuously exceeding a threshold level SL determined previously through calibration may be measured as a line width of the pattern Pt2. If any line width measured in this way does not fall in a predetermined range, then this pattern may be determined to have a defect.

Figure 24B:
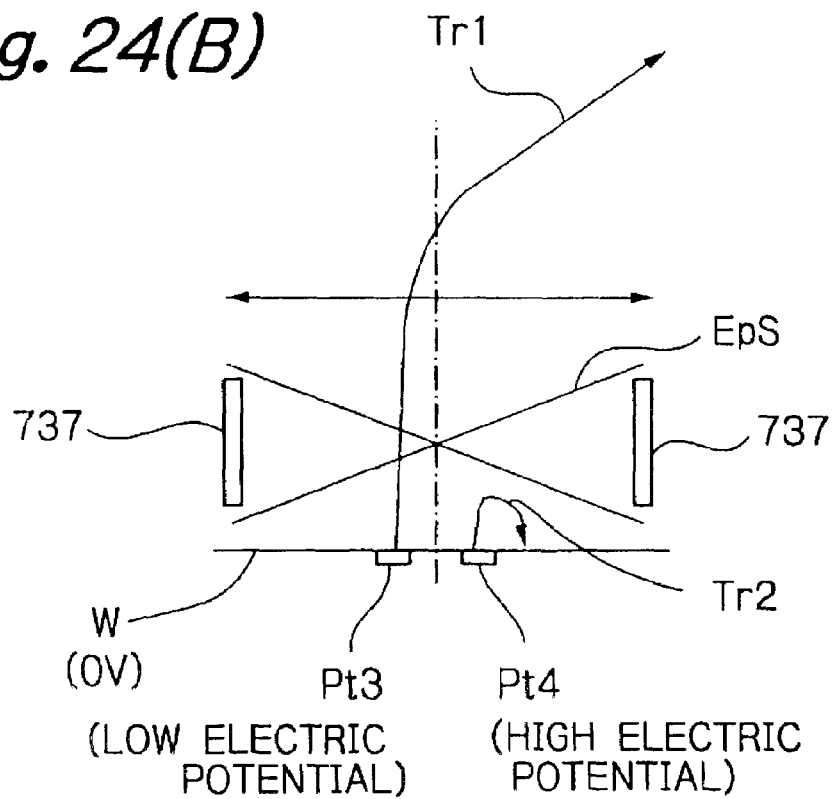
FIG. 24(B) is a diagram for illustrating a potential contrast measurement of a pattern.

FIG. 24(B) shows an example for measuring a potential contrast of a pattern formed on the wafer. In the structure shown in FIG. 8, to the axially symmetrical electrode 737 disposed between the objective lens 729 and the wafer 5 has been applied, for example, a potential of −10V relative to a wafer potential of 0V. At that time, an equipotential surface of −2V is assumed to be drawn in a shape as indicated by EpS. It is to be assumed herein that patterns Pt3 and Pt4 are at the potentials of −4V and 0V respectively. In this case, since a secondary electron emitted from the pattern Pt3 has an upward velocity equivalent to the kinetic energy of 2 eV in the −2V equipotential surface EpS, the secondary electron overcomes that potential barrier EpS and escapes from the equipotential surface Ve as indicated by an orbit Tr1, which would be detected by the detector 761. On the other hand, a secondary electron emitted from the pattern Pt4 can not overcome the potential barrier of −2V and is driven back to the wafer surface as indicated by an orbit Tr2, which would not be detected. Accordingly, a detected image for the pattern Pt3 appears to be brighter, while the detected image for the pattern Pt4 appears to be darker. Thus the potential contrast can be obtained. If the brightness and the potential for a detected image have been calibrated in advance, the potential of the pattern can be measured from the detected image. Further, based on that potential distribution, the pattern can be evaluated on any defective portions.

Each of the detectors 761 converts the detected secondary electron beam into an electric signal indicative of an intensity thereof. The electric signals thus output from respective detectors are, after having been amplified respectively by the amplifier 763, received by the image processing section 771 of the process control system 77 and converted into image data. Since the image processing section 771 is further supplied with a scanning signal for deflecting the primary electron beam, the image processing section 771 can display an image representing the surface of the wafer W. Comparing this image with the reference pattern allows any defects in the wafer W to be detected.

Further, a line width of the pattern to be evaluated on the wafer W can be measured in such a manner that firstly a pattern to be evaluated on the wafer is moved by registration to a position near to the optical axis of the primary optical system, secondly a line width evaluation signal is taken out by line-scanning and then said signal is calibrated appropriately.

Stage Unit and Variation Thereof

Referring to FIGS. 25 to 30, other embodiments of the stage unit will be described. These embodiments of the stage unit relate to an improvement of a structure using a well known hydrostatic bearing. In FIGS. 25 to 30, those components corresponding to those of the housing, the stage unit, and the electronic optical system shown in FIGS. 1 or 2 will be designated by the same reference numerals with any one of suffixes "d" to "f" added thereto. In some embodiments, common components will be designated by the same reference numerals.

Figure 25A:
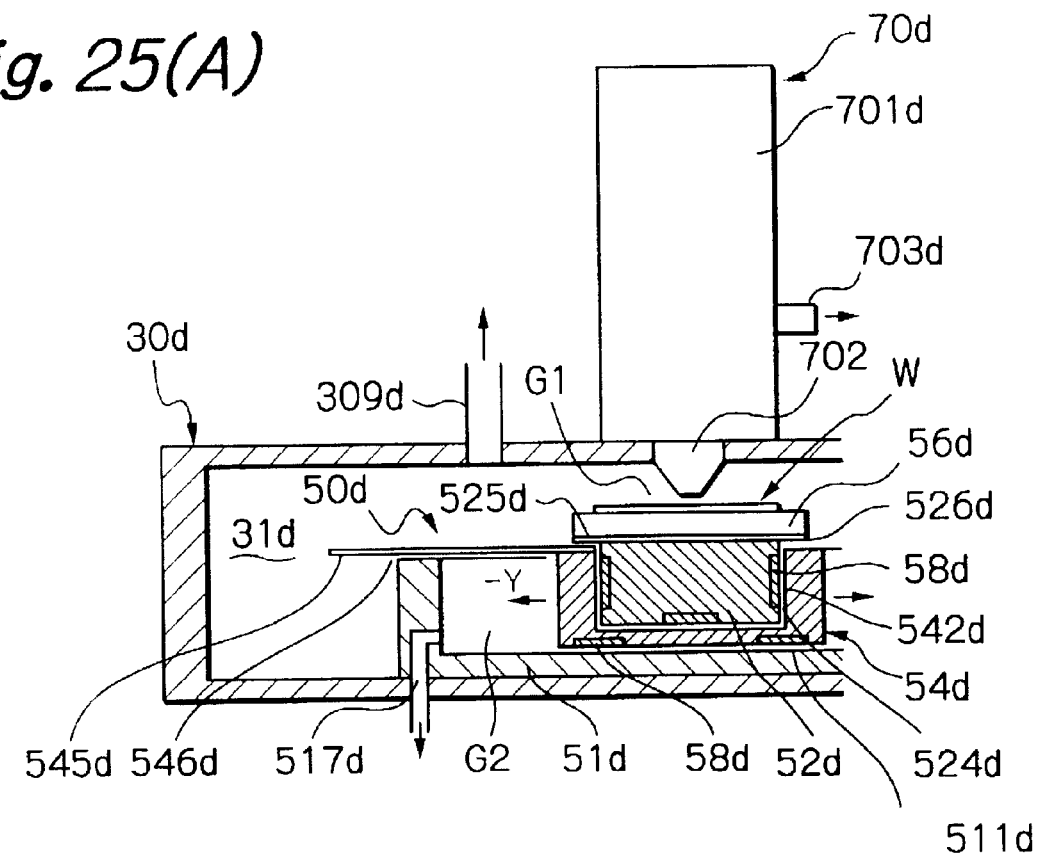
FIG. 25 shows another embodiment of a stage unit used in the substrate inspection apparatus according to the present invention, wherein (A) is an elevational view and (B) is a side elevational view.
Figure 25B:
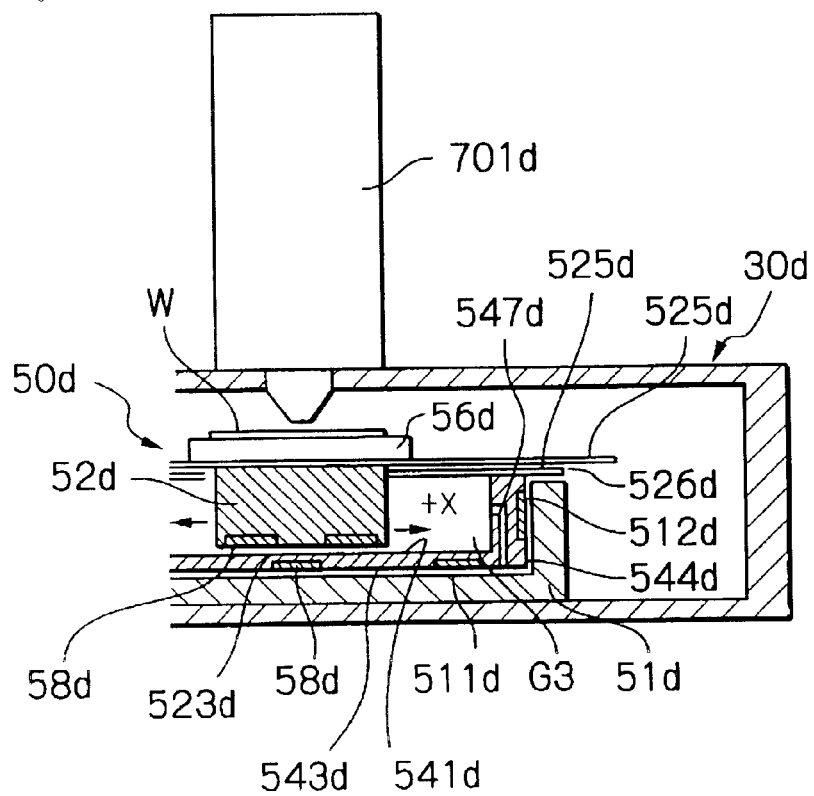
Figure 26:
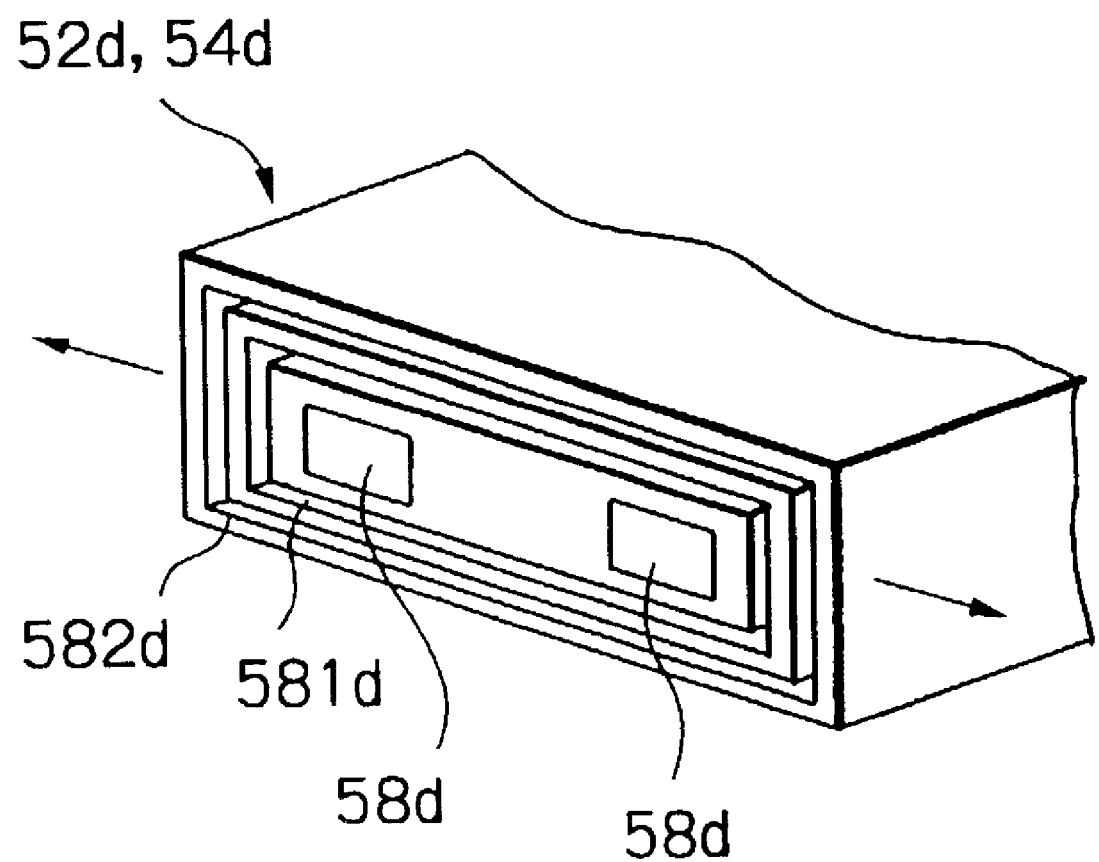
FIG. 26 is a detailed perspective view of a hydrostatic bearing section shown in FIG. 25.

Referring to FIG. 25, in a chamber 31d vacuum-exhausted via a vacuum exhaust pipe 309d, a stage unit 50d comprises: a stationary table 51d of box type (open to above) fixed to a housing 30d; an X table 54d of box type also, which is operatively mounted in said stationary table 51d so as to be movable in an X-direction (lateral direction in FIG. 25(A)); a Y-directionally movable section or a Y table 52d which is operatively mounted in said X-directionally movable section or the X table 54d so as to be movable in a Y-direction (lateral direction in FIG. 25(B)); and a turn table 56d mounted on the Y table 52d. The wafer W is detachably held by a well-known holder (not shown) installed on the turn table 56d. A bottom face 543d and a side face 544d of the X table 54d, each facing to guide faces 511d and 512d of the stationary table 51d, respectively, are provide with a plurality of hydrostatic bearings 58d, and owing to an operation of this hydrostatic bearings 58d, the X table 54d can be moved in the X-direction (lateral direction in FIG. 25(A)) while maintaining micro gap against the guide faces. Further, a bottom face 523d and a side face 524d of the Y table 52d, each facing to guide faces 541d and 542d of the X table 54d, respectively, are provide with a plurality of hydrostatic bearings 58d, and owing to the operation of this hydrostatic bearings 58d, the Y table 52d can be moved in the Y-direction (lateral direction in FIG. 25(B)) while maintaining micro gap against the guide faces. In addition, a differential pumping mechanism is arranged around the hydrostatic bearing so that a high pressure gas supplied to the hydrostatic bearing does not leak into the vacuum chamber 31d. This configuration is illustrated in FIG. 26. Around the hydrostatic bearing 58d are formed double grooves 581d and 582d 58d which are always vacuum-pumped by a vacuum pipe and a vacuum pump, though not shown. Owing to these structures, the X table is operatively supported in the vacuum in non-contact manner so as to be movable in the X-direction, and also the Y table is operatively supported in the vacuum in non-contact manner so as to be movable in the Y-direction. These double grooves 581d and 582d are formed on a surface on which the hydrostatic bearing is provided so as to surround said hydrostatic bearing. The hydrostatic bearing may be of well-known structure, and the detailed description therefor will be omitted.

A division plate 525d is attached onto an upper face of the Y table 52d of the stage unit 50d, wherein said division plate 525d overhangs to a great degree approximately horizontally in the +Y direction and the −Y direction (lateral direction in FIG. 25[B]), so that between an upper face of the X table 54d and the division plate 525d may be always provided a restrictor 526d with small conductance therebetween. Also, a similar division plate 545d is attached onto an upper face of the X table 54d so as to overhang in the +/−X direction (lateral direction in FIG. 25[A]), so that a restrictor 546d may be constantly formed between an upper face of a stationary table 51d and the division plate 545d.

In this way, since the restrictor 526d and 546d are constantly formed wherever the turn table 56d may move to, and the restrictors 526d and 546d can prevent the movement of a discharged gas even if a gas is discharged or leaked along the guide face 511d, 512d, 541d or 542d upon movement of the X table or the Y table, a pressure increase can be significantly controlled to low level in a space G1 adjacent to the wafer to which the charged particle beam is to be irradiated.

Since the grooves for differential pumping formed surrounding the hydrostatic bearings 58d work for evacuating, therefore in a case where the restrictor 526d and 546d have been formed, the discharged gas from the guiding faces is mainly evacuated by those differential pumping sections. Owing to this, the pressure in those spaces G2 and G3 within the stage are kept to be higher level than the pressure within the chamber 31d. Accordingly, if there are more portions provided for vacuum-pumping the spaces G2 and G3 in addition to the evacuating grooves 581d and 582d, the pressure within the spaces G2 and G3 can be decreased, and the pressure rise of the space G1 in the vicinity of the wafer can be controlled to be further low. For this purpose, evacuating channels 517d and 547d are provided. The evacuating channel 517d extends through the stationary table and the housing to communicate with an outside of the housing. On the other hand, the evacuating channel 547d is formed in the X table 54d and opened in an under face thereof.

It is to be noted that though arranging the division plates 545d and 525d might cause a problem requiring the chamber 31d to be extended so as not to interfere with the division plates, this can be improved by employing those division plates of stretchable material or structure. There may be suggested one embodiment in this regard, which employs the division plates made of rubber or in a form of bellows, and the ends portions thereof in the direction of movement are fixedly secured respectively, so that each end of the division plate 525d is secured to the X table 54d and that of the division plate 545d to an inner wall of the housing 30d.

Figure 27:
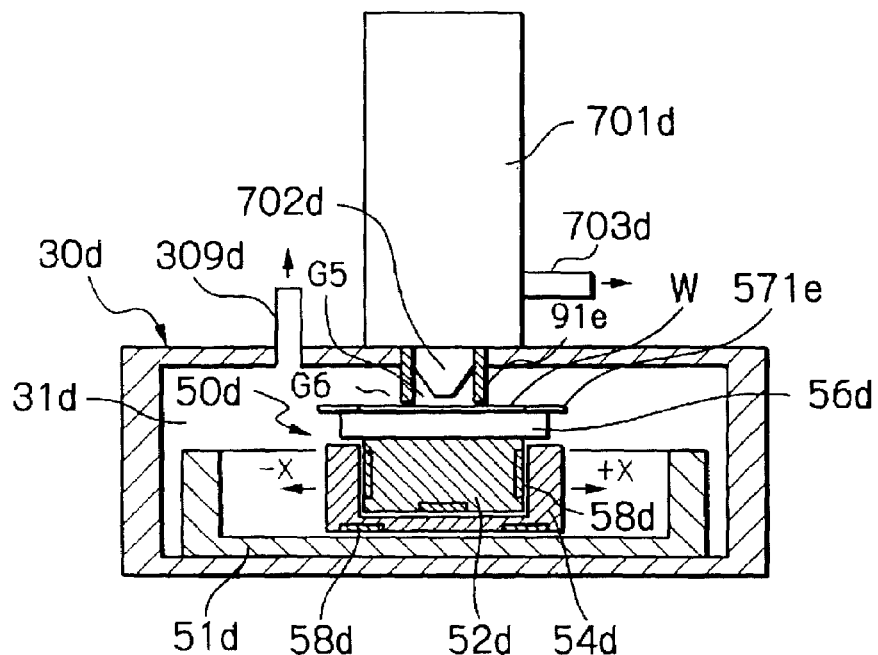
FIG. 27 shows another embodiment of a stage unit and an embodiment of evacuating system on a tip of the optical column used in the substrate inspection apparatus according to the present invention.

FIG. 27 shows another embodiment of the stage unit and other units surrounding the optical column.

In this embodiment, a cylindrical divider 91e is disposed surrounding a tip portion of an optical column 701d or an electron beam irradiating section 702d, so that a restrictor may be produced between an upper face of the wafer W and the cylindrical divider 91e. In such configuration, even if the gas is desorbed from the XY stage to increase the pressure within the chamber 31d, since a space G5 within the divider has been isolated by the divider 91e and exhausted with a vacuum pipe 703d, there could be generated a pressure deference between the pressure in the chamber 31d and that in the space G5 within the divider, thus to control the pressure rise in the space G5 within the divider to be low. Preferably, the gap between the divider 91e and the wafer surface should be approximately some ten μm to some mm, depending on the pressure levels to be maintained within the chamber 31d and in the surrounding of the irradiating section 702d. It is to be understood that the interior of the divider 91e is made to communicate with the vacuum pipe by the known method.

On the other hand, the charged particle beam irradiation apparatus or the electronic optical system may sometimes apply a high voltage of about some kV to the wafer W, and so it is feared that any conductive materials located adjacent to the wafer could cause an electric discharge. In this case, the divider 91e made of insulating material such as ceramic may be used in order to prevent any discharge between the wafer W and the divider 91e.

It is to be noted that a ring member 561e arranged so as to surround the wafer W (sample) is a plate-like adjusting part fixedly attached to a holder (not shown) mounted on the turn table 56d and is set to have the same height with the wafer so that a micro gap G6 may be formed throughout a full circle of the tip portion of the divider 91e even in a case of the charged particle beam being irradiated against an edge portion of the sample such as the wafer. Thereby, whichever location on the wafer W may be irradiated by the charged particle beam, the constant micro gap G6 can be always formed in the tip portion of the divider 91e so as to maintain the pressure stable in the space G5 surrounding the optical column tip portion.

Figure 28:
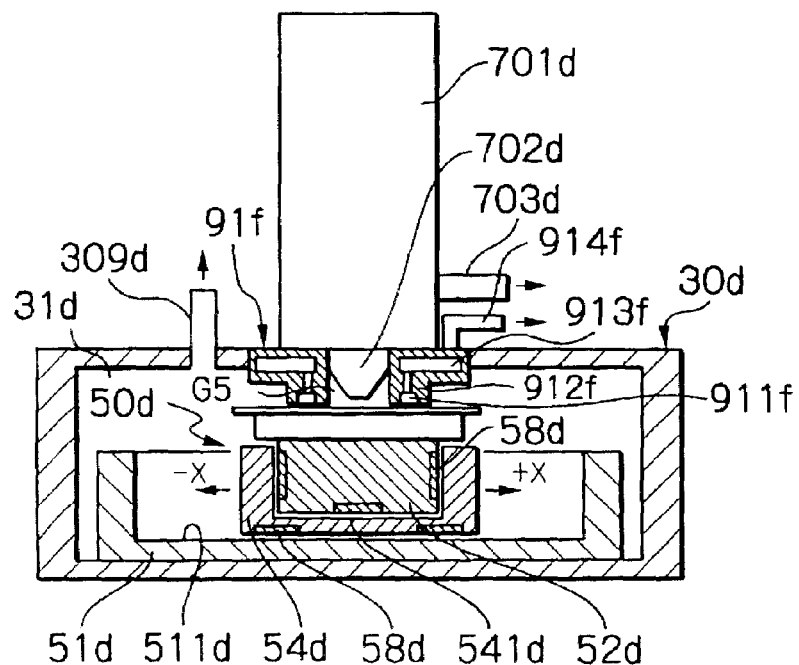
FIG. 28 shows another embodiment of the stage unit and the evacuating system on a tip of the optical column used in the substrate inspection apparatus according to the present invention.

FIG. 28 shows another embodiment in which a differential pumping system is provided on a tip portion of the optical column.

A division member 91f having a differential pumping structure integrated therein is arranged so as to surround the electron beam irradiating section 702d of the optical column 701d. The division member 91f is cylindrical in shape and has a circular channel 911f formed inside thereof and an evacuating path 912f extending upwardly from said circular channel 911f. Said evacuating path 912f is connected to a vacuum pipe 914f via an inner space 913f. A micro space as narrow as some ten μm to some mm is formed between a lower end of the division member 91f and the upper face of the Wafer W.

With such configuration as described above, even if the gas is discharged from the stage in association with the movement of the stage resulting in an increase of the pressure within the chamber 31d, and eventually is to possibly flow into the space of the tip portion or the charged particle beam irradiating section, that is, the electron beam irradiating section 702d, the gas is prevented from flowing into the electron beam irradiating section by the division member 91f, which has reduced the gap between the wafer W and itself so as to make the conductance very low, thus to reduce the flow-in rate. Further, since any gas that has flown into is allowed to be exhausted through the circular channel 911f to the vacuum pipe 914f, there will be almost no gas remained to flow into the space G5 surrounding the electron beam irradiating section 702d, and accordingly the pressure of the space surrounding the electron beam irradiating section 702d can be maintained to be a desired high vacuum level.

Figure 29:
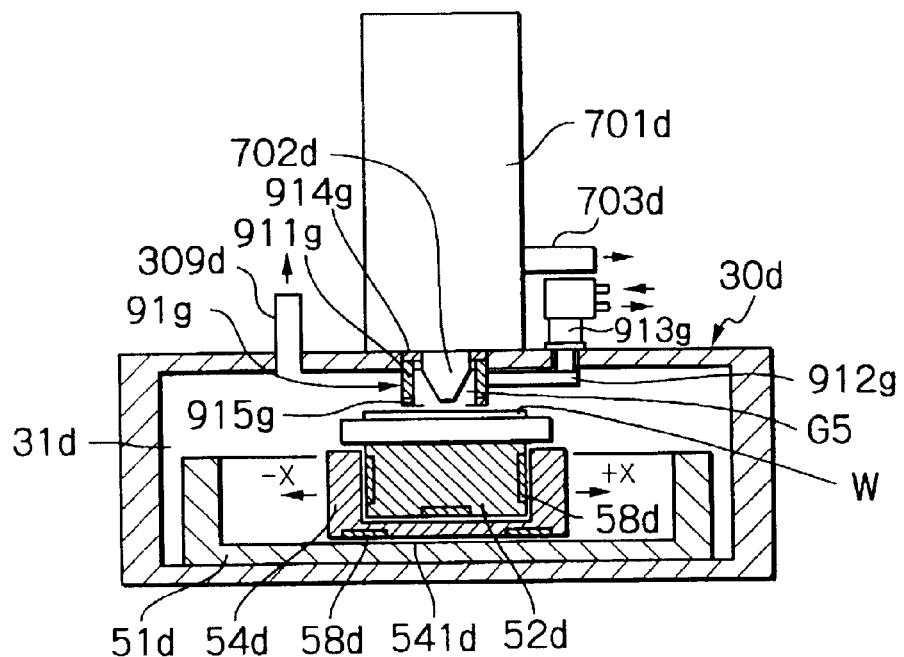
FIG. 29 shows still another embodiment of the stage unit and the evacuating system on a tip of the optical column used in the substrate inspection apparatus according to the present invention.

FIG. 29 shows still another embodiment in which a differential pumping system is provided on a tip portion of the optical column.

A division member 91g is arranged so as to surround the electron beam irradiating section 702d in the chamber 31d and accordingly to isolate the electron beam irradiating section 702d from the chamber 31d. This division member 91g is coupled at a central portion thereof 911g to a refrigerating machine 913g via a support member 912g made of material of high thermal conductivity such as copper or aluminum, and is kept as cool as −100° C. to −200° C. A part 914g of the division member 91g is provided for blocking a thermal conduction between the cooled central portion 911g and the optical column and is made of material of low thermal conductivity such as ceramic, resin or the like. Further, a part 915g of the division member 91g is made of insulating material such as ceramic or the like and is attached to the lower end of the division member 91g so as to prevent any electric discharge between the wafer W and the division member 91g.

With such configuration as described above, any gas molecules attempting to flow into the space surrounding the charged particle beam irradiating section from the chamber 31d are blocked by the division member 91g, and even if there are any molecules successfully flown into the space, they are frozen to be captured on the surface of the division member 91g, thus allowing the pressure in the space surrounding the charged particle beam irradiating section 702d to be kept low. It is to be noted that a variety type of refrigerating machines may be used for the refrigerating machine in this embodiment, for example, a cooling machine using liquid nitrogen, a He refrigerating machine, a pulse-tube type refrigerating machine or the like.

Figure 30:
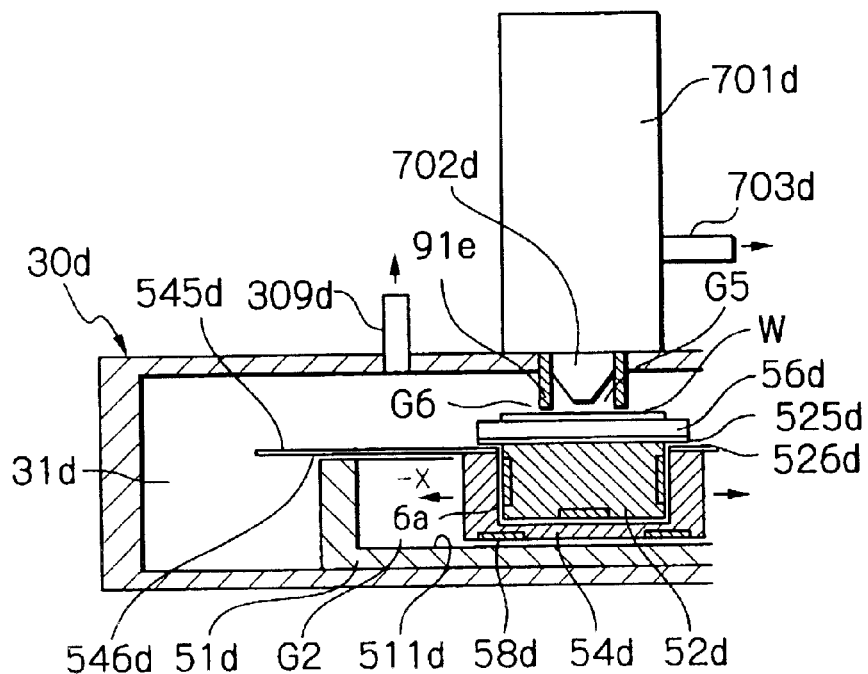
FIG. 30 shows still another embodiment of the stage unit and the evacuating system on a tip of the optical column used in the substrate inspection apparatus according to the present invention.

FIG. 30 shows still another embodiment including a variation of the stage unit and a structure of the optical column with a division member installed on a tip thereof.

The division plates 545d and 525d are respectively arranged on the X table and the Y table, similarly to those illustrated in FIG. 25, and thereby, if a holder (not shown) for holding the wafer is moved to any locations, the space G5 within the stage is separated from the inner space of the chamber 31d by those division plates via the restrictions 546d and 526d. Further, another divider 91e similar to that as illustrated in FIG. 27 is formed surrounding the electron beam irradiating section 702d so as to separate a space G5 accommodating the electron beam irradiating section 702d therein from the interior of the chamber 31d with a restriction G6 disposed therebetween. Owing to this, upon movement of the stage, even if the gas having been adsorbed onto the stage is desorbed into the space G2 to increase the pressure in this space, the pressure increase in the chamber 31d is kept to be low, and the pressure increase in the space G5 is also kept to be much lower. This allows the pressure in the space G5 for irradiating the electron beam to be maintained at low level. Alternatively, employing the division member 91f having the differential pumping mechanism integrated therein as shown in FIG. 28, or the division member 91g cooled with the refrigerating machine as shown in FIG. 29 allows the space G5 to be maintained stably with further lowered pressure.

Figure 31:
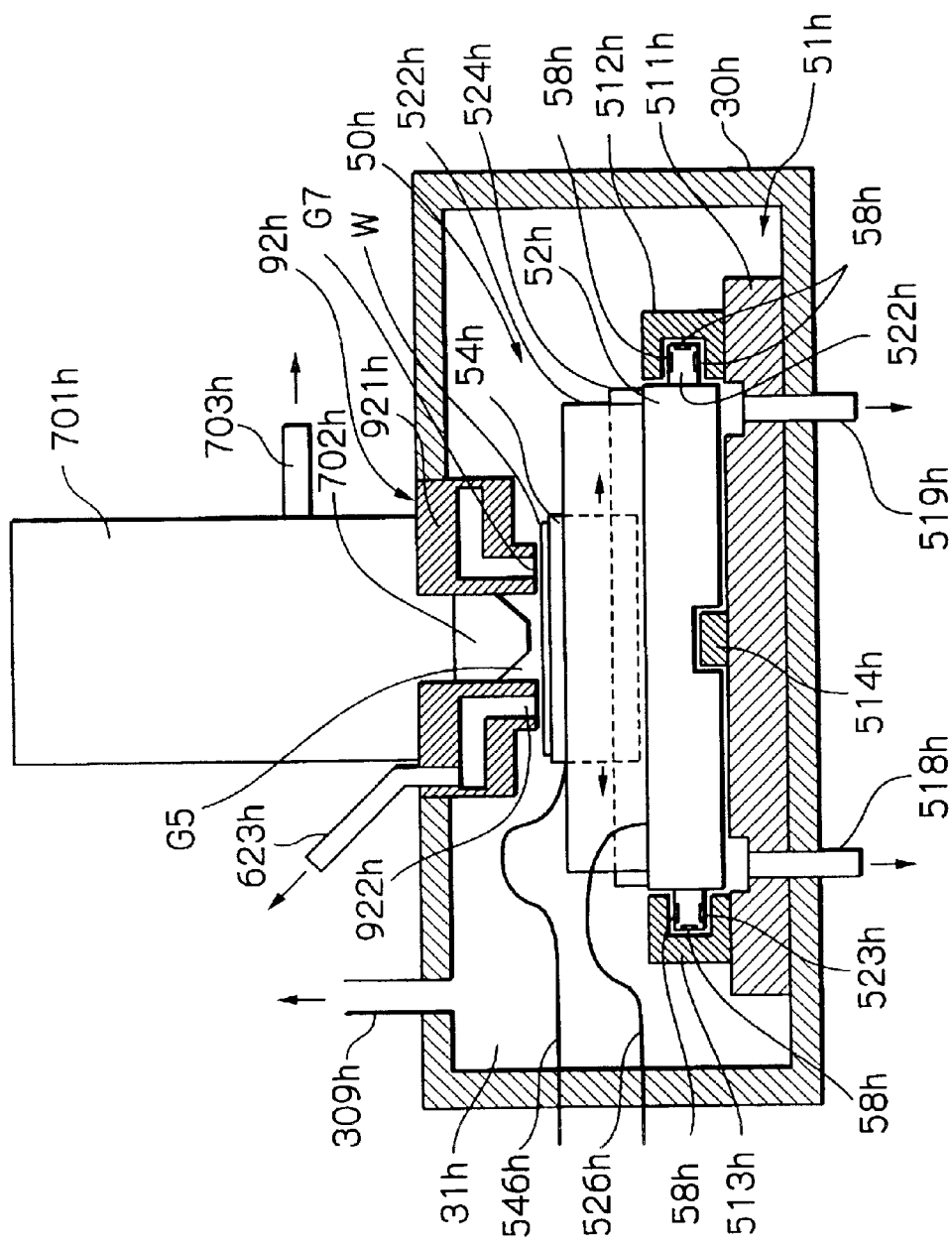
FIG. 31 shows another embodiment of a vacuum chamber and an XY stage used in the substrate inspection apparatus according to the present invention.

FIG. 31 shows still another embodiment of the stage unit and the differential pumping system. Since a general configuration of this embodiment is different from those shown in FIGS. 25 to 30, those corresponding components are designated by the same reference numerals with a suffix "h" added thereto.

A pedestal 511h of the fixed table 51h of the stage device 50h is fixedly mounted on a bottom wall of the housing 30h, and a Y table 52h movable in the Y direction (the vertical direction on paper in FIG. 31) is disposed on the pedestal 511h. Convex portions 522h and 523h are formed on opposite sides (the left and the right sides in FIG. 31) of the Y table 52h respectively, each of which projects into a concave groove formed on a side facing to the Y table in either of a pair of Y directional guides 512h and 513h mounted on the pedestal 511h. The concave groove extends approximately along the full length of the Y directional guide in the Y direction (the vertical direction on paper in FIG. 31). A top, a bottom and a side faces of respective convex portions protruding into the grooves are provided with known hydrostatic bearings 58h respectively, through which a high-pressure gas is blown out and thereby the Y table 52h is supported by the Y directional guides 512h and 513h in non-contact manner so as to be movable smoothly reciprocating in the Y direction. Further, a linear motor 514h of known structure is arranged between the pedestal 511h and the Y table 52h for driving the Y table in the Y direction. The Y table is supplied with the high-pressure gas through a flexible pipe 526h for supplying a high-pressure gas, and the high-pressure gas is further supplied to the above-described hydrostatic bearings 58h though a gas passage (not shown) formed within the Y table. The high-pressure gas supplied to the hydrostatic bearings blows out into a gap of some microns to some ten microns formed respectively between the bearings and the opposing guide planes of the Y directional guide so as to position the Y table accurately with respect to the guide planes in the X and Z directions (up and down directions in FIG. 31).

The X table 54h is disposed on the Y table so as to be movable in the X direction (the lateral direction in FIG. 31). A pair of X directional guides 522h and 523h (only 522h is illustrated) with the same structure as of the Y directional guides 512h and 513h is arranged on the Y table 52h with the X table 54h sandwiched therebetween. Concave grooves are also formed in the X directional guides on the sides facing to the X table and convex portions are formed on opposite sides of the X table (sides facing to the X directional guides). The concave groove extends approximately along the full length of the X directional guide. A top, a bottom and a side faces of respective convex portions of the X table 54h protruding into the concave grooves are provided with hydrostatic bearings (not shown) similar to those hydrostatic bearings 58h in the similar arrangements. A linear motor 524h of known configuration is disposed between the Y table 52h and the X table 54h so as to drive the X table in the X direction. Further, the X table 54h is supplied with a high-pressure gas through a flexible pipe 546h, and thus the high-pressure gas is supplied to the hydrostatic bearings. The X table 54h is supported highly precisely with respect to the Y directional guide in a non-contact manner by way of said high-pressure gas blowing out from the hydrostatic bearings to the guide planes of the X directional guides. The vacuum chamber 31h is evacuated through vacuum pipes 309h, 518h and 519h coupled to a vacuum pump of known structure. Those pipes 518h and 519h pass through the fixed table 51h to the top surface thereof to open their inlet sides (inner side of the vacuum chamber) in the proximity of the locations to which the high-pressure gas is ejected from the stage device, so that the pressure in the vacuum chamber may be prevented to the utmost from rising up by the blown-out gas from the hydrostatic bearings.

A differential pumping mechanism 92h is arranged so as to surround the tip portion of the optical column 701h or the charged particles beam irradiating section 702h, so that the pressure in a charged particles beam irradiation space G5 can be controlled to be sufficiently low even if there exists high pressure in the vacuum chamber 31h. That is, an annular member 921h of the differential pumping mechanism 92h mounted around the charged particle beam irradiating section 702h is positioned with respect to the housing 30h so that a micro gap (in a range of some microns to some-hundred microns) G7 can be formed between the lower face thereof (the surface facing to the wafer) and the wafer, and an annular groove 922h is formed in the lower face thereof. The annular groove 922h is coupled to a vacuum pump or the like, though not shown, through an evacuating pipe 923h. Accordingly, the micro gap g5 can be exhausted through the annular groove 922h and the evacuating pipe 923h, and if any gaseous molecules from the chamber 31h attempt to enter the space G5 circumscribed by the annular member 921h, they may be exhausted. Thereby, the pressure within the charged particle beam irradiation space G5 can be maintained to be low and thus the charged particle beam can be irradiated without any troubles. The annular groove 922h may be made doubled or tripled, depending on the pressure in the chamber and the pressure within the charged particle beam irradiation space G5.

Typically, dry nitrogen is used as the high-pressure gas to be supplied to the hydrostatic bearings. If available, however, a much higher-purity inert gas should be preferably used instead. This is because any impurities, such as water contents, oil and fat contents or the like, included in the gas could stick on the inner surface of the housing defining the vacuum chamber or on the surfaces of the stage components leading to the deterioration in vacuum level, or could stick on the sample surface leading to the deterioration in vacuum level in the charged particle beam irradiation space.

It should be appreciated that though typically the wafer is not placed directly on the X table, but may be placed on a sample table having a function to detachably carry the sample and/or a function to make a fine tuning of the position of the sample relative to the stage device 50, an explanation therefor is omitted in the above description for simplicity due to the reason that the presence and structure of the sample table has no concern with the principal concept of the present invention.

Since a stage mechanism of a hydrostatic bearing used in the atmospheric pressure can be used in the above-described charged particle beam apparatus mostly as it is, a high precision stage having an equivalent level of precision to those of the stage of high-precision adapted to be used in the atmospheric pressure, which is typically used in an exposing apparatus or the likes, may be accomplished for an XY stage to be used in a charged particle beam apparatus with equivalent cost and size.

It should be also appreciated that in the above description, the structure and arrangement of the hydrostatic guide and the actuator (the linear motor) have been explained only as an example, and any hydrostatic guides and actuators usable in the atmospheric pressure may be applicable.

Figure 32:
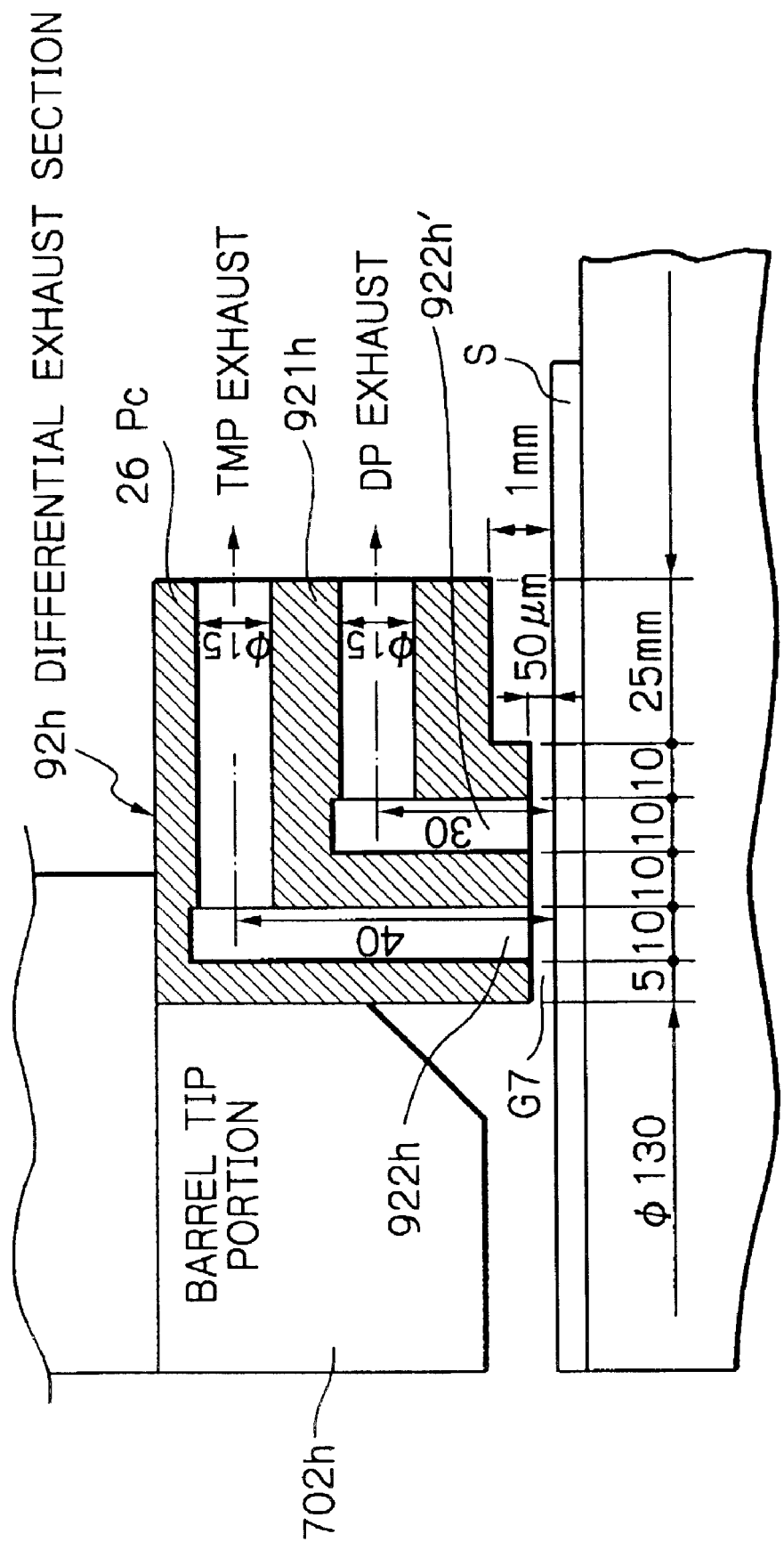
FIG. 32 shows an example of a differential pumping mechanism installed in the system shown in FIG. 31.

FIG. 32 shows an example of numeric values representative of the dimensions of the annular grooves 922 formed in the annular member 921 of the differential pumping mechanism. In this example, a doubled structure of annular grooves 922h and 922h' which are separated from each other in the radial direction is provided.

The flow rate of the high-pressure gas supplied to the hydrostatic bearing is typically in the order of about 20 L/min (in the conversion into the atmospheric pressure). Assuming that the vacuum chamber C is evacuated by a dry pump having a function of pumping speed of 20000 L/min through a vacuum pipe with an inner diameter of 50 mm and a length of 2 m, the pressure in the vacuum chamber will be about 160 Pa (about 1.2 Torr). At that time, with the applied size of the annular member 921h, the annular groove and others of the differential pumping mechanism as illustrated in FIG. 32, the pressure within the charged particles beam irradiation space G5 can be controlled to be $10^{-4}$ Pa ($10^{-6}$ Torr).

Figure 33:
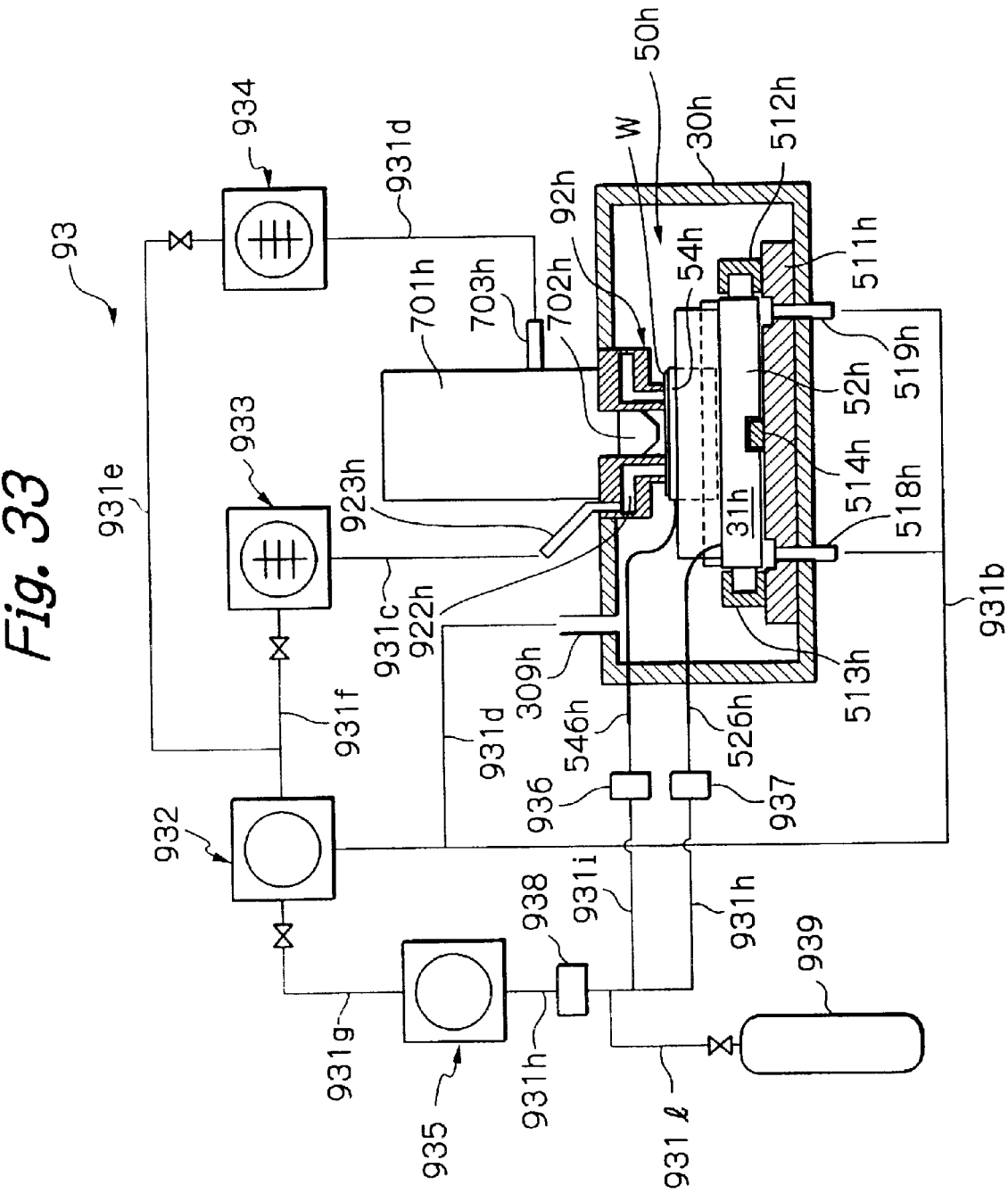
FIG. 33 shows a circulation piping system of gas for the system shown in FIG. 31.
Figure 34:
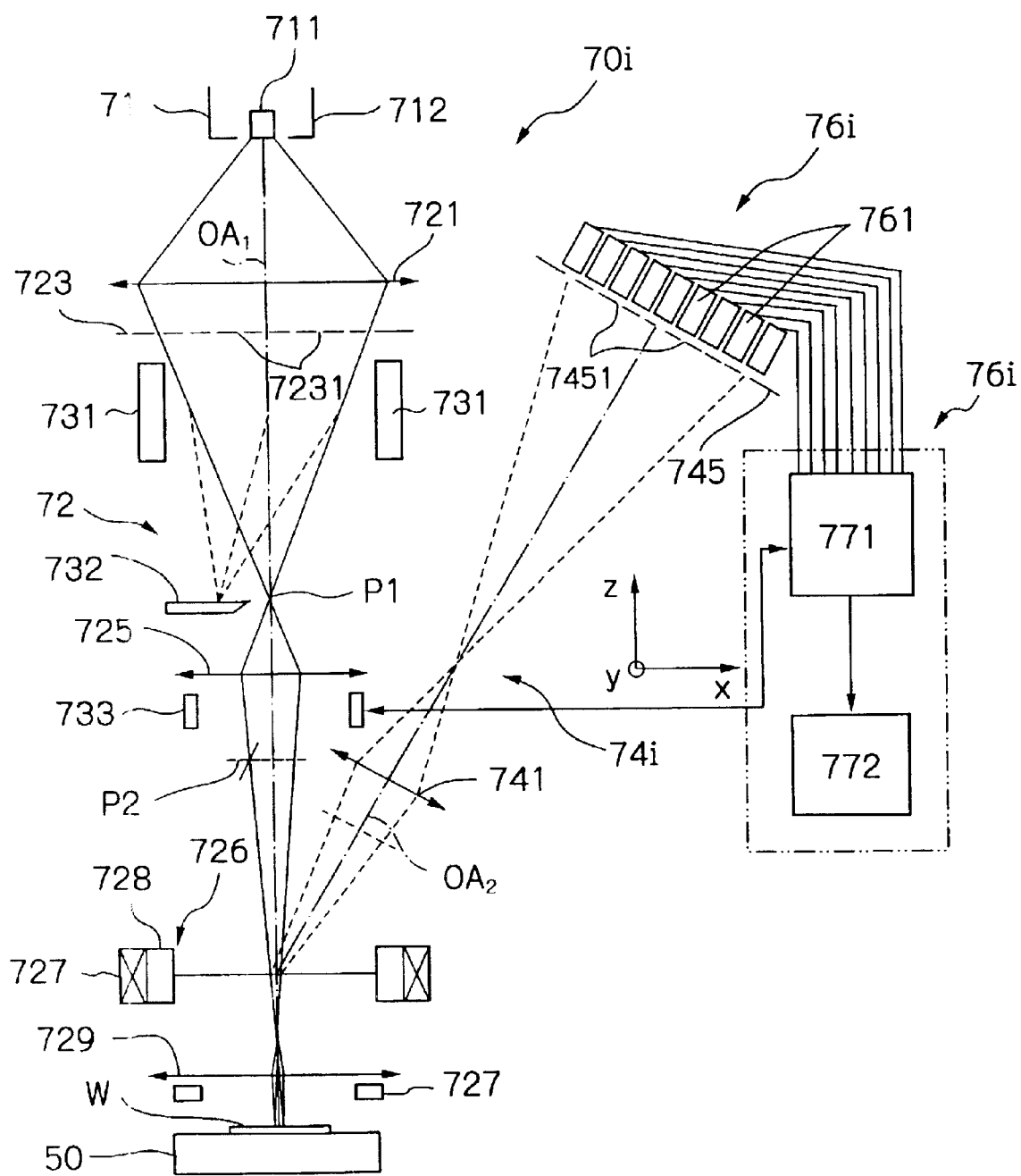
FIG. 34 is a diagram illustrating a general configuration of another embodiment of the electron beam apparatus according to the present invention.

FIG. 33 shows a vacuum chamber 31h defined by the housing 30h and a evacuating circuit 93 for the differential pumping mechanism. The vacuum chamber 31h is connected to a dry vacuum pump 932 via vacuum pipes 931a and 931b of the evacuating circuit 93. An annular groove 922h of a differential pumping mechanism 92h is connected with an ultra-high vacuum pump or a turbo molecular pump 933 via a vacuum pipe 931c connected to an exhaust port 923h. Further, the interior of a optical column 701h is connected with a turbo molecular pump 934 via a vacuum pipe 931d connected to an exhaust port 903. Those turbo molecular pumps 933, 934 are connected to the dry vacuum pump 932 through vacuum pipes 931e, 931f. (In FIG. 33, the single dry vacuum pump has been used to serve both as a roughing vacuum pump of the turbo molecular pump and as a pump for vacuum pumping of the vacuum chamber, but alternatively multiple dry vacuum pumps of separate systems may be employed for pumping, depending on the flow rate of the high-pressure gas supplied to the hydrostatic bearings of the XY stage, the volume and inner surface area of the vacuum chamber and the inner diameter and length of the vacuum pipes.)

A high-purity inert gas ($N_2$ gas, Ar gas or the like) is supplied to a hydrostatic bearing of the stage device 50h through flexible pipes 526h, 546h. Those gaseous molecules blown out of the hydrostatic bearing are diffused into the vacuum chamber and evacuated by the dry vacuum pump 932 through exhaust ports 309h, 518h and 519h. Further, those gaseous molecules having flown into the differential pumping mechanism and/or the charged particles beam irradiation space are sucked from the annular groove 922h or the tip portion of the optical column 701h and exhausted through the exhaust ports 923h and 703h by the turbo molecular pumps 933 and 934, and then those gaseous molecules, after having been exhausted by the turbo molecular pumps, are further exhausted by the dry vacuum pump 932. In this way, the high-purity inert gas supplied to the hydrostatic bearing is collected into the dry vacuum pump and then exhausted away.

On the other hand, the exhaust port of the dry vacuum pump 932 is connected to a compressor 935 via a pipe 931g, and an exhaust port of the compressor 935 is connected to flexible pipes 546h and 526h via pipes 931h, 931i and 931k and regulators 936 and 937. With this structure, the high-purity inert gas exhausted from the dry vacuum pump 932 is compressed again by the compressor 935 and then the gas, after being regulated to an appropriate pressure by regulators 936 and 937, is supplied again to the hydrostatic bearings of the stage device.

In this regard, since the gas to be supplied to the hydrostatic bearings is required to be as highly purified as possible in order not to have any water contents or oil and fat contents included therein, as described above, the turbo molecular pump, the dry pump and the compressor are all required to have such structures that they prevent any water contents or oil and fat contents from entering the gas flow path. It is also considered effective that a cold trap, a filter 938 or the like is provided in the course of the outlet side piping 931h of the compressor so as to trap the impurities such as water contents or oil and fat contents, if any, included in the circulating gas and to prevent them from being supplied to the hydrostatic bearings.

This may allow the high purity inert gas to be circulated and reused, and thus allows the high-purity inert gas to be saved, while the inert gas would not remain desorbed into a room where the present apparatus is installed, thereby eliminating a fear that any accidents such as suffocation or the like would be caused by the inert gas.

A circulation piping system is connected to a high-purity inert gas supply source 939, which serves both to fill up with the high-purity inert gas all of the circulation systems including the vacuum chamber C, the vacuum pipes 931a to 931e, and the pipes in compression side 931f to 931l, prior to the starting of the gas circulation, and to supply a deficiency of gas if the flow rate of the circulation gas decreases by some reason. Further, if the dry vacuum pump 932 is further provided with a function for compressing up to the atmospheric pressure or more, it may be employed as a single pump so as to serve both as the dry vacuum pump 932 and the compressor 935.

As the ultra-high vacuum pump to be used for evacuating the optical column, other pumps including an ion pump and a getter pump may be used instead of the turbo molecular pump. It should be appreciated that if these pumps of an accumulating type is used, a circulating piping system may not be provided for the optical column. Further, instead of the dry vacuum pump, a dry pump of other type, for example, a dry pump of diaphragm type may be used.

Alternative Embodiment of Electron Beam Apparatus

FIGS. 34 to 37 show an alternative embodiment of the electron optical apparatus or the electron beam apparatus designated generally by reference numeral 70i. In these drawings, the same components as those in the electron beam apparatus shown in FIG. 8 are designated respectively by the same reference numerals and detailed explanations on the structure and function thereof will be omitted. Besides, components different from those in FIG. 8 are designated respectively by the same reference numerals, each added with a suffix "i". Further, in the following description of each of the embodiments for the case with a multi-aperture plate included in a first and a second optical systems, since the relationship between the first and the second multi-aperture plates is same as that illustrated in FIG. 9, therefore an illustration and an explanation therefor will be omitted.

In the present embodiment, a configuration of an electron beam apparatus is same as that of the electronic optical apparatus shown in FIG. 8, with the exception that a secondary optical system thereof 74i only has a single lens and that a detection system thereof 76i comprises a pattern memory 772 connected to an image data processing section 771 of a process control system 77i.

In this apparatus, secondary electron images are detected by a set of detectors 761 of the detection system 76i disposed behind apertures 7451 of a multi-aperture plate 745 of the secondary optical system 74i without any cross talks with respect to one another, and then formed into images in the image data processing section 771 that is an image forming unit. Further, an image for a sample pattern is formed from pattern data and is stored separately in the pattern memory 772, and thereby an image comparing circuit attached to the image data processing section 771 makes a comparison of the pattern image with an image formed from the secondary electron images to classify a defect into any one of a classification group consisting of short-circuit, disconnection, convex, chipping, pinhole and isolation.

Further, upon measuring a potential of a pattern on a wafer W, a potential lower than that in a surface of the wafer is applied to an axially symmetric electrode 737 to select the secondary electrons from the sample or wafer W based on their energies such that some are permitted to pass through to an objective lens 729 side and some are driven back onto the wafer W side thus to measure a voltage of the pattern. This allows more secondary electrons originated from a pattern having a lower potential to be detected and fewer secondary electrons originated from a pattern having a higher potential to be detected, and thereby allows the potential of the pattern on the sample to be measured based on a quantity of the detected secondary electrons being large or small.

Figure 35:
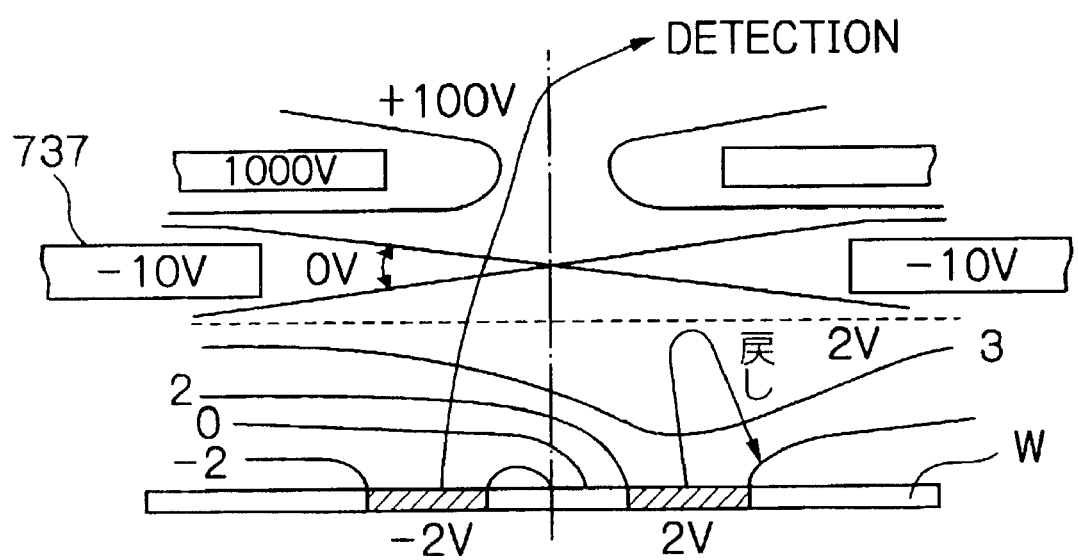
FIG. 35 is a schematic diagram illustrating a potential distribution in a potential contrast measurement.

For example, it is assumed that an equipotential surface of 0V has such a profile around the electrode 737 as illustrated in FIG. 35, when a voltage of −10V is applied to said electrode 737. In that case, the secondary electron emitted from the pattern having the potential of −2V with the given energy of 0V can run over the potential barrier of 0V thus to be detected, because that secondary electron should still has the energy retained at the level of 1 eV at the equipotential surface of 0 eV, while on the other hand, the secondary electron emitted from the pattern having the potential of +2V with the given energy of 0 eV is only permitted to go up to the equipotential surface of 2 eV, which forces the secondary electron to return back toward the sample and the secondary electron would not be anyhow detected. Accordingly, the image for the pattern of −2V is formed to be brighter, while the image for the pattern of 2V is formed to be darker. Thus the potential contrast may be measured.

Further, when a potential measurement of high time resolution is to be performed, a pulse voltage may be applied to a blanking deflector 731 to deflect the beam and thereby to block said beam by a blanking knife edge 734 so as to form it into a multi-beam in the form of short pulses, thereby accomplishing the above-described measurement.

Figure 36A:
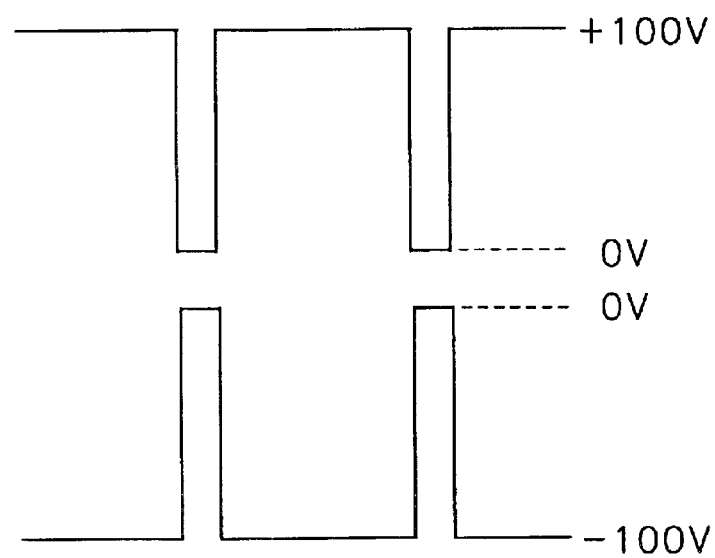
FIG. 36 is a diagram illustrating a relation between a pulse potential applied to a blanking deflector and an incident beam current onto a sample in a potential measurement of high time resolution.
Figure 36B:
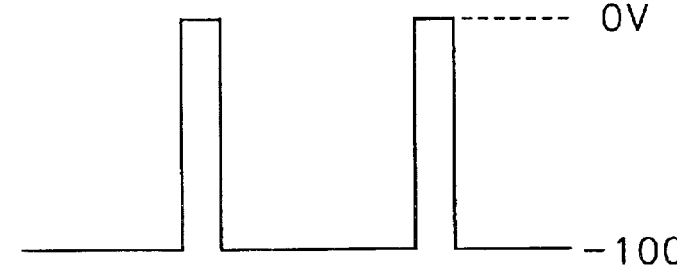
Figure 36C:

For example, if such pulse voltages as illustrated respectively by [A] and [B] of FIG. 36 are applied to electrodes of the blanking deflector 731 disposed in the left and the right sides with respect thereto, then such a pulsed beam current as illustrated by [C] of FIG. 36 would be entered onto the wafer. Accordingly, if the pulsed electron beam is entered to the pattern and the secondary electrons emitted at that time are detected, the potential of the pattern can be measured with the time resolution having said pulse width. It is to be noted that those dotted lines between the blanking deflector 731 and the blanking knife edge 732 in the drawing designate electron beam orbits at the time of blanking.

An inspection procedure by using said electron beam apparatus of the present invention will now be described.

Figure 37:
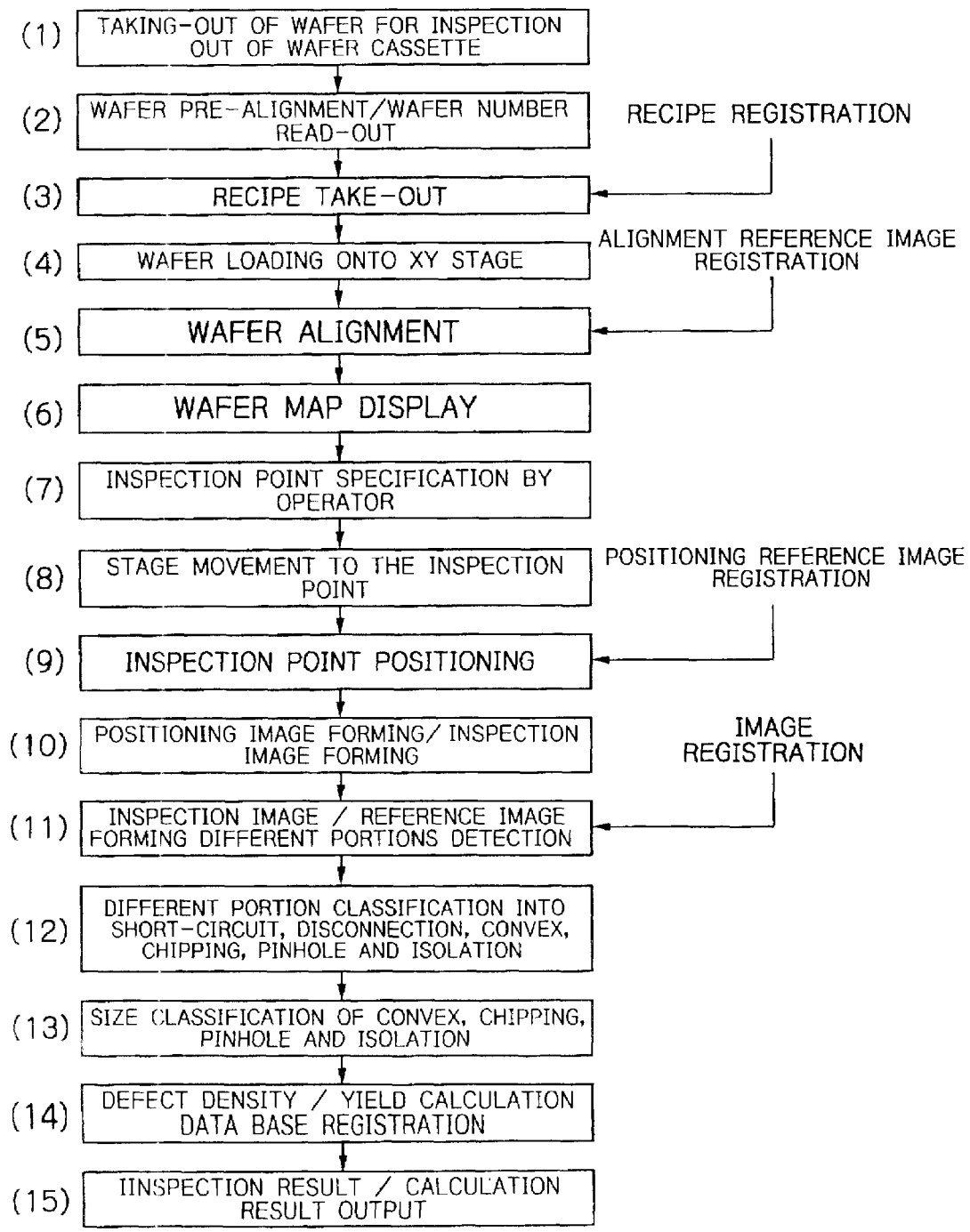
FIG. 37 is a flow chart illustrating an inspection procedure according to the present invention.

FIG. 37 shows an example of the inspection procedure according to the present invention. A wafer 11 subject to an inspection is taken out of a wafer cassette (1) and then pre-aligned, while at the same time a wafer number reader, though not shown, reads out a wafer number having been formed on this wafer (2). The wafer number is unique to an individual wafer. The read-out wafer number is used as a key to read out a recipe corresponding to this wafer (3), said recipe having been registered in advance. The recipe includes the inspection procedure and/or the inspection condition defined for this wafer.

Subsequent operations may be performed automatically or semi-automatically according to the read-out recipe. After the wafer number having been read-in, the wafer W is transferred and mounted onto an XY stage in a sample chamber held into a vacuum (4). The wafer W loaded on the XY stage is aligned by the primary and the secondary optical systems installed within the sample chamber (5). The alignment operation may be performed in such a manner that an enlarged image of the alignment pattern formed on the wafer W is compared with a reference image registered in advance for the alignment in association with the recipe and then a stage position coordinate is corrected such that the alignment image can be superposed exactly on the reference image. After the alignment, a wafer image (an inspection pattern image) corresponding to this wafer is read out and indicated on a display (6). The wafer image shows a required inspection point and a history for this wafer.

After the wafer image having been indicated, an operator specifies a point corresponding to a position desired to be inspected among the inspection points shown on the wafer image (7). Once the inspection point is specified, the stage moves and brings the wafer W subject to the inspection to such a location that the specified inspection point thereon may be positioned directly below the electron beam (8). After this movement, the scanning electron beam is irradiated onto the specified inspection point, and an image for the purpose of positioning with a relatively low magnification is formed thereon. Then, similarly to the aligning procedure, the formed image is compared with a reference image corresponding to the specified inspection point, which has been registered in advance for positioning, and a precise positioning is performed so that the formed image may be superposed exactly on the reference image (9). The positioning may be accomplished by, for example, a fine-adjustment of the region to be scanned by the electron beam.

If appropriately positioned, the wafer should be located such that the region to be inspected is in an approximately central location of the screen, that is, a location directly below the electron beam. In this state, an image in the inspection region to be used for an inspection with a high magnification may be formed (10). The image to be used for the inspection is compared with a reference image corresponding to this region to be inspected, which has been registered in advance for the inspection in association with the recipe, and then a different portion between those two images is detected (11). The different portion is considered as a pattern defect. The pattern defect may be classified into such defect groups including at least short-circuit, disconnection, convex, chipping, pinhole and isolation (12).

Subsequently, the convex and the isolation defects are classified according to the size, in which a distance to an adjacent pattern is defined by a unit representing a minimum space and a subtending length (a length of a shadow of a defect projected to a pattern) by a unit representing a minimum pattern width. On the other hand, the pinhole and the chipping defects are classified according to the size, in which a width of a pattern including either of said defects is used as a unit defining the size in the width direction and a minimum pattern width is used as a unit in the longitudinal direction (13). It is to be noted that the minimum pattern width and the minimum space are values to be defined based on a pattern design rule for the device subject to the inspection and these values should have been registered prior to the inspection.

After the defect determination and the classification thereof regarding to the specified inspection point having been completed, the classification result is stored in the inspection database while being used to overwrite the specified inspection point on the wafer image. Thus the inspection procedure for one location comes to the end as described above.

If there are remaining any inspection locations, a subsequent inspection point may be specified on the wafer image, and the operations following to the step of specifying the inspection point in FIG. 37 may be repeated. After full range of inspection on said wafer having been finished, a density and/or a yield for a total defect, for each classified defect, and for each defect distinguished by size is calculated for each chip or wafer (14). The calculation of the yield may be executed by using a critical rate table of defect size for the respective defect types registered in advance. The critical rate table of defect size has been prepared to correlate each of the defects including the convex, chipping, pinhole and isolation, which have been classified by size, with each unique critical rate. These calculation results may be stored in the inspection database together with the inspection result (14), and output to be used at any times as desired (15).

If there remains any wafers to be measured in a wafer cassette, a subsequent wafer is taken out of the wafer cassette and then inspected according to the procedure shown in FIG. 37. The density and the yield for a plurality of wafer are also calculated similarly to the case of the wafer as described above.

It is to be appreciated that if the electron beam apparatus is further equipped with additional analyzing functions by means of, for example, a characteristic X-ray analyzer or an Auger electron analyzer, it may become possible to obtain analytic data of the inspection point such as data including a defective composition in addition to the classification in the defect determination based on the inspection image.

Further Alternative Embodiment of Electron Beam Apparatus

Figure 38:
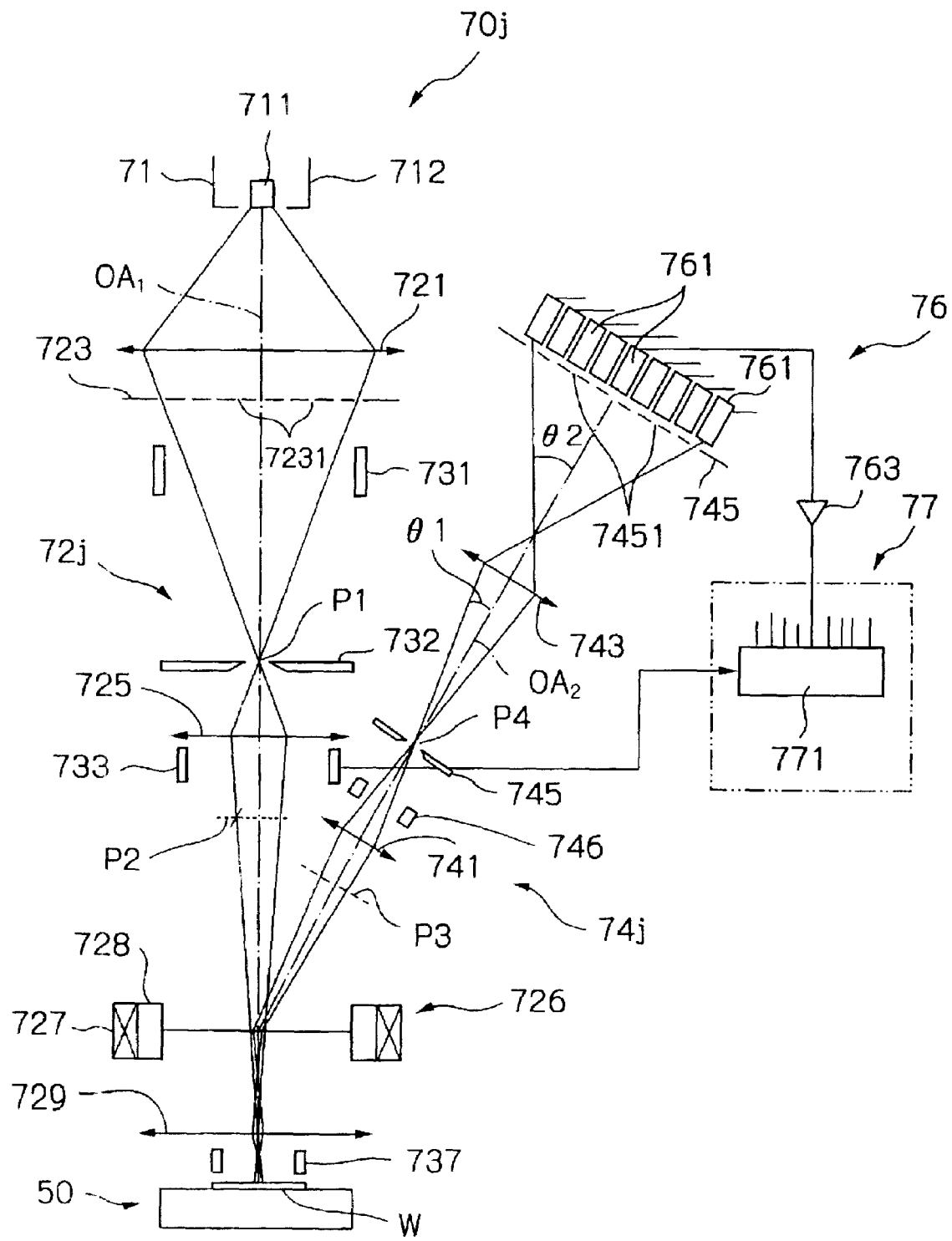
FIG. 38 is a diagram illustrating a general configuration of still another embodiment of the electron beam apparatus according to the present invention.
Figure 39:
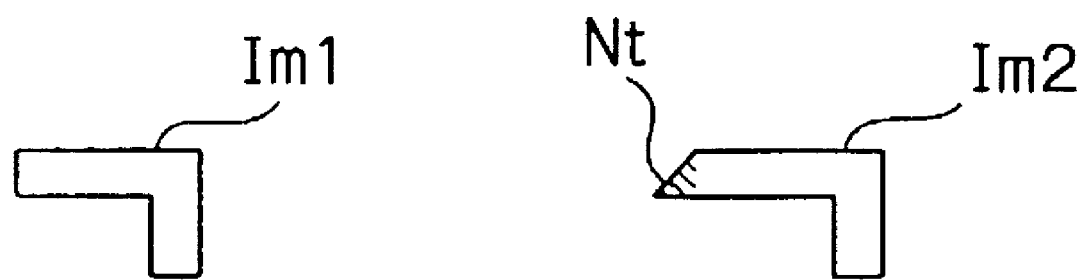
FIG. 39 is a diagram for explaining a wafer inspection method according to the present invention, illustrating a pattern defect detection.

FIGS. 38 and 39 show an alternative embodiment of the electron beam apparatus designated generally by reference numeral 70*j*. In FIGS. 38 and 39, the same components as those in the electron beam apparatus shown in FIG. 8 are designated respectively by the same reference numerals and detailed explanations on the structure and function thereof will be omitted. Besides, components different from but similar to those in FIG. 8 are designated respectively by the same reference numerals, each added with a suffix "j".

An electron beam apparatus according to this embodiment is same as the electron optical apparatus as shown in FIG. 8 with the exception that an aperture plate 735 defining an aperture is located at a point P1 where a crossover of a primary optical system 72*j* is formed, that an aperture plate 747 defining an aperture is located at a point P4 where a crossover of a secondary optical system 74*j* is formed, and that the secondary optical system 74*j* comprises an electrostatic deflector 746.

In the electron beam apparatus of the present embodiment, a plurality of secondary electron beams emitted from respective irradiation spots on a wafer W is guided to a detector through the secondary optical system 74*j*. In a stage prior to a magnifying lens 743, the electrostatic deflector 746 is arranged so as to function as an axially aligning device for the magnifying lens 743. Further, the aperture plate 747 defining the aperture is arranged at the location P4 where the second crossover image is formed so as to obtain the resolution of the second optical system.

Herein, any cross talks among a plurality of beams may be avoided by making a spacing between a plurality of primary electron beams be greater than the resolution of the secondary optical system as converted into the value on the wafer surface. The spacing between the irradiation spots is scanned by said electrostatic deflector 746. This allows an image to be created in the same principle as of the SEM and also with a throughput proportional to the number of beams. Since chromatic aberration can be reduced by controlling an angle of deflection of the electrostatic deflector 746 to a value proximal to $-\frac{1}{2}$ of an angle of electromagnetic deflection by an ExB separator 726, therefore the deflection would not increase the beam diameter excessively.

Each of detecting elements of a detector 761 is connected via each of amplifiers 763 to an image data processing section 771 of a process control system 77 for converting a detection signal to the image data. Since the image data processing section 771 is supplied with the same scanning signal as that given to a deflector 733 for deflecting the primary electron beam, the image data processing section 771 can figure out an image representative of the scanned surface of the wafer W from the detection signal obtained during the beam scanning.

As can be seen obviously from FIG. 38, since a portion in the optical path common to the primary optical system and the secondary optical system is the portion from the ExB separator 726 through an objective lens 729 up to the wafer W, the number of common optical parts has been successfully decreased. Owing to this, even if the lens condition for the objective lens 729 was matched to the primary electron beam, a focusing condition for the secondary electron beam can be adjusted by using the magnifying lenses 741 and 743. The latter, the magnifying lens 743 is to magnify an angle θ1 made by an orbit of the secondary electron and the optical axis $OA_2$ to θ2.

In addition, although the axial alignment with respect to the objective lens 729 is performed favorably to the primary electron beams by applying an axial aligning power supply voltage onto the deflector 728 in superposition to its due voltage, the axial mismatch of the secondary electron beam due to the axial alignment favorable to the primary electron beam can be compensated for by using the axial aligner for the secondary optical system or the deflector 746.

As for the aperture plate defining the aperture, two aperture plates has been employed, one of which is the aperture plate 735 for passing only the primary electron beam therethrough disposed at the location P1 where the first cross over image is formed, and the other of which is another aperture plate 747 for passing only the secondary electron beam therethrough disposed at the location P4 where the second cross over image is formed, thereby allowing an optimal aperture diameter to be selected individually. Employing a size of an aperture of the objective lens 729 sufficiently greater than the diameter of the cross over herein and zooming the objective lenses 721 and 725 so as to make the cross over size variable at the position of the objective lens 729 can make an angular aperture selectable. This allows the angular aperture to be adjusted to a desired optimal value within a range determined by the trade-off between the low aberration and the high beam current by only using an electric signal without exchanging apertures.

As for the location of the aperture of the secondary optical system, such a condition should be satisfied that the secondary electron image could be focused on the detector 761 by the magnifying lenses 741 and 743. Then, the aperture is to be moved along the optical axis $OA_2$ until the location where every secondary electron beam may have the same intensity when the wafer with the inspected surface having a uniform emission characteristic has been used, and at that location, the aperture of the secondary optical system should be fixed. This position is the location in the optical axis direction where the principal ray from the wafer would cross the optical axis as illustrated.

In a pattern defect inspection method for a wafer W by way of the pattern matching, a control section which is not shown but has been provided for controlling the electron beam apparatus executes a comparative matching between a secondary electron beam reference image of a wafer having no defect which has been stored in a memory thereof in advance and an actually detected secondary electron beam image so as to calculate a similarity between those two images. For example, if the calculated similarity is not greater than a threshold, it is determined that "a defect exists" and if the calculated similarity is greater than the threshold, it is determined that "no defect exists". At this stage, the detected image may be displayed on a CRT, though not shown. Thereby, an operator can make a final confirmation and thus evaluate whether the wafer W has actually a defect or not. Further, the images may be compared to see a matching in segment by segment base so as to detect automatically the segment including the defect. In that case, preferably an enlarged image representing the defective segment should be displayed on the CRT.

Still further, for a wafer having a number of same dice, the detected images may be compared between the detected dice so as to detect the defective part without the need for using the reference image as described above. For example, FIG. 39 [A] shows an image Im1 for a firstly detected die and another image Im2 for a secondarily detected die. If it is determined that another image for a thirdly detected die is same as or similar to the first image Im1, then it can be determined that the second die image Im2 has a defect in the segment Nt, and thus a defective part can be detected. At this stage, the detected image may be displayed on the CRT while marking the segment determined to be defective.

It is to be noted that to measure a line width of a pattern or a potential contrast of the pattern formed on the wafer, the operation may be performed in the manner as described in conjunction with FIG. 24, and the explanation thereof will be omitted.

Referring to FIG. 38, since a blanking deflector 731 has been provided, said deflector 731 may be used to deflect the primary electron beam toward the aperture at the cross over image formation point in a predetermined cycle so as to permit the beam to pass therethrough for a short period and to block it for the rest of the period, which will be repeated, then it will be possible to form a bundle of beams having a short pulse width. If such a beam having a short pulse width is used to measure the potential on the wafer as described above, the device operation characteristics can be analyzed with high time resolution. That is, the present electron beam apparatus can be used as what is called an EB tester.

Further Alternative Embodiment of Electron Beam Apparatus

Figure 40:
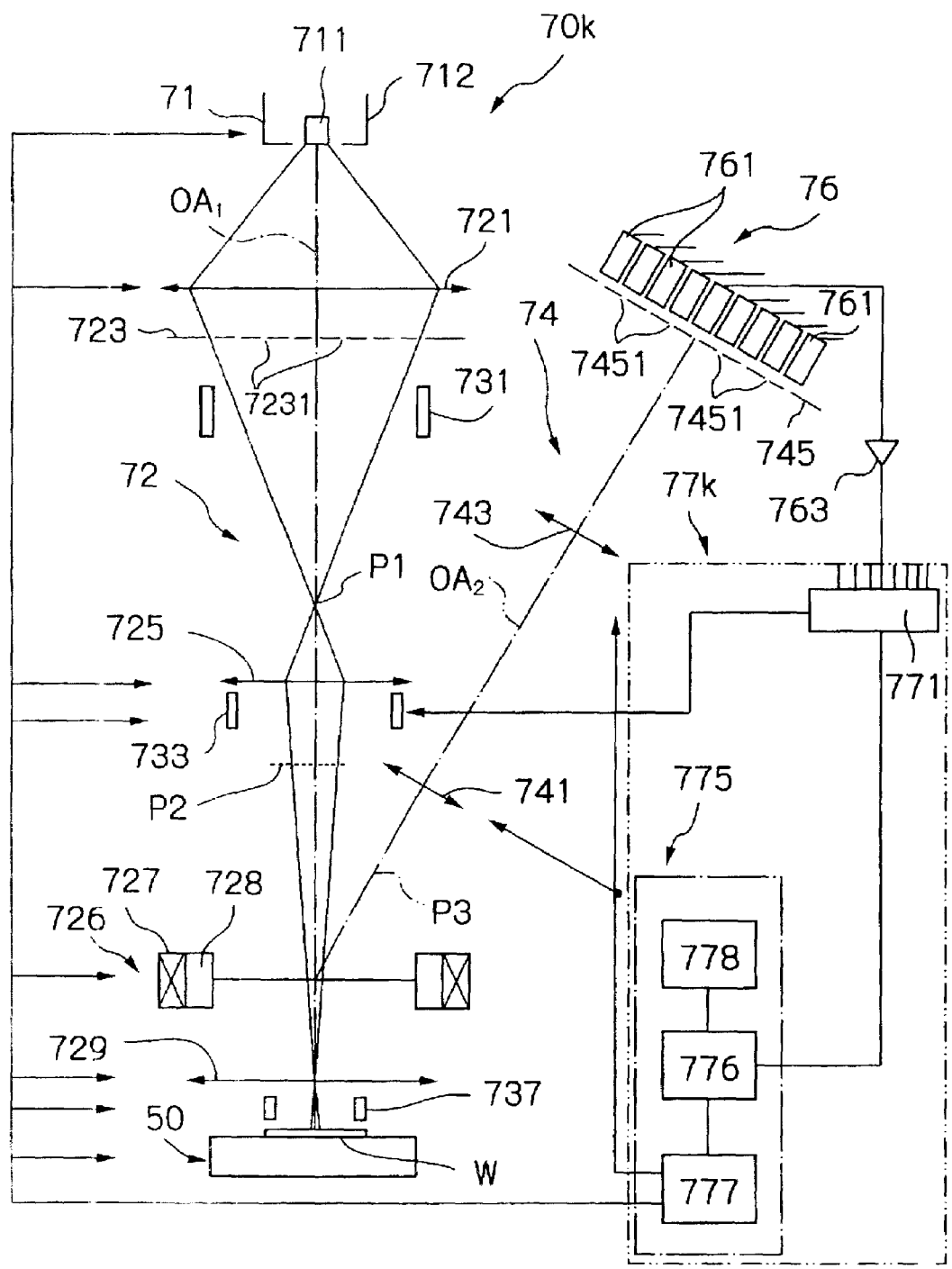
FIG. 40 is a diagram illustrating a general configuration of still another embodiment of the electron beam apparatus according to the present invention.

FIG. 40 shows an alternative embodiment of the electron optical apparatus or the electron beam apparatus designated generally by reference numeral 70k. In FIG. 40, the same components as those in the electron beam apparatus shown in FIG. 8 are designated respectively by the same reference numerals and detailed explanations on the structure and function thereof will be omitted. Besides, components different from but similar to those in FIG. 8 are designated respectively by the same reference numerals, each added with a suffix "k".

The electron beam apparatus according to the present embodiment is same as the embodiment of FIG. 8 with the exception that the apparatus further comprises a mode determining circuit 775 connected to an image data processing section 771 of a process control system 77k, that said mode determining circuit 775 is provided with a CPU 776, a memory section 777 connected to said CPU 776 and an operator console 778, and that said memory section is connected to respective components in a primary optical system 72 and a secondary optical system 74.

In the electron beam apparatus of the present embodiment, a secondary electron image is formed on one of a plurality of apertures 7451 of a second multi-aperture plate 745 by magnifying lenses 741 and 743, and this second electron image is detected by each of detectors 761. Each of those detectors 761 converts the detected secondary electron image into an electric signal representing an intensity thereof. In this way, the electric signal output from each of the detectors, after having been amplified by the corresponding amplifier 763, is entered into the image data processing section 771 of the process control system 77k and converted into an image data in this image data processing section. Since the image data processing section 771 is further supplied with the scanning signal for deflecting the primary electron beam, the image data processing section 771 may display an image representative of the surface of a sample or a wafer W. By comparing this image with a reference pattern allows a defect in the wafer to be detected, and further, by moving the pattern to be evaluated on the wafer W to a location proximal to an optical axis $OA_1$ of the primary optical system 72 by way of registration and then line-scanning this pattern, a line width evaluation signal for the pattern formed on the top surface of the sample can be extracted, which is further calibrated appropriately so as to measure the line width of the pattern.

In the case for evaluating a wafer having a pattern with a minimum line width of 0.1 μm, if there are some evaluation modes available for the electron beam apparatus, including a mode using a pixel size of 0.2 μm for performing an evaluation with high throughput, another mode using the pixel size of 0.1 μm for performing an evaluation with higher precision but the throughput deteriorated to one-quarter of that by the first mode, and further the other mode using the pixel size of 0.05 μm for allowing an evaluation with much higher precision but the throughput further deteriorated to one-quarter of that by said another mode, then such electron beam apparatus may advantageously works for many uses.

On the other hand, when the pixel size is changed, the beam size and thus a scanning dimension need to change in association with the change in pixel size. To change the scanning dimension, it is only required to change a voltage to be applied to the deflector. In contrast, to change the beam size, it is required to change many parameters.

In FIG. 40, the primary electron beam, after having passed through a plurality of apertures 7231 of the multi-aperture plate 723 is forcused by a reduction lens 725 and an objective lens 729. Accordingly, conditions for the reduction lens 725 and the objective lens 729 may be determined and stored in the memory section in advance, so that the zooming effect from those two lenses may be used to change a reduction ratio to form a beam in a size suitable for each of the pixel sizes of 0.05 μm, 0.1 μm and 0.2 μm, and the appropriate condition may be extracted and established at each time when the mode is changed. From the viewpoint of the secondary optical system, since the objective lens is determined by the condition for the primary optical system, the above-described method is not applicable to the secondary optical system. In the secondary optical system, the lens condition may be determined such that the secondary electrons or a principal ray emitted from the sample in a right angle with respect to the surface thereof can be entered exactly into each of the apertures 7451 of the second multi-aperture plate 745 of the secondary optical system by at least one-step of lens arranged downstream to an ExB separator 727. These lens conditions and axial aligning conditions for each of those three modes may be stored in the memory section 777 of the mode determining circuit. Then, the input from the operator console 778 may control the CPU 776 to extract the conditions and to reset the values appropriately at each time when the mode is changed.

Figure 41:
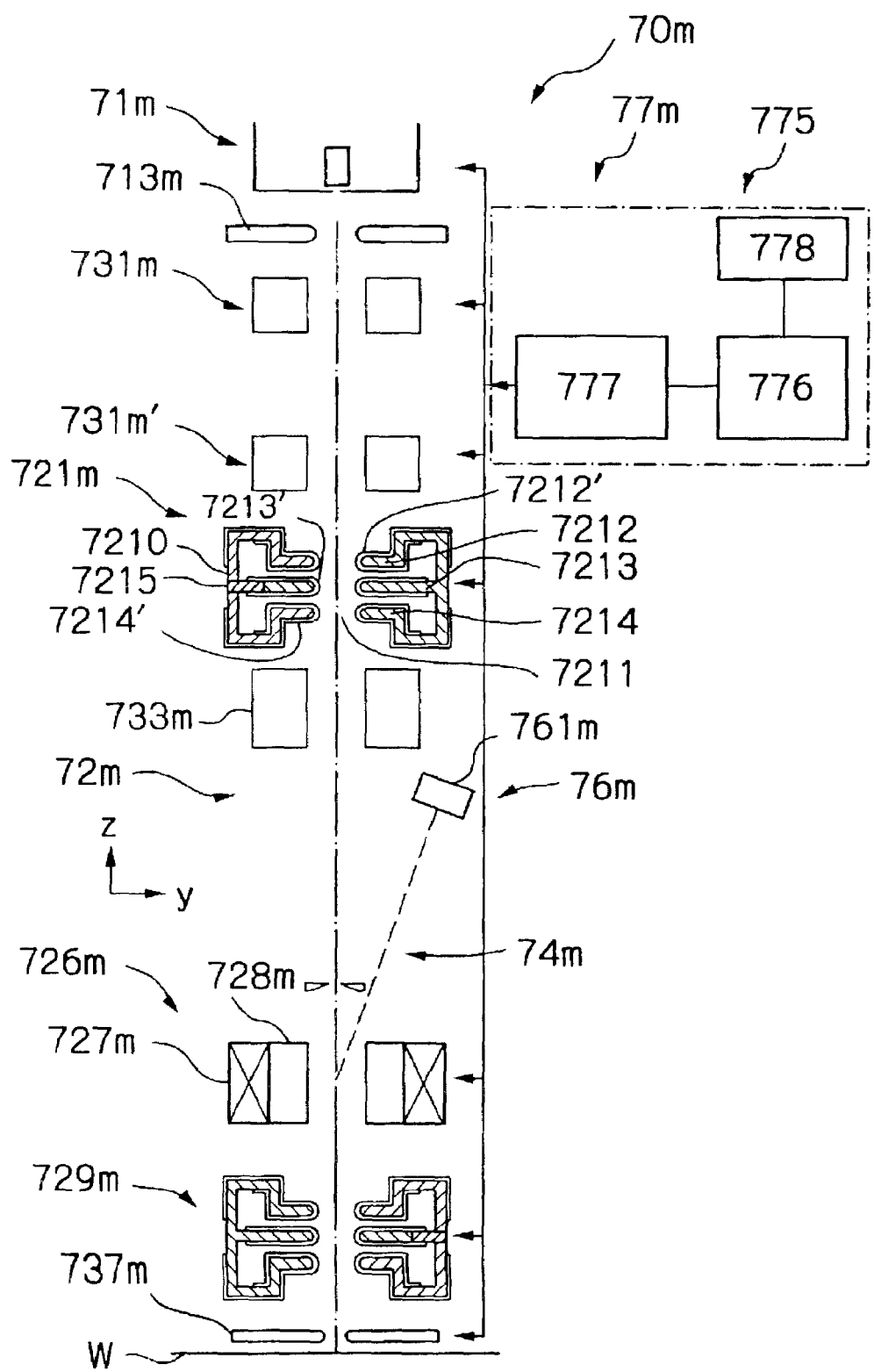
FIG. 41 is a diagram illustrating an embodiment of a scanning electron beam apparatus to which a feature of the electron beam apparatus of FIG. 40 is applied.

FIG. 41 shows an embodiment in which a mode determining circuit similar to that in preceding embodiment is applied to an electron beam apparatus of the scanning type for irradiating a single electron beam, which is designated generally by reference numeral 70m. In FIG. 41, components corresponding to those in the preceding FIG. 40 are designated by the same reference numerals, each added with a suffix "m".

In this embodiment, since a condenser lens 721 m has substantially the same structure as that of an objective lens 729m, therefore the condenser lens is representatively explained in detail.

The condenser lens 721m, which is an electrostatic axially symmetric lens, comprises a main body 7210 made of ceramic. This main body 7210 is formed to be annular in plan view to define a circular opening 7211 in a central portion thereof, and an inner circle side thereof is divided into three plate-like sections 7212 to 7214 spaced to one another in a longitudinal direction (the direction along the optical axis) in FIG. 41. An outer surface of the ceramic made main body 7210, especially the outer surface of the plate-like sections 7212 to 7214, is coated with metal coating films 7212' to 7214'. These coating films 7212' to 7214' serve as electrodes respectively, in which to the coating films 7212' and 7214' is applied respectively a voltage having a level approximate to the ground side, while to the central coating film 7213' is applied a positive or a negative high voltage having a high absolute value through the electrode fitting 7215 provided on the main body 7210, thereby to serve as a lens. Such lens is allowed to be of high processing accuracy and to be made smaller in an outer diameter because each element thereof is formed out from a single piece of ceramic by machining and finishing simultaneously.

Figure 42:
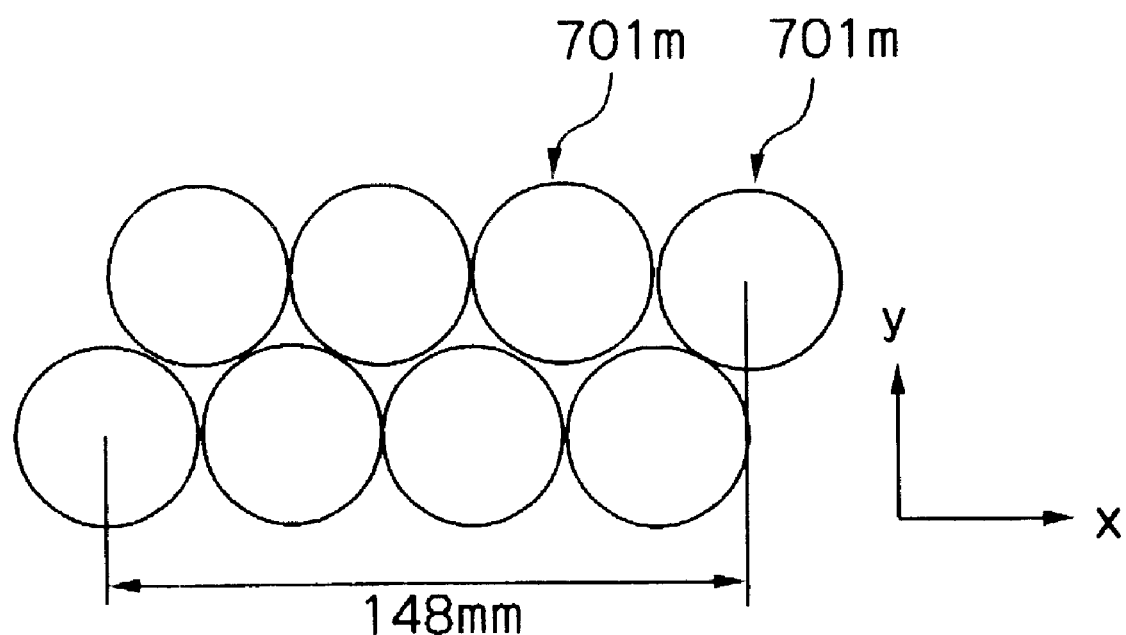
FIG. 42 illustrates an arrangement of the optical systems in the electron beam apparatus.

In the electron beam apparatus of the above embodiment, since the outer diameter of the lens can be made smaller, the diameter of the optical column containing the electron beam apparatus also may be reduced. Therefore, it becomes possible to arrange a plurality of optical columns for one piece of sample such as a wafer having a larger diameter. For example, the array of four pieces of optical columns in the X direction by two rows in the Y direction, that is, eight optical columns 701m in total may be arranged for one piece of sample, as shown in FIG. 42. In this arrangement, the distances between optical axes of respective optical systems projected in the X-axis direction are made all equal. Employing such an arrangement can eliminate a not-evaluated region or a doubly evaluated region with several times of mechanical scanning. Then, when the stage (not shown) holding the wafer W is continuously moved in the Y-direction and each of the optical columns scans in the X direction with a width of 1.1 mm, then a 8 mm wide region can be evaluated with one time of mechanical scanning. It is to be appreciated that a 50 μm wide region should be doubly evaluated.

The lens conditions and axial aligning conditions for each of the modes may be measured in advance and stored in the memory section 777 belonging to the mode determining circuit 775, and then, an input from the operator console 778 controls the CPU 776 to extract the conditions and reset the values appropriately at each time when the mode is changed.

Further Alternative Embodiment of Electron Beam Apparatus

Figure 43:
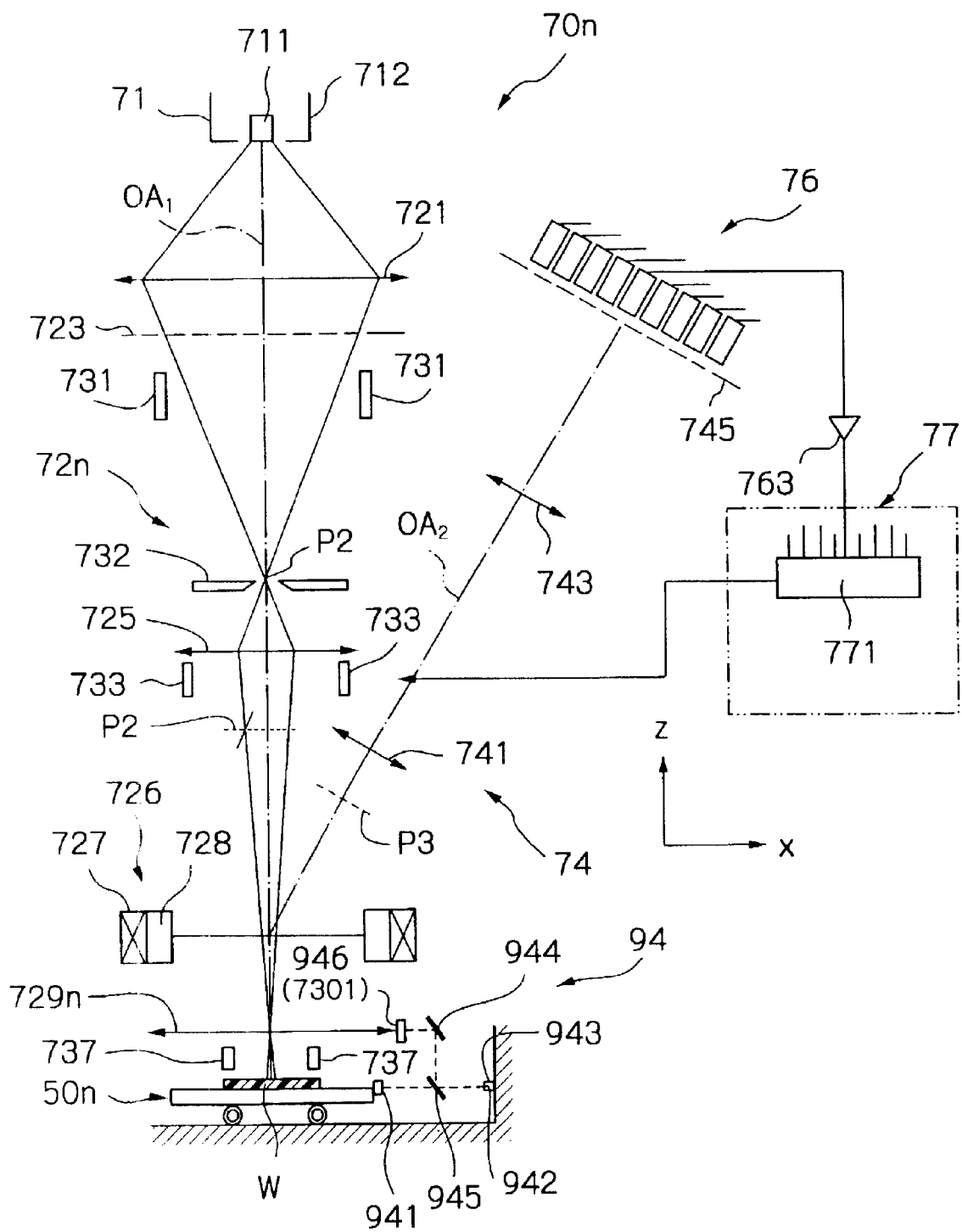
FIG. 43 is a diagram illustrating a general configuration of still another embodiment of the electron beam apparatus according to the present invention.
Figure 44:
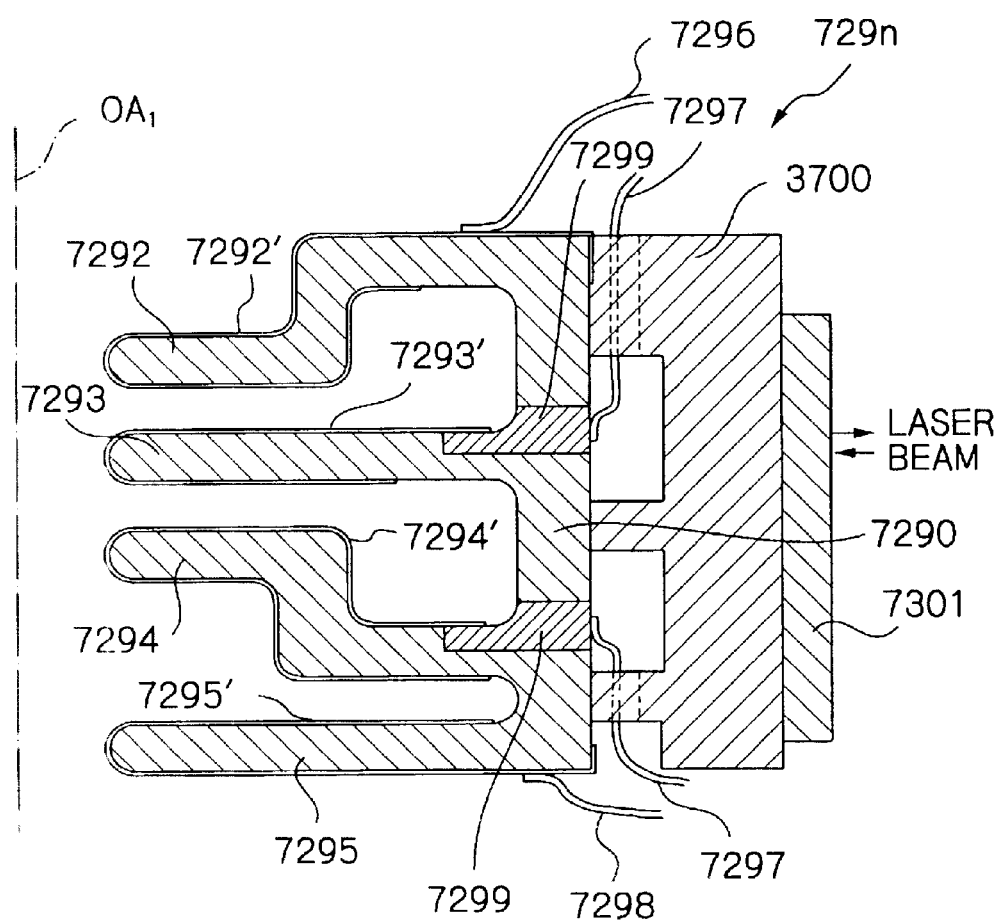
FIG. 44 illustrates a configuration of an electrostatic lens, which configures an object lens, installed in the electron beam apparatus shown in FIG. 43.

FIGS. 43 and 44 show an alternative embodiment of the electronic optical apparatus or the electron beam apparatus designated generally by reference numeral 70n. In FIGS. 43 and 44, the same components as those in the electron beam apparatus shown in FIG. 8 are designated respectively by the same reference numerals and detailed explanations on the structure and function thereof will be omitted. Besides, components different from but similar to those in FIG. 8 are designated respectively by the same reference numerals, each added with a suffix "n".

The electron beam apparatus according to the present embodiment is same as the embodiment of FIG. 8 with the exception that the apparatus further comprises a laser interferometer in association with the stage unit and the objective lens, and that an aperture plate is arranged at a point P1 where a cross over is formed.

FIG. 44 illustrates in detail a specific structure of an electrostatic lens which constitutes an objective lens 729n shown in FIG. 43. The objective lens 729n is formed into an axially symmetric structure centering around an optical axis $OA_1$, wherein only a right half-portion thereof is shown in a sectional view of FIG. 44.

The objective lens 729 may be fabricated in the following manner. Primarily, a metal bar 7299 is embedded into a ceramic material, which can be shaped by machining, so as to form a circularly cylindrical part 7290. Secondarily, the ceramic material is machined with a lathe in order to form an upper electrode section 7292, a central electrode section 7293, a lower electrode section 7294 and an axially symmetric electrode section 7295. Then, the masking is applied to those portions where the surface of the ceramic material is to be exposed for insulation, and a metal plating is applied to the remaining surface portions of the ceramic material by way of electroless plating, thereby forming an upper electrode 7292', a central electrode 7293', a lower electrode 9294' and an axially symmetric electrode 7295'.

The upper electrode 7292' is supplied with a voltage from a lead 7296 connected to a top surface thereof. The central electrode 7293' and the lower electrode 7294' are supplied with voltages from leads 7297 via a pair of metal bars 7299. It is to be noticed that a vacuum sealing is not necessary to the metal bar 7299. The axisymmetric electrode 7295' is supplied with a voltage from a lead 7298 connected to a lower face thereof.

A cylindrical part made of ceramic having such a configuration as described above may be fabricated small in size, and then a ceramic member 7300 having a low coefficient of linear expansion (e.g., NEXCERAN113 available from Nippon Steel Corporation) is adhered onto the outer side thereof. Then, a planer stationary laser mirror 7301 is fixedly adhered to the outer side of said ceramic member 7300. The stationary laser mirror 7301 may be formed by polishing a side of the ceramic member 7300 subject to the laser beam to be a mirror-surface.

The integration of the stationary laser mirror 7301 into the objective lens 729n (fixing by adhesion or integration in structure) makes it possible that in case of the vibration of the optical system in the X-Y plane direction in addition to the vibration of the stage unit as the matter of course, the laser interferometer measures a displacement of the electron beam due to such vibration and the beam position may be accordingly compensated. That is, even if the objective lens 729n vibrates in the x-y direction, a variation in relative distance with respect to the stage 50n can be measured by the laser interferometer 94 and thereby the compensation may be applied to the beam so as to offset the variation. In this manner, a relative micro-vibration between the optical system and the stage can be compensated and thereby an image distortion due to the vibration of the optical system can be reduced.

An evaluation such as a defect inspection of a pattern formed on a surface of a wafer W which is a sample is to be accomplished by using the electron beam apparatus shown in FIG. 43, an electrostatic deflector 733 and a magnetic deflector 728 of a Wien filter or an E×B separator 726 should be operated interlockingly and at the same time an X table and a Y table of a stage unit 50n are to be moved, so that a plurality of primary electron beams may scan the surface of the wafer W in the X-direction while continuously moving the wafer W in the Y-direction, thus scanning the overall surface of the wafer W. That is, after the stage unit 50n having been moved to place the wafer W at a scanning starting end, the stage unit is moved continuously in the Y-direction while controlling a plurality of primary electron beams to scan in the X-direction with an amplitude slightly greater than a distance between respective primary electron beams, Lx (shown in FIG. 9). This means that the wafer could have been scanned in the region extending along the Y-direction having a width w equivalent to full scanning distance of the plurality of primary electron beams in the X-direction, and a signal in association with the scanning in said region would be output from a detector 761.

Subsequently, after the stage unit having been moved in the X-direction by a step equivalent to the width w, the table of the stage unit 50 is continuously moved in the Y-direction while controlling the plurality of primary electron beams to scan the wafer W in the X-direction by the distance equivalent to the width w. Thereby, another region of the width w adjacent to the region having been previously scanned would have been scanned both in the X- and the Y-directions. After this, the similar operations may be repeated to scan the overall surface of the wafer W, and the signal obtained as a result of scanning operations from the detector 761 may be processed so as to evaluate the wafer W.

It is to be appreciated that, preferably, the laser interferometer 94 should be employed in order to precisely control the movement of the stage unit 50n. To achieve this, the X table and the Y table of the stage unit are provided with movable laser mirrors 941, while a laser interferometer 942 with a built-in laser oscillator 943, a stationary laser mirror 946 (which may be the same mirror as the reference mirror 7301 of FIG. 44) secured fixedly to the objective lens, a reflection mirror 944 and a dichroic mirror 945 are mounted respectively in appropriate locations on the stationary side as illustrated, so that a position of the stage can be calculated based on the interference between the light which has followed an optical path from the laser oscillator 943 → the dichroic mirror 945 → the reflection mirror 944 → the stationary laser mirror 946 (7301) → the reflection mirror 944 → the dichroic mirror 945 → the laser interferometer 942 and the light which has followed another optical path from the laser oscillator 943 → the dichroic mirror 945 → the stationary laser mirror 941 → the dichroic mirror 945 → the laser interferometer 942.

In the laser interferometer 94 of FIG. 43, the interferometer for either one of the X-axis or the Y-axis direction has been illustrated, and the interferometer for the other direction has been omitted. However, in practice, the interferometer should be provided for both of the X-axis and the Y-axis directions as a matter of course. For example, as for the movable mirror 941, orthogonal side faces of the X and the Y tables of the stage unit may be provided with movable mirrors for the X-axis and for the Y-axis, respectively.

If the wafer W is a semiconductor wafer, then instead of the above-described evaluation method, the following method may be taken to evaluate the wafer W. That is, a marker may be arranged at an appropriate location on the surface of the wafer W, such that only the one electron beam among a plurality of primary electron beams, which has been formed by one aperture of a multi-aperture plate 723, may be allowed to scan said marker and an output from the detector at that time of scanning is extracted to detect the position of the marker. Thereby, a physical relationship between the wafer W and the primary electron beam can be determined, and therefore, if an orientation of a circuit pattern formed on the surface of the wafer W with respect to the X- and the Y-directions have been determined in advance, a plurality of primary electron beams could be guided to the correct position to meet said circuit pattern and the beams therein could scan the circuit pattern, thereby accomplishing the evaluation of the circuit pattern on the wafer W.

Further, the line width of the pattern on the surface of the wafer W can be measured in such a way that first a pattern to be evaluated on the wafer W is moved by registration to the proximity to the optical axis of the primary optical system and the wafer W is line-scanned with the primary electron beam to detect the secondary electron beam, and then a signal corresponding to this secondary electron beam is detected to extract a signal for evaluating the line width of the circuit pattern on the surface of the wafer W, which is then calibrated appropriately thus to measure the line width of the pattern on the surface of the wafer W.

Figure 45:
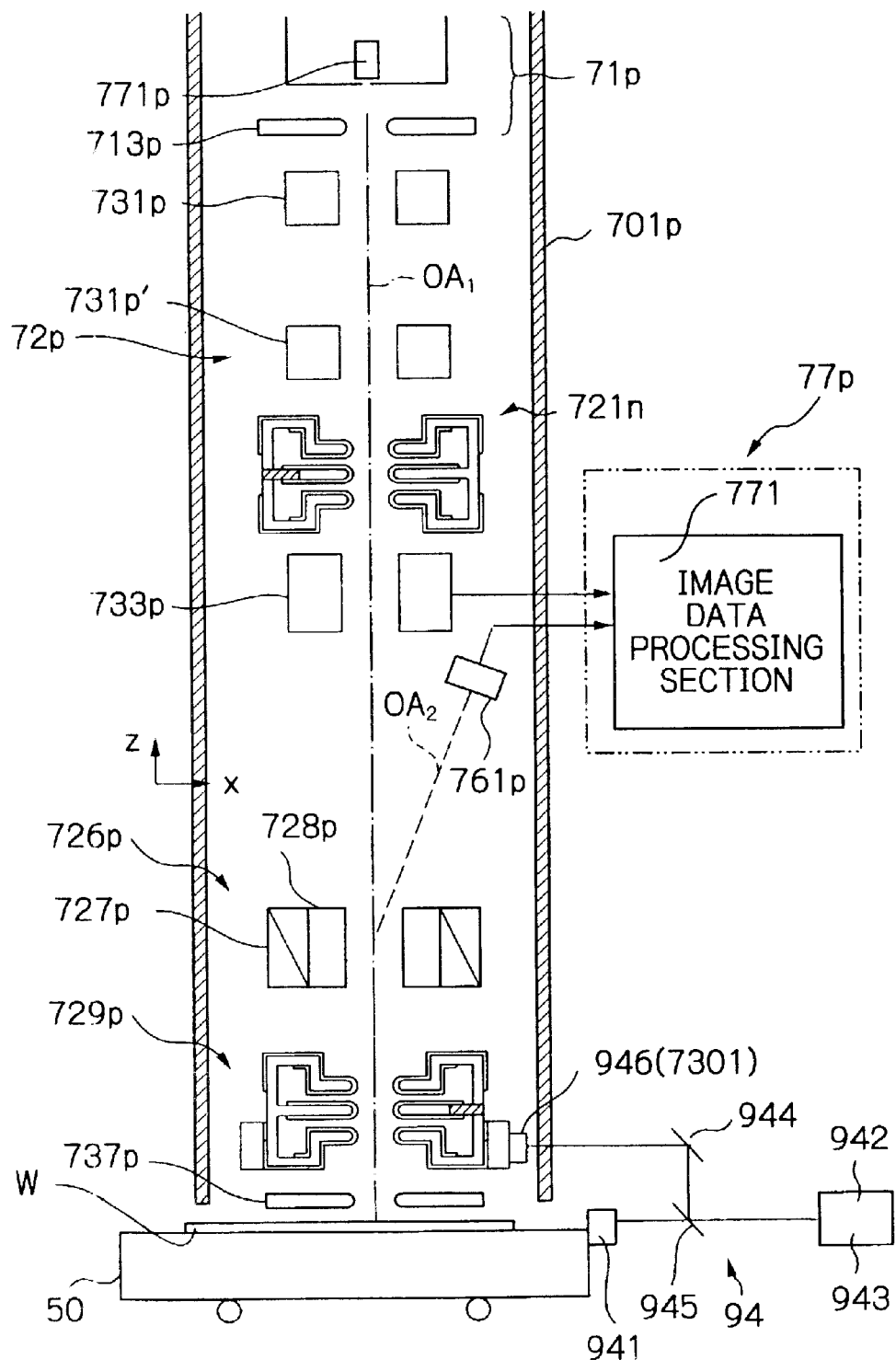
FIG. 45 is a diagram illustrating an embodiment of a scanning electron beam apparatus to which a feature of the apparatus shown in FIG. 43 is applied.

FIG. 45 shows an embodiment in which a mode determining circuit having a principle similar to that of the above-described embodiment is applied to an electron beam apparatus of scanning type for irradiating a single electron beam, which is designated generally by reference numeral 70*p*. In FIG. 45, components corresponding to those in the embodiment of FIG. 43 are designated by the same reference numerals, each added with a suffix "p", An electron gun 71*p* comprises an anode 713*p* and a cathode 711*p* so as to emit a primary electron beam having a cross over with a diameter of approximately 10 microns. Thus emitted, the primary electron beam passes through an axial aligning deflectors 731*p*, 731*p'* and further through the condenser lens 721*p*, where being converged, and further passes through a deflector 733*p* and a Wien filter or an ExB separator 726*p*, and thereafter the beam is forcused by an objective lens 729*p* so as to be formed into an image on the proximity to a plurality of circuit patterns in the shapes of, for example, rectangles formed on a surface of a wafer W loaded on a stage unit 50. Deflectors 10 and 40 control the primary electron beam to scan the wafer W.

Secondary electron beam emitted from the pattern on the wafer W as the result of the scanning with the primary electron beam is accelerated by an electric field of the objective lens 729*p* and deflected by the Wien filter 726 to deviate from an optical axis $OA_1$ thus to be separated from the primary electron beam. Then, the secondary electron beam is detected by a secondary electron detector 761*p*. The secondary electron detector 761*p* outputs an electric signal representing an intensity of the secondary electron beam entered therein. The electric signal output from this detector 761*p* is input to an image data processing section 771 of a process control system 77*p* after having been amplified by a corresponding amplifier (not shown).

As shown in FIG. 45, the electron gun 71*p*, the axial aligning deflectors 731*p*, 731*p'*, the condenser lens 721*p*, the deflector 733*p*, the Wien filter 726*p*, the objective lens 729*p* and the secondary electron beam detector 761*p* are all accommodated within an optical column 701*p* having a diameter corresponding to a given area of the wafer W, thus composing a single unit of electron beam scanning and detection system, which is used to scan the circuit pattern on the wafer W. In practice, a plurality of dices has been formed on the surface of the wafer W. Other electron beam scanning/detection systems (not shown) each having a similar configuration to the above-described electron beam scanning and detection system is arranged in parallel with the optical column 701*p* so as to be used to scan the same location on a different die on the wafer W.

Although the electron beam scanning and detection system operates in the same manner as in the preceding explanations, what is different is that the electric signal output from the secondary electron detection system of each of the electron beam scanning/detection systems, which is constructed as one beam/one detector per one optical column, is entered into the image data processing section 771 of the process control system 77. Then, the image data processing section 771 converts the electric signal entered from each of the detection systems into a binary information, and further converts this binary information into an image data with reference to the electron beam scanning signal. To accomplish this, a signal waveform having given to the electrostatic deflector 733*p* is supplied to the image data processing section 771. The image data obtained for each of the dice formed on the surface of the wafer W is compared with a reference die pattern while being accumulated in an appropriate memory. This allows a defect to be detected for every one of the plurality of die patterns formed on the surface of the wafer W.

It is to be noted that similarly to the above-described embodiments, also in the embodiment shown in FIG. 45, a variety of circuit patterns may be used as the reference circuit pattern to be used by the image data processing section 771 for making a comparison with a specific image data representing a certain die pattern on the wafer W, and for example, such image data obtained from the CAD data of the die pattern, to which the scanning has been applied so as to generate said specific image data, may be used.

The Wien filter or the ExB separator 726*p* comprises an electrostatic deflector 728*p* and an electromagnetic deflector 727*p* arranged so as to circumscribe said electrostatic deflector 728*p*. As this magnetic deflector 727*p*, preferably a permanent magnet made of platinum alloy may be used instead of an electromagnetic coil. This is because applying a current in a vacuum environment is not adequate. Further, the deflector 733*p* functions both as the axial aligner for aligning the direction of the primary electron beam with the axis of the objective lens 729*p* and the scanner.

Since the method for fabricating the condenser lens 721*p* and the objective lens 729*p* may be same as the method for fabricating the condenser lens and the objective lens in the embodiment shown in FIG. 41, a detailed explanation thereof will be omitted.

As described before, since the condenser lens 721*p* and the objective lens 729*p* are fabricated by way of machining the ceramic, it is possible to process those lenses with high level of precision and to reduce the outer diameters thereof. Accordingly, if the outer diameters of the condenser lens 2 and the objective lens 729*p* are reduced to, for example, not greater than 20 mm, then six or eight electron beam apparatuses can be arranged for one piece of wafer by employing such an array of the optical column as shown in FIG. 42 in the case of the inspection of the wafer having a diameter of 200 mm with a range for inspection defined by a diameter of 140 mm, the throughput in increased by 6 or 8 times.

Figure 46:
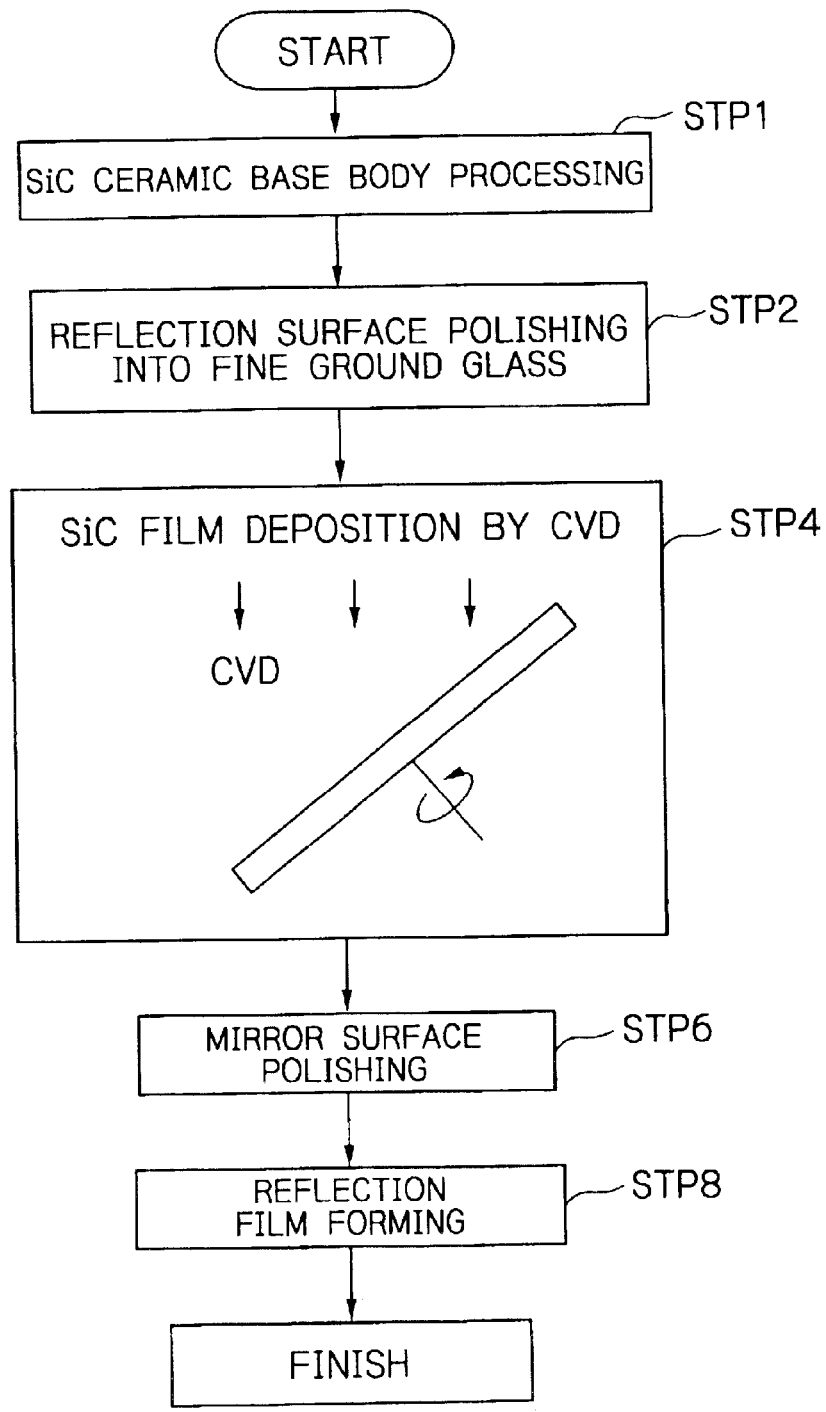
FIG. 46 is a block diagram illustrating a preferred manufacturing process of a laser reflection mirror shown in FIG. 44.

It is to be appreciated that the laser reference reflection mirrors to be mounted on the objective lens and the stage unit may be fabricated according to the fabrication processes shown in FIG. 46.

In the method, as shown in FIG. 46, primarily SiC ceramic was processed to have a dimension defined by a sectional area of 30 mm×30 mm and a length of 35 cm (STP 1). A laser reflecting surface thereof was ground to be a fine obscured glass like face having a rough but high flatness surface (STP 2). Subsequently, a CVD apparatus was used to apply a film deposition thereto up to a level to fill in sufficiently a void on the reflecting surface due to a void formed inside thereof and the rough surface (20 μm thick in one example) (STP4). In that stage, in order to fill in the void and the like efficiently, the mirror was inclined so as to form an angle of approximately 45 degrees between the vertical line and the reflecting surface and left in this condition for a long time period thus to form the film.

After that, a mirror polishing was applied to the object (STP 6). Since the surface prior to the deposition by the CVD was in the fine obscured glass like condition, even at the time of polishing, there would never occur a separation between the main body and the CVD film. After the mirror polishing, a multi-layer reflection film or titanium, gold or the like was used to form a reflecting film (STP 8).

Further Alternative Embodiment of Electron Beam Apparatus

Figure 47:
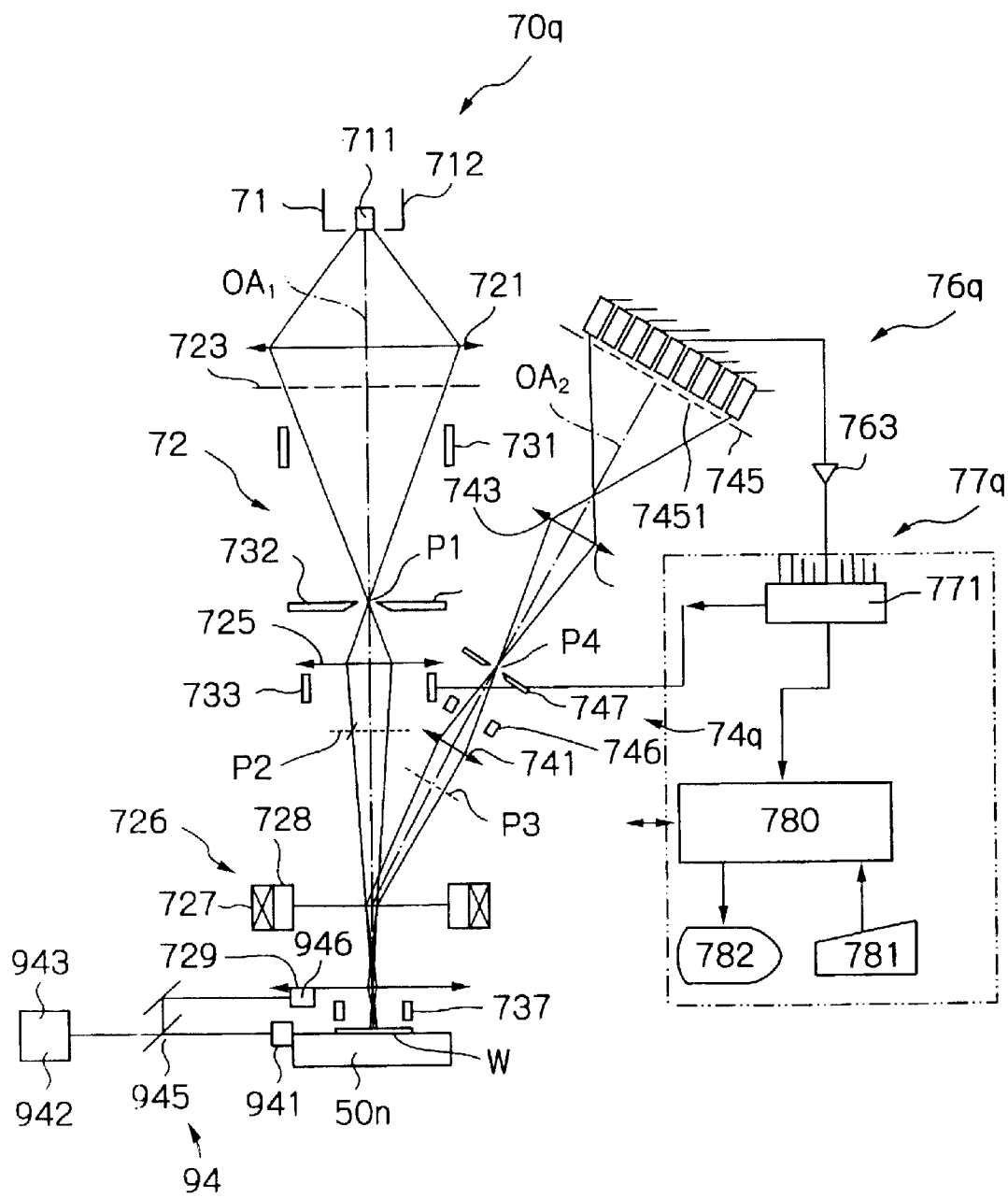
FIG. 47 is a diagram illustrating a general configuration of still another embodiment of the electron beam apparatus according to the present invention.

FIG. 47 shows an alternative embodiment of the electronic optical apparatus or the electron beam apparatus designated generally by reference numeral 70q. In FIG. 47, the same components as those in the electron beam apparatus shown in FIG. 43 are designated respectively by the same reference numerals and detailed explanations on the structure and function thereof will be omitted. Besides, components different from but similar to those in FIG. 43 are designated respectively by the same reference numerals, each added with a suffix "q".

The electron beam apparatus according to this embodiment is same as the electron beam apparatus shown in FIG. 43 with the exception that an aperture plate 747 is disposed at a point P4 in a secondary optical system 74q where a cross over is formed, that the secondary optical system comprises an electrostatic deflector 746 and that a detection system comprises a control section 78.

In this embodiment, each of the detectors 761 is connected via each of the amplifier 763 to an image data processing section 771 of a process control system 77q for converting a detection signal into an image data. Since the image data processing section 771 is supplied with the same scanning signal as that given to a deflector 733 for deflecting the primary electron beam, the image data processing section 771 can figure out a secondary electron pattern image for a pattern formed on a wafer W from the detection signal obtained during the beam scanning.

The image data processing section 771 is operatively connected with the control section 780 so as to be capable of performing a data communication therebetween. This control section 780 executes an evaluation on the wafer W based on the secondary electron pattern image generated by the image data processing section while controlling and managing the whole electron beam apparatus.

The control section 780 is connected with a display section 782 for indicating an evaluation result or the like and an input section 781 for entering a command of an operator. The display section 782 may be made up of a CRT or a liquid-crystal display and may indicate a defective pattern, a secondary electron pattern image, the number of defective locations and so on.

The wafer W may be placed on a stage unit 50n. This stage unit is configured such that it can move within a horizontal plane in the X and the Y directions with the wafer W placed thereon in response to the command from the control section 78. That is, the stage unit 50n enables the wafer W to move in the X and the Y directions with respect to the primary and the secondary optical systems. Since a laser interferometer 94 to be arranged in conjunction with the stage unit and an objective lens has the same structure and function as those of the apparatus shown in FIG. 43, detailed explanations thereof will be omitted.

A laser reflection mirror 941 provided in the form of a movable mirror requires to be at least 30 cm long for evaluating a 12-inch wafer W, and to be further longer for the YAW measurement or for aligning an optical axis $OA_1$ of the primary optical system onto a fixed marker or a Faraday cup of the stage device 50n, being around 40 cm long in most cases. In the present embodiment, a base body of such a long laser reflection mirror 941 is made of highly rigid SiC ceramic without increasing the thickness thereof. If a side face of a top surface member of the stage device is formed as the reflection mirror, then the rigidity can be further improved.

Preferably, a laser reflection mirror 946 provided in the form of a reference mirror may be attached to a ring, which is made of ceramic having a coefficient of linear expansion almost equal to 0 and has been attached to an outer cylinder of the objective lens 729, in order to avoid an affection from thermal expansion of the optical column. This reference mirror 946 may be made of SiC ceramic similarly to the movable mirror 941.

An operation of the electron beam apparatus according to the present embodiment will now be described. As can be seen obviously from FIG. 47, since a portion in the optical path common to the primary optical system and the secondary optical system is the portion from an ExB separator 727 through the objective lens 729 up to the wafer W, the number of common optical parts has been successfully decreased. Owing to this, even if the lens condition for the objective lens 729 was matched to the primary electron beam, a focusing condition for the secondary electron beam can be adjusted by using magnifying lenses 741 and 743. In addition, although the axial alignment with respect to the objective lens 729 is performed favorably to the primary electron beams by applying an axial aligning power supply voltage onto the deflector 733 in superposition to its due voltage, the axial mismatch of the secondary electron beam due to the axial alignment favorable to the primary electron beam can be compensated for by using the axial aligner for the secondary optical system or the electrostatic deflector 746.

As for the aperture plates 735, 747 defining numerical apertures, two aperture plates has been employed, one of which is disposed at the location where the first cross over image is formed (an installation point of an opening aperture 4) and only the primary electron beam passes therethrough, and the other of which is disposed at the location where the second cross over image is formed (an installation point of an opening aperture 747) and only the secondary electron beam passes therethrough, thereby allowing an optimal aperture diameter to be selected individually. Employing a size of an aperture of the objective lens 729 sufficiently greater than the diameter of the cross over herein and zooming the objective lenses 721 and 725 so as to make the cross over size variable at the position of the objective lens 729 can make an angular aperture selectable. This allows the angular aperture to be adjusted to a desired optimal value within a range determined by the trade-off between the low aberration and the high beam current by only using an electric signal without exchanging apertures.

As for the location of the aperture of the secondary optical system, such a condition should be satisfied that the secondary electron image could be focused on the detector 761 by the lenses 741 and 743. Then, the aperture is to be moved along the optical axis (Z) until the location where every secondary electron beam may have the same intensity when the wafer with the inspected surface having a uniform emission characteristic has been used, and at that location, the aperture of the secondary optical system should be fixed. This position is the location in the optical axis direction where the principal ray from the wafer would cross the optical axis as illustrated.

A process for obtaining the secondary electrons is as follows. The primary electron beam emitted from the electron gun 71 is focused by the condenser lens 721 to form a cross over at a point P1. Since, passing through a plurality of apertures 7231 of the first multi aperture plate 723 on the way to the point P1, the primary electron bean is formed into a plurality of beams. The plurality of beams is focused on a point P2 by the reduction lens 725 and further focused through the objective lens 729 to be formed into an image on the wafer W. Thus, on the wafer W, a plurality of irradiation spots each having almost the same intensity is formed by the primary electron beam, and then the secondary electrons are emitted from those irradiation spots respectively. During this period, the electrostatic deflector 733 deflects the primary electron beam so as to scan a certain region slightly larger than the spacing between adjacent two beams. This deflection allows the irradiation spots on the wafer to scan in the beam aligning direction with no region left not-scanned.

The multi-beam consisting of the secondary electrons emitted from the respective irradiation spots on the wafer is accelerated by the electric field of the objective lens 7 and converged to be narrower, and then reaches to an ExB separator 726, where the multi-beam is deflected by a field (ExB) generated therein into the direction at a specified angle with respect to the optical axis $OA_1$ to proceed along the optical axis $OA_2$ of the secondary optical system 74$q$. The secondary electron image is focused on the point P3 that is closer to the objective lens 729 than the point P2. This is because typically each of the secondary electron beams only has an energy of some eV, while each of the primary electron beams having the energy of, for example, 500 eV on the wafer. The multi-beam consisting of those secondary electron beams is magnified by the magnifying lenses 741 and 743, and after having passed through the plurality of apertures 7451 of the second multi-aperture plate 745, each beam of the multi-beam is detected by the detector 761. The detection signal is sent to the image data processing section 771 of the process control system 77$q$ via the amplifier 763 to form the secondary electron image pattern.

The stage unit 50$n$ moves the wafer W sequentially or continuously by a predetermined width synchronously so as to allow the multi-beam to scan the overall surface of the wafer to be inspected. At this point of time, in the laser interferometer 94, a laser oscillator 943 oscillates a laser beam. The oscillated laser beam is split into two beams by a half mirror or a dichroic mirror 945. One of the beams which has passed through the half mirror 945 reaches to the movable mirror 941, while the other beam is reflected by a total reflection mirror 944 and reaches to the reference mirror 946, thus each of two beams being reflected. The beam reflected by the movable mirror 941 passes through the half mirror 945 and guided to a receiver or a laser interferometer 942, while the beam reflected by the reference mirror 946 is reflected again by the total reflection mirror 944 and the half mirror 945 to be guided to the receiver 942. Thus, the receiver 942 detects an interference light of the reflected beams from the movable mirror 941 and the reference mirror 946. The detection signal is sent to the control section 780, where a distance between the movable mirror 941 and the reference mirror 946 along the X and Y directions, i.e., an XY coordinate position of the X and the Y tables of the stage unit 50$n$, is calculated based thereon.

The control section 780, based on the XY coordinate position of the X and the Y tables of the stage unit 50$n$, controls the movement of the stage unit 50$n$ so as to inhibit any area from being left not-scanned with the multi-beam. In the present embodiment, since the base bodies of the laser reflection mirrors 941, 946 have been made of highly rigid SiC, the flatness of the mirror surfaces can be maintained highly precisely without increasing the thickness thereof. This enables the highly precise position control of the stage unit 50$n$, thus allowing the accurate secondary electron beam image to be obtained. Besides, the laser reflection mirror which has been made thin is space-saving. Further, the movable mirror 941 which has been made lighter in weight can reduce the load in moving the stage.

Based on the secondary electron beam image pattern formed in the manner as described above, the control section 780 performs, for example, an evaluation of the wafer as follows.

In a defect inspection method by way of the pattern matching applied to the wafer W, the control section 780 makes a comparative matching between a secondary electron beam reference image for a wafer having no defect, which has been stored in the memory in advance, and an actually detected secondary electron beam image and calculates a similarity therebetween. For example, if the similarity indicates a value not greater than a threshold, it is determined that "a defect exists", and if the similarity indicates a value greater than the threshold, it is determined that "no defect exists". At this stage, the detected image may be displayed on the display section 782. This enables an operator to confirm and evaluate finally on whether or not the wafer is defective. Further, every segmental region within the image may be comparatively matched to one another so as to automatically detect the segmental region having a defect. At this stage, preferably, an enlarged image of the defective region should be displayed on the display section 782.

A method for measuring a line width of a pattern formed on a wafer and a method for measuring a voltage contrast of the pattern may be same as those described before in conjunction with FIG. 24, and the explanations thereof will be omitted.

In FIG. 47, if a blanking deflector 731 is arranged so as to deflect the primary electron beam toward an aperture of the aperture plate 735 disposed in the cross over image formation point at a predetermined cycle and thereby to permit said beam to pass therethrough for a short period and to block it for the rest of the period, which will be repeated, then it will be possible to form a bundle of beams having a short pulse width. If such a beam having a short pulse width is used to measure the potential on the wafer as described above, the device operation can be analyzed with high time resolution. That is, the present electron beam apparatus can be used as what is called an EB tester.

Further Alternative Embodiment of Electron Beam Apparatus

Figure 48:
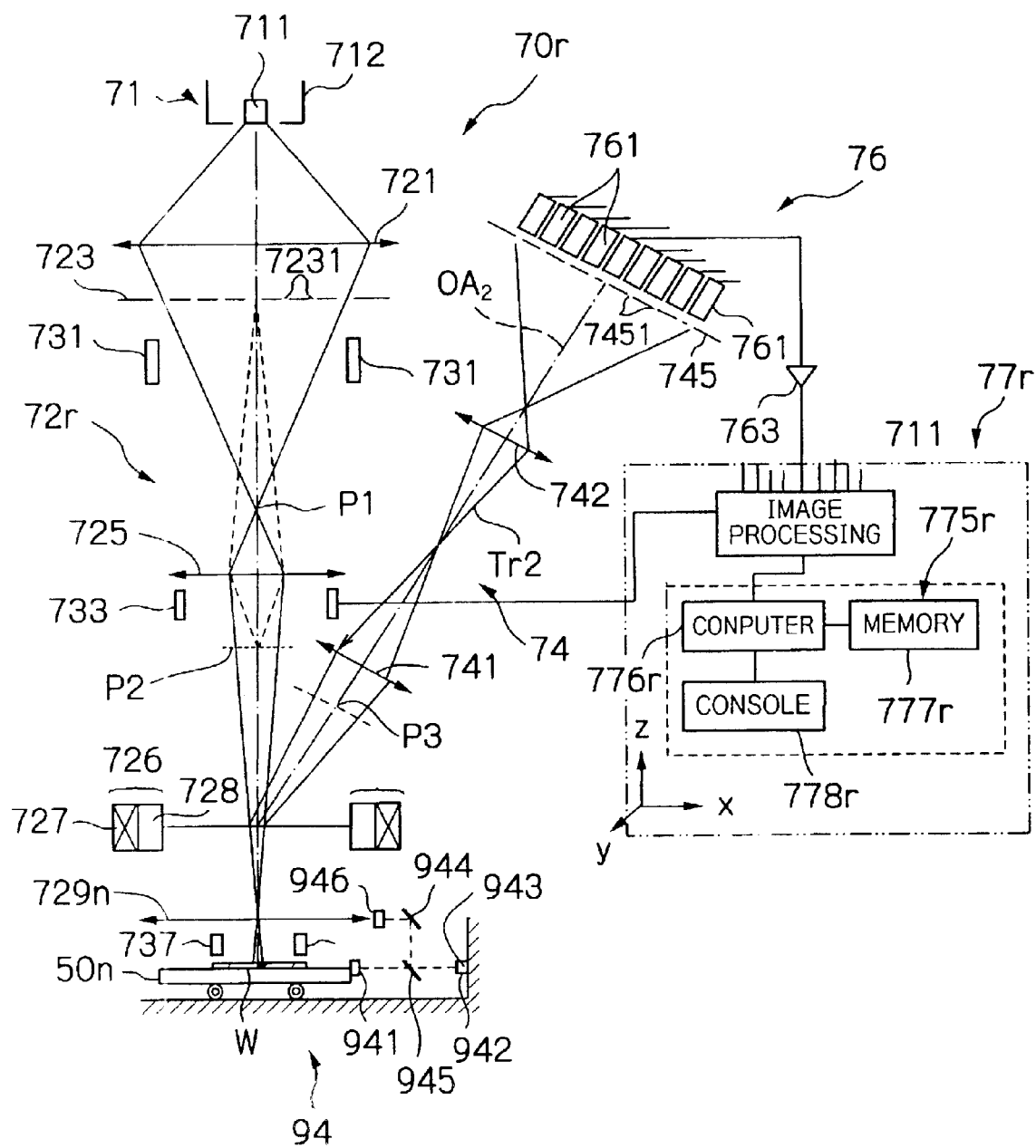
FIG. 48 is a diagram illustrating a general configuration of still another embodiment of the electron beam apparatus according to the present invention.
Figure 49A:
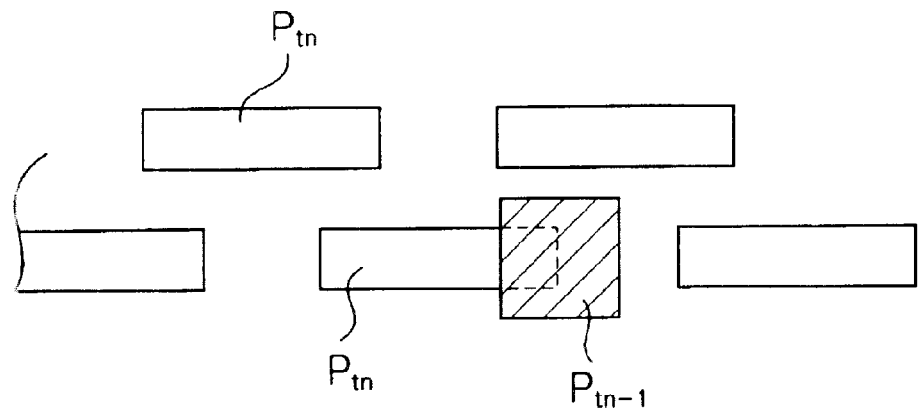
FIG. 49 illustrates how to discriminate a killer defect from a non-killer defect in an inspection by the electron beam apparatus of FIG. 48.
Figure 49B:
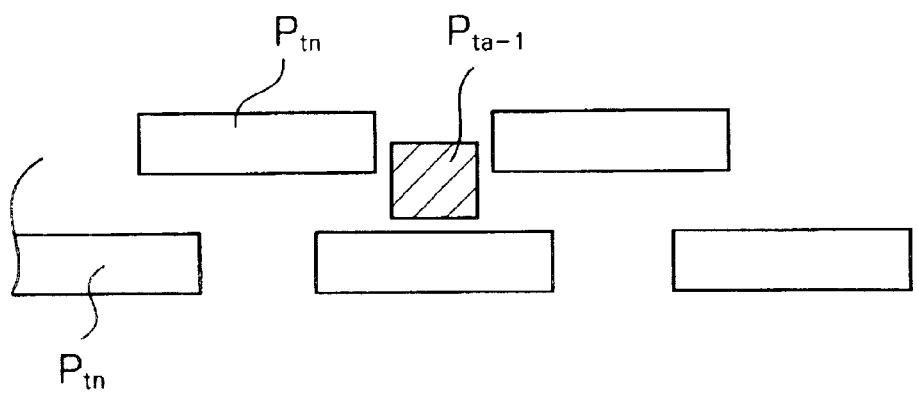
Figure 49C:
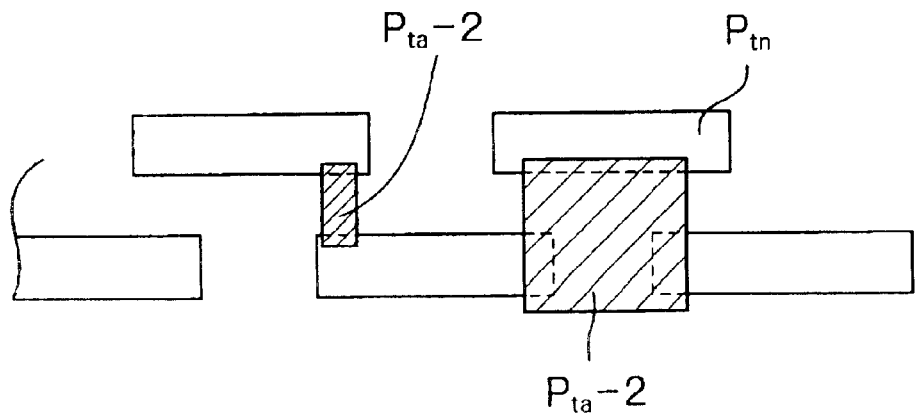

FIGS. 48 and 49 show an alternative embodiment of the electronic-optical apparatus or the electron beam apparatus designated generally by reference numeral 70r. In FIGS. 48 and 49, the same components as those in the electron beam apparatus shown in FIG. 43 are designated respectively by the same reference numerals and detailed explanations on the structure and function thereof will be omitted.

The electron beam apparatus according to the present embodiment is same as the electron beam apparatus shown in FIG. 43 with the exception that a detection system thereof comprises a control unit 775r similar to the mode determining circuit arranged in the electron beam apparatus shown in FIG. 40. Accordingly, the following discussion is directed only to the part relating to the detecting and scanning.

Each of the detectors 761 outputs an electric signal representing an intensity of an incident secondary electron beam thereto. Each of those electric signals, after having been amplified by each corresponding amplifier 763, is input to an image data processing section 771 of a process control system 77r. The image data processing section 771 converts the electric signal supplied from each of the amplifiers 763 into an image data. This can be done because the image data processing section 771 is also supplied with a scanning signal having given to an electrostatic deflector 733 for deflecting the primary electron beam. Thus, the image data processing section 771 outputs a set of image data for respective circuit patterns formed on a wafer W all at once.

A plurality of image data output from the image data processing section 771 is sequentially stored into a memory 777r under a control of a computer 776r running according to an operational command from a console 778r. The memory 777r comprises an image memory section for accumulating the plurality of image data obtained sequentially corresponding to the scanning of the circuit pattern in this way, a reference pattern database for accumulating reference patterns to be used for comparing with the image data obtained by the scanning and thereby determining whether or not an irregular pattern exists, and a determining pattern database for accumulating patterns to be used for determining killer defects and other patterns to be used for determining non-killer defects. With this configuration, the computer 776r can work out to compare the image data obtained from a certain circuit pattern with that of the reference pattern and to distinguish the killer defect from the non-killer defect by using said determining pattern database.

Besides, the computer 776r has been programmed to control the scanning of the wafer W with the primary electron beam so that the defect inspection apparatus shown in FIG. 49 may be used to execute an evaluation such as a defect inspection of a pattern formed on a surface of the wafer W. That is, the computer 776r controls an electrostatic deflector 733 and an magnetic deflector 727 of a Wien filter or an ExB separator 726 to work interlockingly so as to scan the surface of the wafer W in the X direction with a plurality of beams, while controlling the stage unit 50n to move the wafer W continuously in the Y direction, thereby accomplishing the scanning of the overall surface of the wafer W.

To explain in more specific, after having controlled the stage unit 50n to move and place the wafer W at a scanning starting end, the computer 776 further controls the stage unit to move continuously in the Y-direction while controlling a plurality of primary electron beams to scan in the X-direction with an amplitude slightly greater than a distance between respective primary electron beams, Lx (shown in FIG. 9). This means that the wafer could have been scanned in the region extending along the Y-direction having a width w equivalent to full scanning distance of the plurality of primary electron beams in the X-direction, and a signal in association with the scanning in said region would be output from a detector 761.

Subsequently, after the X table of the stage unit 50n having been moved in the X-direction by a step equivalent to the width w, the Y table of the stage unit 50n is continuously moved in the Y-direction while controlling the plurality of primary electron beams to scan the wafer W in the X-direction by the distance equivalent to the width w. Thereby, another region of the width w adjacent to the region having been previously scanned would have been scanned both in the X- and the Y-directions. After this, the similar operations may be repeated thus to scan the overall surface of the wafer W, and the signal obtained as a result of scanning operations from the detector 761 may be processed so as to evaluate the wafer W.

It is to be noted that a distance measuring operation of the stage unit is same as that in the embodiment described in conjunction with FIG. 43, and the explanation thereof will be omitted.

If the wafer W is a semiconductor wafer, the following method may be employed to evaluate the wafer W. That is, a marker may be arranged at an appropriate location on the surface of the wafer W, such that only the one electron beam among a plurality of primary electron beams, which has been formed by one aperture of a multi-aperture plate 723, may be allowed to scan said marker and an output from the detector at that time of scanning is extracted thus to detect the position of the marker. Thereby a physical relationship between the wafer W and the primary electron beam can be determined, and therefore if an arrangement of a circuit pattern formed on the surface of the wafer W with respect to the X- and the Y-directions have been determined in advance, a plurality of primary electron beams could be guided to the correct position to meet said circuit pattern and the beams therein could scan the circuit pattern, thereby accomplishing the evaluation of the circuit pattern on the wafer W.

Further, the line width of the pattern on the surface of the wafer W can be measured in such a way that first a pattern to be evaluated on the wafer W is moved by registration to the proximity to the optical axis of the primary optical system and the wafer W is line-scanned with the primary electron beam to detect the secondary electron beam, and then a signal corresponding to this secondary electron beam is detected to extract a signal for evaluating the line width of the circuit pattern on the surface of the wafer W, which is then calibrated appropriately thus to measure the line width of the pattern on the surface of the wafer W.

It is to be appreciated that forming an image of each one of the secondary electron beams on each corresponding one of those apertures of the second multi-aperture plates 745 or, in other words, aligning the orbit of the secondary electron beam, Tr2, with each corresponding one of those apertures of the second multi-aperture plate 745 will be possible if one piece of lens is arranged downstream to the ExB separator 726, which may facilitate said image formation or alignment of the secondary electron beam by changing an excitation of the magnifying lens 743 and shifting the cross over point P3. Although these adjustments may cause a mismatch in the focusing condition for the secondary electron beam, if the aperture of the second multi-aperture plate 745 was formed so as to have a larger diameter, then the secondary electron detection efficiency would not be deteriorated, and accordingly the above adjustments would never cause any disadvantages to the defect inspection.

Now, referring to FIGS. 49 [A], [B], and [C], there will be described how the computer 776r in the electron beam apparatus of FIG. 48 works to distinguish a killer defect from a non-killer defect. As having been described before, as a plurality of semiconductor chips on the wafer W is scanned all at once with a plurality of electron beams, image data representing the circuit pattern on each of the semiconductor chip is accumulated one after another in the memory 777r. Then, the operator, at any appropriate point of time when the memory 777r has stored the accumulated image data for some parts or all parts of each circuit pattern, sends a command to the computer 776r from the console 778r to execute a defect inspection operation. The computer 776r has been programmed to execute in response to said command the operation comprising the steps of:

(1) reading out a part of the image data for the circuit pattern of one of the semiconductor chips and the image data for the reference pattern corresponding thereto from the memory 777r;

(2) making a comparison between said two image data;

(3) as a result of the comparison, identifying a normal pattern and an abnormal pattern and then taking out the image data containing the abnormal pattern;

(4) comparing said taken-out image data with the contents of the determining pattern database in the memory 777r and determining whether the abnormal pattern is considered to be the killer defect or the non-killer defect;

(5) subsequently, executing said steps from (1) to (4) for all other parts of the image data obtained from the scanning thus to end the defect inspection of the circuit pattern for the current semiconductor chip; and then (6) repeating said steps from (1) to (5) for the image data obtained from the scanning for every remaining semiconductor chips one by one, thus to complete the defect inspection for all of the semiconductor chips to be inspected.

Herein, there will now be described an algorithm for determining whether the location determined to be the abnormal pattern is the killer defect or the non-killer defect. This algorithm is based on such an empirical rule that "although the obtained image data is representative of the abnormal pattern, it should be considered with a considerably high probability that said location is actually of a conductive material". Then, it is assumed that as the result of the scanning of a certain circuit pattern, three kinds of images as shown in FIGS. 49 [A], [B] and [C] were obtained as the images including the abnormal patterns. In the drawings, those white rectangular portions Ptn without hatching are the images representative of the normal patterns and those rectangular portions Pta-1, Pta-2 with hatching are the images representative of the abnormal patterns. Among those rectangular patterns corresponding to the abnormal patterns, the rectangular portion Pta-1 shown in [A] is in contact with a single rectangular portion Ptn, the rectangular portion Pta-1 shown in [B] has no contact with any rectangular portions Ptn, and the rectangular portions Pta-2 shown in [C] are in contact with two or more rectangular portions Ptn, respectively. Then, based on said empirical rule, the algorithm determines that the rectangular portions Pta-1 shown in [A] and [B] are the non-killer defects but the rectangular portions Pta-2 shown in [C] are the killer defects.

With respect to an image of a contact hole layer, the computer 776r works according to said algorithm to determine that an abnormal pattern overlapping with the contact hole is a killer defect and an abnormal pattern having no contact with the contact hole is a non-killer defect. Besides, with respect to an image of a gate layer, the computer 776r works to determine such that an abnormal pattern located within the predetermined range proximal to the gate pattern is indicative of a killer defect and therefore the abnormal pattern located away from the gate pattern by a predetermined distance or much farther is a non-killer defect.

It is to be appreciated that the determining pattern database within the memory 777r may be updated by adding a newly found abnormal pattern at each time when the new abnormal pattern is found so as to be determined on whether it is the killer defect or the non-killer defect during the computer 776r being operative for the defect inspection.

Further Alternative Embodiment of Electron Beam Apparatus

Figure 50:
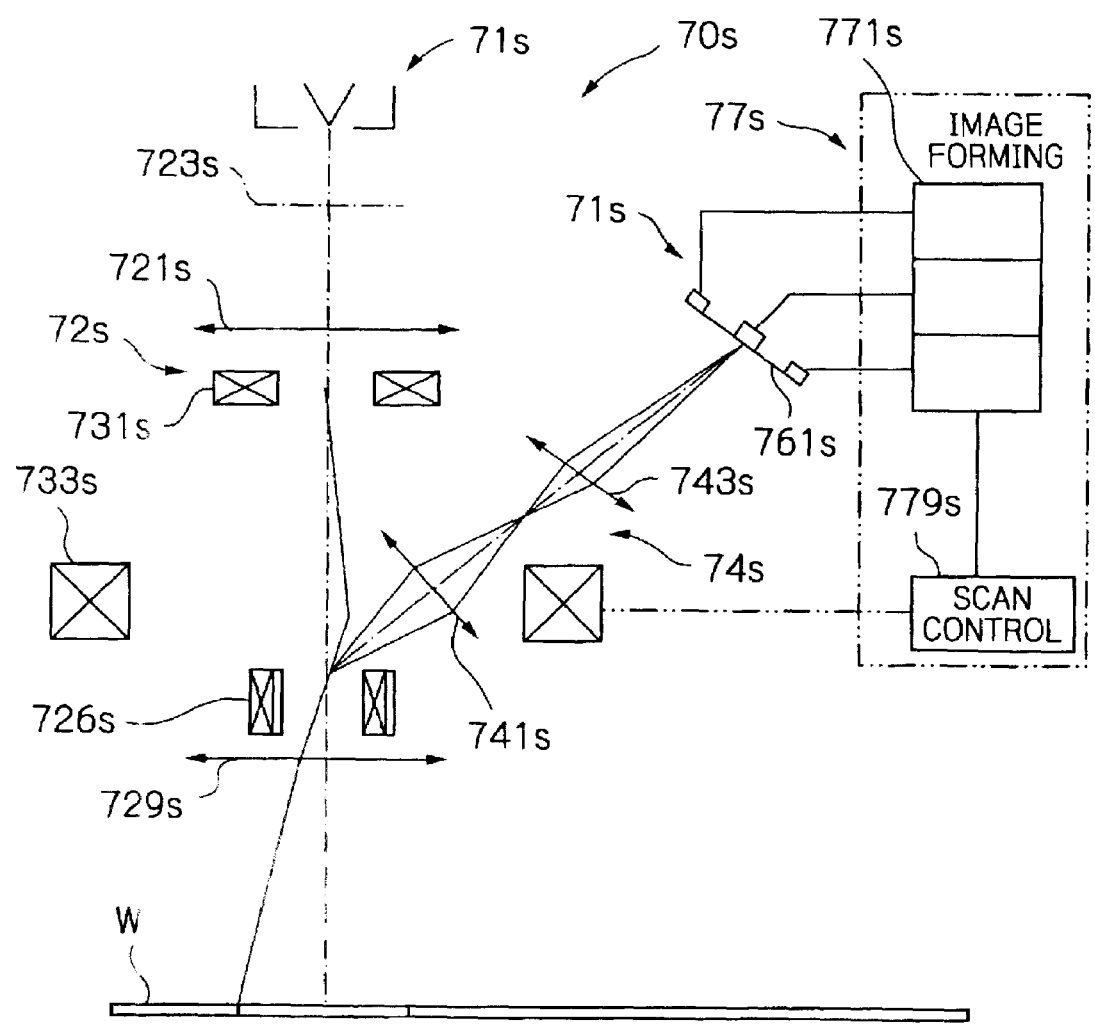
FIG. 50 is a diagram illustrating a general configuration of still another embodiment of the electron beam apparatus according to the present invention.
Figure 51A:
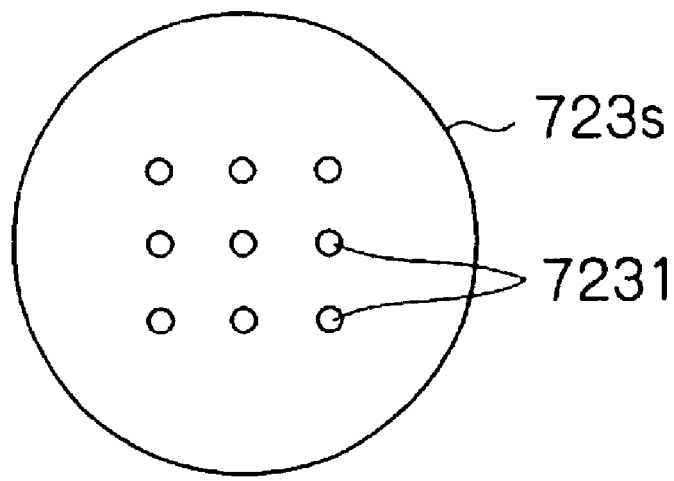
FIG. 51 illustrates an aperture plate having a plurality of apertures installed in the electron beam apparatus shown in FIG. 50.
Figure 51B:
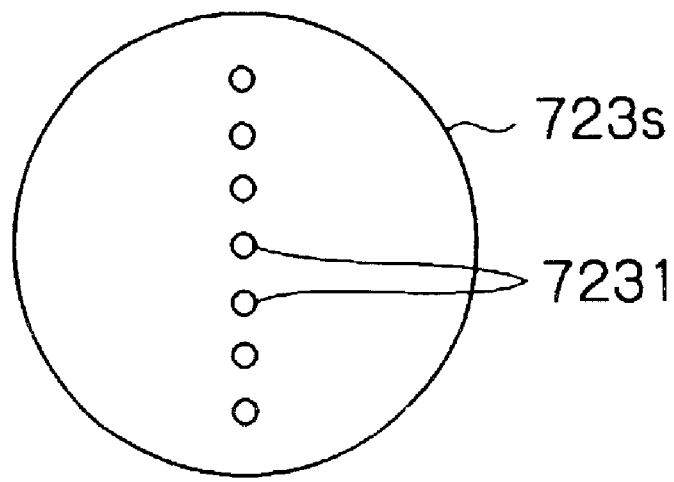
Figure 52A:
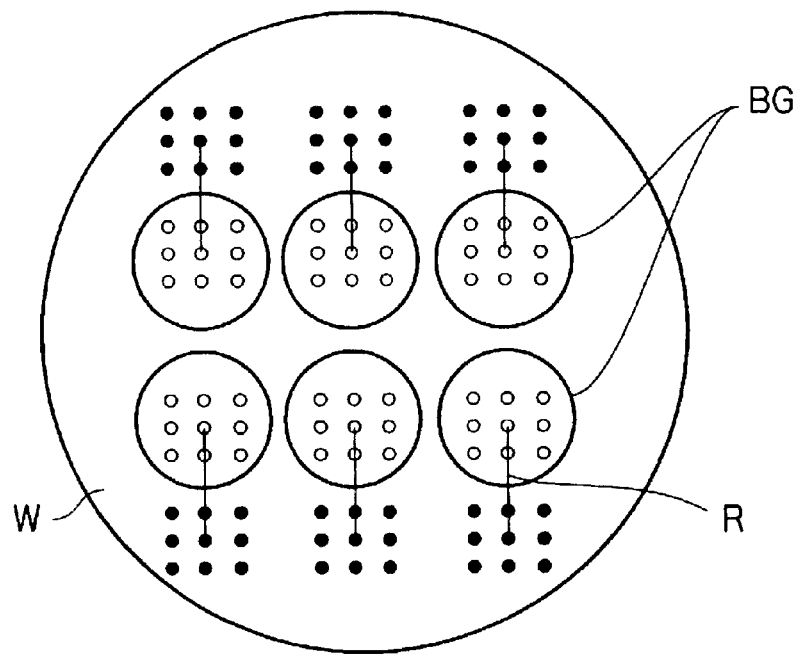
FIG. 52 illustrates an example in which is arranged a plurality of optical systems each having an integrated electron beam apparatus according to the present invention.
Figure 52B:
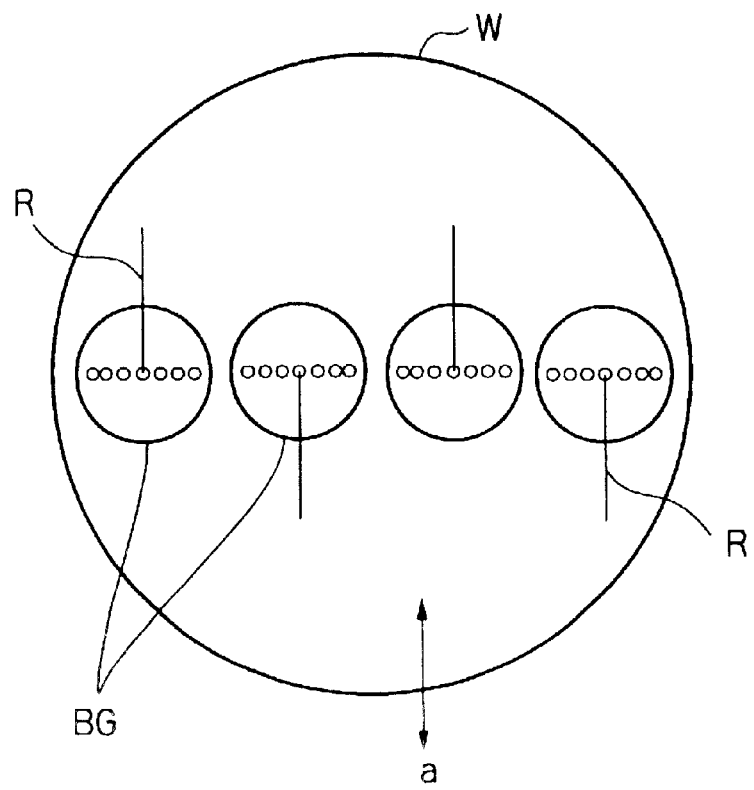

FIGS. 50 to 52 show an alternative embodiment of the electronic optical apparatus or the electron beam apparatus designated generally by reference numeral 70s. In FIGS. 50 to 52, the same components as those in the electron beam apparatus shown in FIG. 8 are designated respectively by the same reference numerals and detailed explanations on the structure and function thereof will be omitted.

In FIG. 50, an electron gun for emitting an electron beam is designated by reference numeral 71s, a primary optical system by 72s, a multi-aperture plate provided with a plurality of small apertures by 723s, a lens by 721s, electromagnetic deflectors by 731s and 733s, an ExB separator by 726s, an objective lens by 729s, a secondary optical system by 74s, lenses by 741s and 743s, and a detector for detecting a secondary electron beam by 761s. Reference numeral 771s designates an image forming unit of a process control system 77s, and 779s designates a scanning control unit, which functions to supply the deflectors 731s and 733s with scanning signals for scanning the electron beam. The multi-aperture plate 723s may be provided with, for example, nine apertures (3×3) as shown in FIG. 51 [A] or seven apertures (1×7) as shown in FIG. 51 [B]. It is to be appreciated that the arrangement and the number of those apertures are not limited to those illustrated in FIG. 51, but any aperture pattern may be arbitrarily employed if appropriate.

In the apparatus shown in FIG. 50, an electron beam emitted from the electron gun 71s is formed into a plurality of beams by a plurality of apertures of the aperture plate 723s, and these beams are formed into images on a surface of a wafer W through the lenses 721s and 729s, while simultaneously the plurality of electron beam is controlled by the deflectors 731s and 733s so as to scan the surface of the wafer W. Under the condition where a stage holding the wafer W has been fixed, the scanning control unit 779s controls the deflectors 731s and 733s to cause the electron beams to scan in the X-axis and the Y-axis directions. Thereby, with the wafer W being fixed, between those spots having formed on the wafer surface at the point of time $t_0$, other spots are sequentially formed at the points of time $t_1$, $t_2$, ..., and in this way, eventually the electron beam spots are formed at all of the points within a predetermined area on the surface of the wafer W. Then, the stage with the wafer W loaded thereon is moved, and another area adjacent to the previously scanned area is similarly scanned.

A secondary electron beam emitted by forming an image of the electron beam on the wafer W is deflected by the ExB separator 726s, and detected by the detector 761s through the lenses 741s and 743s of the secondary optical system, where the detected beam is converted into an electric signal and is supplied as a detector output signal to the image forming unit 771s.

In the apparatus shown in FIG. 50, for example, the multi-aperture plate 723s provided with nine apertures as shown in FIG. 51 [A] is used to form nine electron beam spots on the surface of the wafer, and accordingly the detector 761s is provided with nine detecting elements corresponding to the array of the apertures of the multi-aperture plate 723s so as to detect the secondary electron beams from those nine spots respectively.

The image forming unit 771s is also supplied with the scanning signal from the scanning control unit 779s, and the detector output signal is associated with the scanning signal and stored in an image data memory (not shown) as a signal representative of a pixel position. With this signal, the image forming unit 771s can form a surface image of the wafer W.

The image representing the wafer surface which has been formed in such a manner as described above is compared in a mismatch/match detecting unit (not shown) as per pixel with a reference image pattern or an image pattern with no defect stored in advance, and if any mismatching pixel is found out, then it may be determined that the wafer has a defect. Further, the image representing the wafer surface may be displayed on the monitor screen, and in that case an experienced operator or the like may monitor the image to inspect the wafer surface for any defects.

Still further, upon measuring a line width of a wiring pattern or an electrode pattern formed on a wafer, a pattern area to be evaluated is moved to a location on or near to an optical axis and said area is line-scanned to take out an electric signal to be used for evaluating the line width, and then the signal is calibrated as needed thereby to detect the line width.

With an evaluation apparatus having such a structure as above, the present invention has suggested a method for inspecting the wafer surface which has been processed by a processing apparatus, in which the evaluation apparatus is arranged in the proximity to the processing apparatus and further a controller (not shown) controls an overall operation of the evaluation apparatus to inspect only a region consisting of a predetermined location or a plurality of predetermined areas on the wafer surface so that an inspection time for a wafer may be made approximately equal to a processing time per wafer of said processing apparatus. In this control, at first the wafer is secured onto the stage of the evaluation apparatus, and then minimal required evaluation parameter of a wafer and a processing time required per wafer are input into the controller of the evaluation apparatus. The evaluation parameter may be, for example, a fluctuation of a minimum line width in the case of the processing apparatus being a lithography apparatus, and a defect inspection in the case of the processing apparatus being an etching apparatus. Subsequently, the controller determines an evaluation area or a region to be inspected on the wafer based on the entered evaluation parameter and the entered necessary processing time so that the time required per wafer for evaluating a processed condition of the wafer may be made within or approximately equal to the processing time required per wafer.

Since the inspection is only applied to the predetermined area and inevitably the range of movement of the wafer W within the evaluation apparatus should be made smaller, therefore a foot print of the evaluation apparatus can be reduced in comparison with the case where the inspection is applied to the entire area on the wafer. Further, since the evaluation time has been made approximately equal to the processing time, and accordingly the throughput of the evaluation apparatus is also approximately equal to that of the processing apparatus, therefore if any defect is found out, it will be more easier to find out any irregular operation in the processing apparatus corresponding to the defective condition.

It is to be appreciated that the inspection apparatus may comprise a plurality of optical column units arranged in an array as shown in FIG. 52, each unit of the optical column including the electron beam apparatus shown in FIG. 50. That is, FIG. 52 [A] schematically shows an array of the electron beam spots on the wafer W in the case of six optical columns arranged in the array of 2 rows×3 columns, each including the multi-aperture plate 723s with nine apertures as shown in FIG. 51[A]. On the other hand, FIG. 52 [B] schematically shows an array of the electron beam spots on the wafer W in the case of four optical columns arranged in line, each including the multi-aperture plate 723s with seven apertures arranged in line as shown in FIG. 51[B].

In FIG. 52, a group of beam spots generated by each of the optical columns is indicated by a circle designated with the reference BG, and a straight line R extending from the center of each circle indicates the direction of the emission of the secondary electron beam in each of the optical columns, that is, the orientation of the secondary electron beam detection system comprising the lenses 741s and 743s and the detector 761s. As shown in FIGS. 52 [A] and [B], the secondary electron beam detection systems have been arranged so as not to interfere with one another, and with such arrangement, a plurality of optical columns may be installed in the efficient manner thus to prevent the foot print for the entire evaluation apparatus from being oversized.

It is to be noted that the arrangement and the number of the plurality of optical columns, as a matter of course, are not limited to those shown in FIGS. 52 [A] and [B]. In the case where the optical columns in the array of 1×N as shown in FIG. 52 [B] is employed, the wafer W may be moved continuously in the direction indicated by the arrow "a", if appropriate.

Also, in the second embodiment using a plurality of optical systems, similarly to the first embodiment, the evaluation apparatus may be placed in the proximal to the processing apparatus and furthermore the control system (not shown) may control the operation thereof such that the inspection time for a wafer can be made approximately equal to the processing time per wafer of said processing apparatus. In that case, the wafer may be inspected with a full-face inspection or with a partial inspection limited to a predetermined region on the wafer surface depending on the processing time, and the important point is that the inspection operation would be controlled such that the processing time per wafer should be approximately matched to the inspection time per wafer. In this case also, the range necessary for moving the wafer can be made smaller, and thereby the foot print for the evaluation apparatus can be reduced. Besides, since the throughput of the evaluation apparatus is made approximately equal to the throughput of the processing apparatus, if a defect is found out, it will be much easier to find out an irregular operation in the processing apparatus.

Further, upon evaluating a processed condition in a processing apparatus with an especially shorter processing time, a sampling inspection on the basis of one for every two wafers or one for every three wafers may be employed so as to make a better matching between the throughputs per lot.

Further Alternative Embodiment of Electron Beam Apparatus

Now, referring to FIGS. 53 to 59, a defect inspection of a pattern formed on a wafer will be described in detail. It is to be noted that in FIG. 53, an embodiment in which an inspection apparatus is applied to what is called an electron beam apparatus of the multi-beam type is designated generally by a reference numeral 70t, and components corresponding to those in the preceding embodiments are designated by the same reference numerals, each added with a suffix "t", wherein explanations of the structure and function of those components will be omitted and only the contents which have been newly added may be explained in detail.

Figure 53:
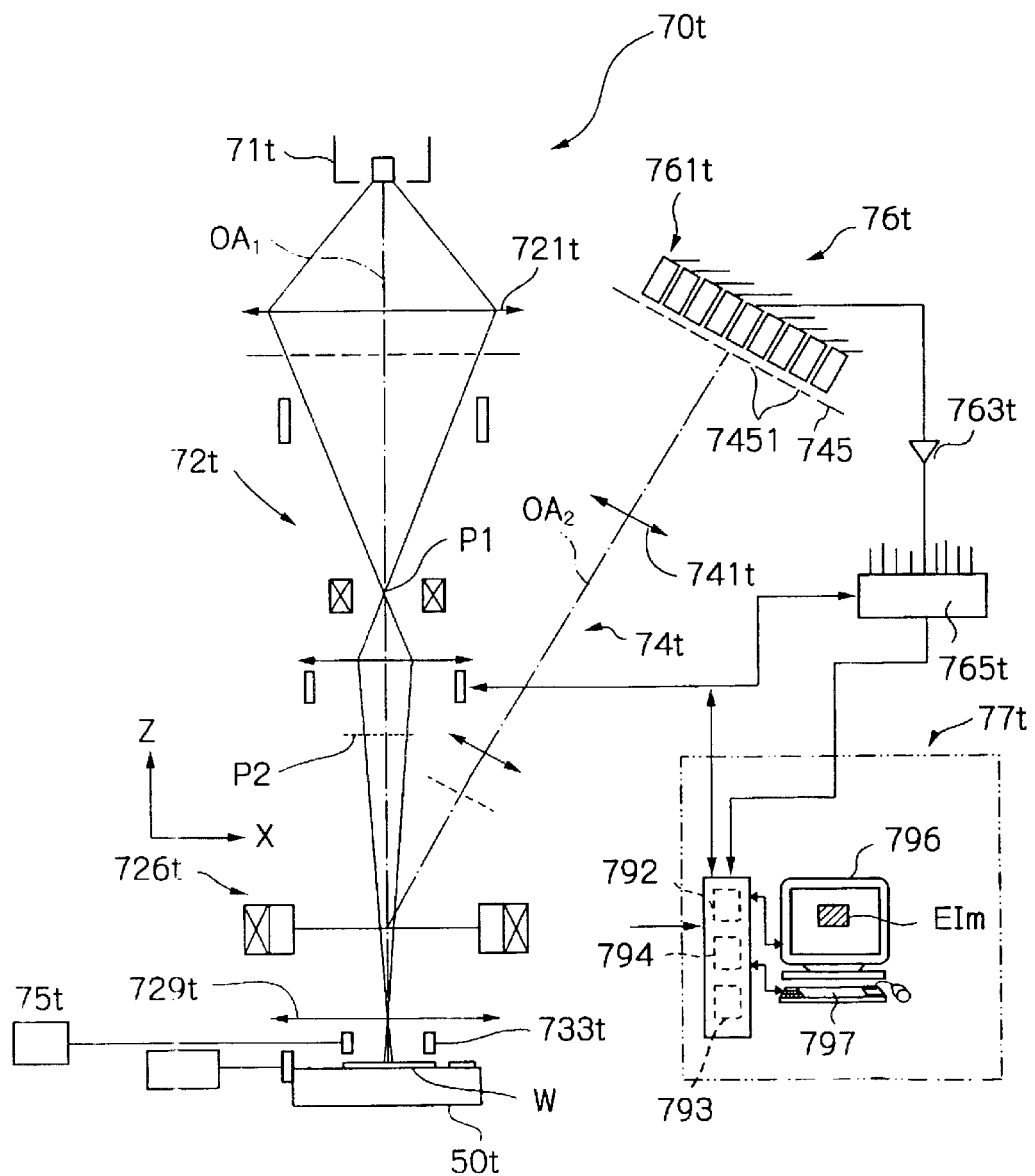
FIG. 53 is a diagram illustrating a general configuration of another embodiment of the defect inspection apparatus using the electron beam apparatus according to the present invention.

In FIG. 53, the reference numeral 71t denotes an electron gun for emitting a primary electron beam, 721t denotes an electrostatic lens for converging the emitted primary electron beam, 726t denotes an ExB deflector which allows the appropriately shaped primary electron beam to advance straight in the field consisting of an electric field and a magnetic field crossing orthogonally with each other so as to impinge upon a semiconductor wafer W at an approximately right angle, 729t denotes an objective lens for forming the deflected primary electron beam into an image on the wafer W, 50t denotes a stage unit capable of moving within a horizontal plane with the wafer W loaded thereon, 741t denotes an electrostatic lens for forming a secondary electron beam emitted from the wafer W by the irradiation of the primary electron beam into an image, and 761t denotes a detector for detecting individually an intensity of each beam for each of the formed images. A signal from the detector 761t is input into an image forming circuit 765t thus to form a secondary electron image. The electron beam apparatus in this embodiment further comprises a process control system 77t for executing an operation for detecting a defect on the wafer W based on the secondary electron image detected by the detector 761t while controlling the whole apparatus. It is to be appreciated that although an image by scattered electrons or reflected electrons may be obtained as said secondary electron image other than the image by the secondary electrons, herein, the case where the obtainment of the secondary electron image is selected will be described exclusively.

Further, a deflecting electrode 733t is interposed between an objective lens 729t and the wafer W for deflecting an angle of incidence of the primary electron beam to the wafer W by the electric field or the like. This deflecting electrode 733t is connected with a deflection controller 75t for controlling an electric field of said deflecting electrode 733t. This deflection controller 75t is connected to the process control system 77t and controls said deflecting electrode 733t so that the deflecting electrode 733t can generate the electric field in response to a command from the process control system 77t. It is to be noted that the deflection controller 75t may be implemented as a voltage controller for controlling a voltage to be applied to the deflecting electrode 733t.

The detector 761t may have any arbitrary structure so far as it can convert the secondary electron image formed by the electrostatic lens 741t into a signal, which can be processed in a subsequent stage.

The process control system 77t may be constituted of a general-purpose personal computer and the like as shown in FIG. 53. This computer may comprise a control section main body 791 for executing a variety of controls and arithmetic processing according to a predetermined program, a CRT 796 for indicating a processing result of the main body 791 and an input section 797 such as a key board or a mouse for enabling an operator to input a command. As a matter of course, the process control system 77t may be constituted of a hardware dedicated to a defect inspection apparatus or a workstation.

The control section main body 791 comprises a variety of control boards, including a CPU, a RAM, a ROM, a hard disk, and a video board. A secondary electron image memory area 792 has been allocated on a memory such as the RAM or the hard disk for storing the electric signal received from the detector 761t, i.e., the digital image data of the secondary electron image for the wafer W. Further, on the hard disk, there is a reference image memory section 793 for storing beforehand a reference image data for the wafer having no defect. Still further, on the hard disk, in addition to the control program for controlling the whole unit of the defect inspection apparatus, a defect detection program 794 is stored for reading the secondary electron image data from the memory area 792 and automatically detecting a defect in the wafer W based on said image data according to the predetermined algorithm. This defect detection program 794, as will be described in more detail later, has such a function that it performs a matching of reference image read out from the reference image memory section 793 to an actually detected secondary electron image in order to automatically detect any defective parts, so that it may indicate a warning to the operator when it determines there is the defect existing. In this regard, the CRT 796 may be designed to display the secondary electron image EIm on the display section thereof.

An operation of the defect inspection apparatus according to the first embodiment will now be described by taking flow charts of FIGS. 55 to 57 as examples.

Figure 55:
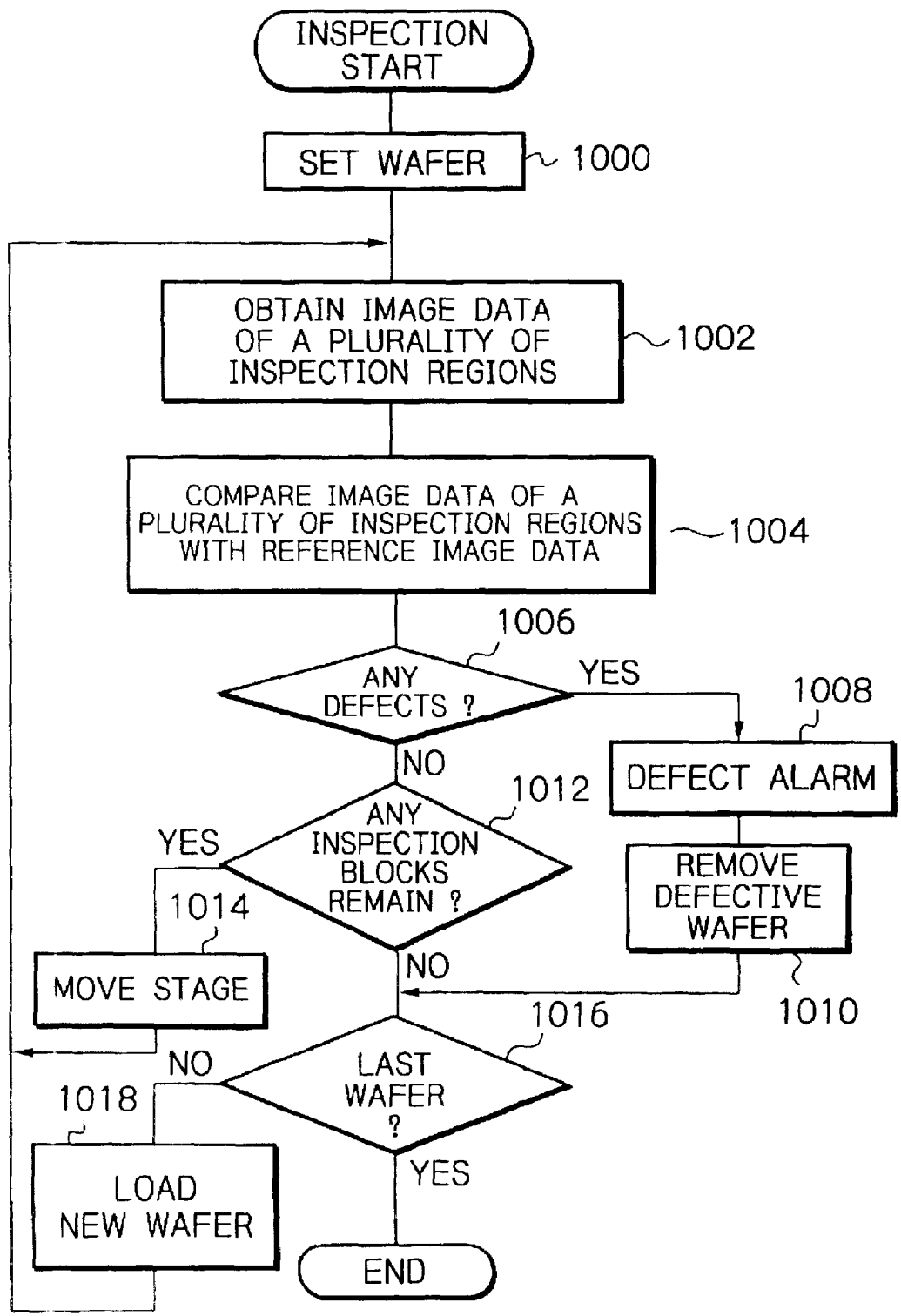
FIG. 55 is a flow chart illustrating a flow of a main routine for wafer inspection in the defect inspection apparatus of FIG. 53.

First of all, as shown in the flow of the main routine of FIG. 55, the wafer W to be inspected is placed on the stage 50t (step 1000). This step may be performed in the mode that the loader automatically sets the wafers W one after another onto the stage unit 50t as explained above.

Figure 54:
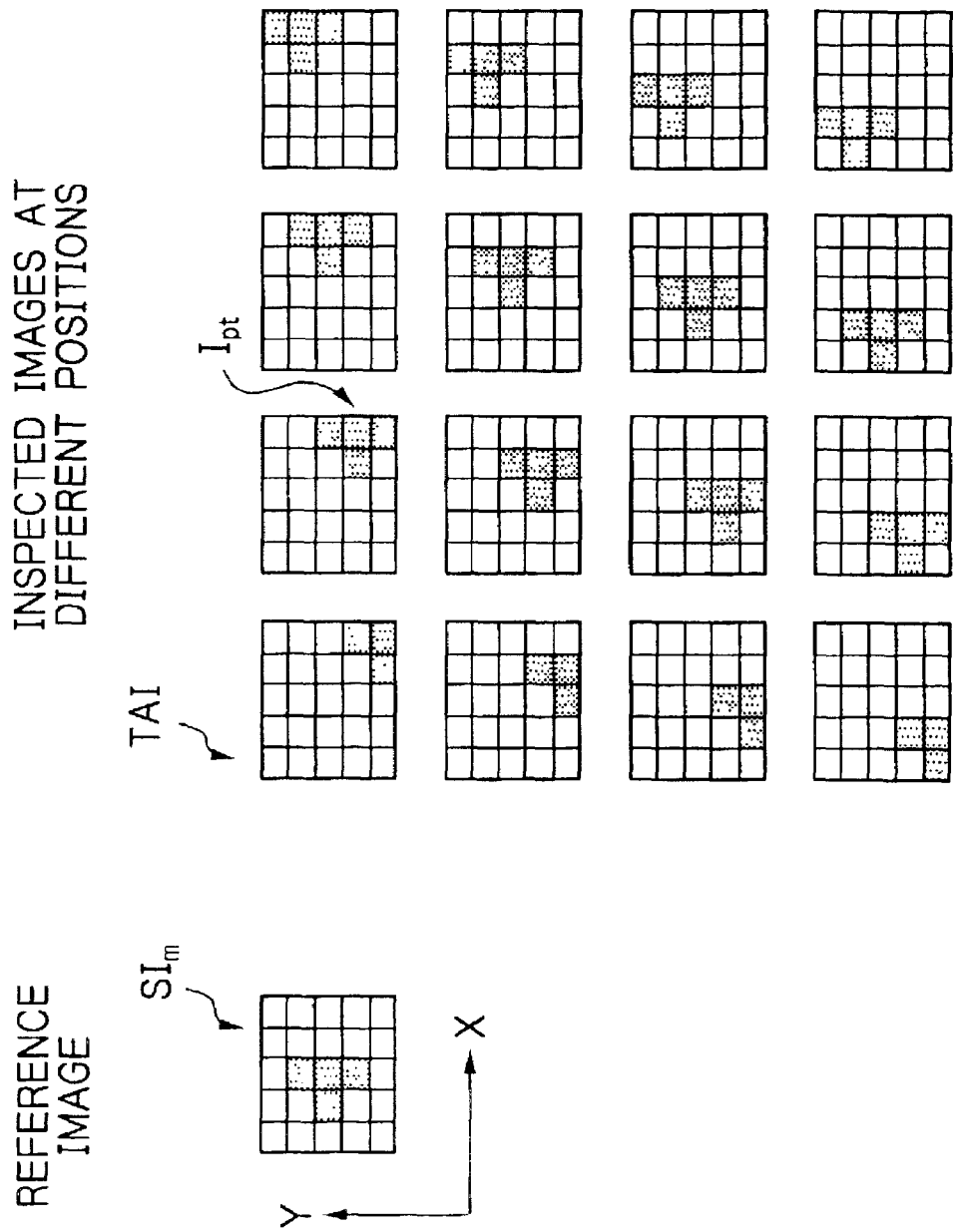
FIG. 54 illustrates an example of a plurality of images to be inspected obtained by the defect inspection apparatus of FIG. 53 as well as a reference image.

Then, images for a plurality of regions to be inspected are respectively obtained, which are displaced one from another while being superimposed partially one on another on the XY plane of the surface of the wafer W (Step 1002). Each of said plurality of regions to be inspected, from which the image is to be obtained, is, for example, a rectangular region on the wafer surface TS to be inspected as designated by reference numerals RA1, RA2, . . . , Rak, . . . in FIG. 59, each of which is observed to be displaced relative to one another while being partially superimposed one on another around the inspection pattern TPt of the wafer. For example, 16 pieces of images TAI for the regions to be inspected (the images to be inspected) may be obtained as shown in FIG. 54. Herein, for the image shown in FIG. 54, each segment of rectangular shape corresponds to one pixel (or a block, whose unit is greater than the unit of pixel), and among those segments, shaded ones correspond to the imaged area of the pattern on the wafer W. This step 1002 will be described in more detail later with reference to the flow chart of FIG. 56.

Then, the image data for the plurality of regions to be inspected, which have been obtained at Step 1002, are compared respectively with the reference image stored in the memory section 793 to look for any matching (Step 1004 in FIG. 55), and it is determined whether or not there is a defect existing in the wafer inspection surface encompassed by said plurality of regions to be inspected. This process performs, what is called, the matching operation between image data, which will be explained later in detail with reference to the flow chart shown in FIG. 57.

If the result from the comparing process at Step 1004 indicates that there is a defect in the wafer inspection surface encompassed by said plurality of regions to be inspected (Step 1006, affirmative determination), the process gives a warning to the operator indicating the existence of the defect (Step 1008). As for the way of warning, for example, the display section of the CRT 796 may display a message notifying the operator that there is a defect, or at the same time may additionally display a magnified secondary electron image EIm of the pattern determined to have the defect. Such defective wafers may be immediately taken out of the stage device to be stored in another storage separately from those wafers having no defect (Step 1010).

If the result from the comparing process at Step 1004 indicates that there is no defect in the wafer W (Step 1006, negative determination), it is determined whether or not there are remained more regions to be inspected for the wafer W currently treated as the inspection object (Step 1012). If there are more regions remained for inspection (Step 1012, affirmative determination), the stage device 50*t* is driven to move the wafer W so that other regions to be further inspected are positioned within the irradiating region of the primary electron beam (Step 1014). Subsequently, the process goes back to Step 1002 to repeat the similar operations for said other regions to be inspected.

If there is no more regions remained to be further inspected (Step 1012, negative determination), or after a drawing out processing of the defective wafer (Step 1010), it is determined whether or not the current wafer treated as the inspection object is the last wafer to be inspected, that is, whether or not there are any wafers remaining for the inspection in the loader, though not shown (Step 1016). If the current wafer is not the last one (Step 1016, negative determination), the wafers having been inspected already are stored in a predetermined storing location, and a new wafer which has not been inspected yet is set instead on the stage device (Step 1018). Then, the process goes back to Step 1002 to repeat the similar operations for said wafer. In contrast, the current wafer is the last one (Step 1016, affirmative determination), the wafer having been inspected is stored in the predetermined storing location to end the whole process.

Then, the process flow of the step 1002 will now be described with reference to the flow chart of FIG. 56.

Figure 56:
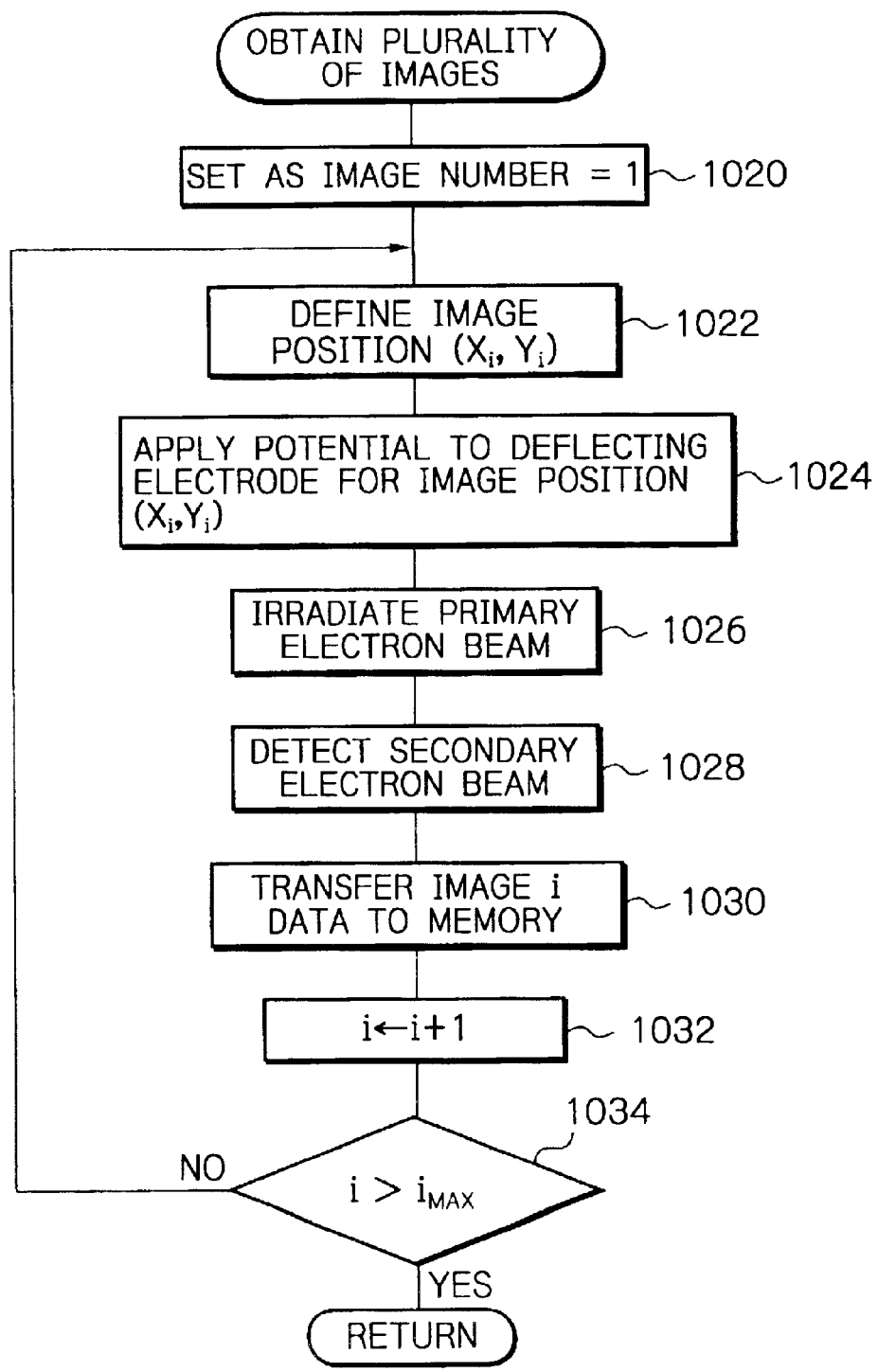
FIG. 56 is a flow chart illustrating a detailed flow of a sub-routine in a process for obtaining a plurality of image data to be inspected in FIG. 55.
Figure 57:
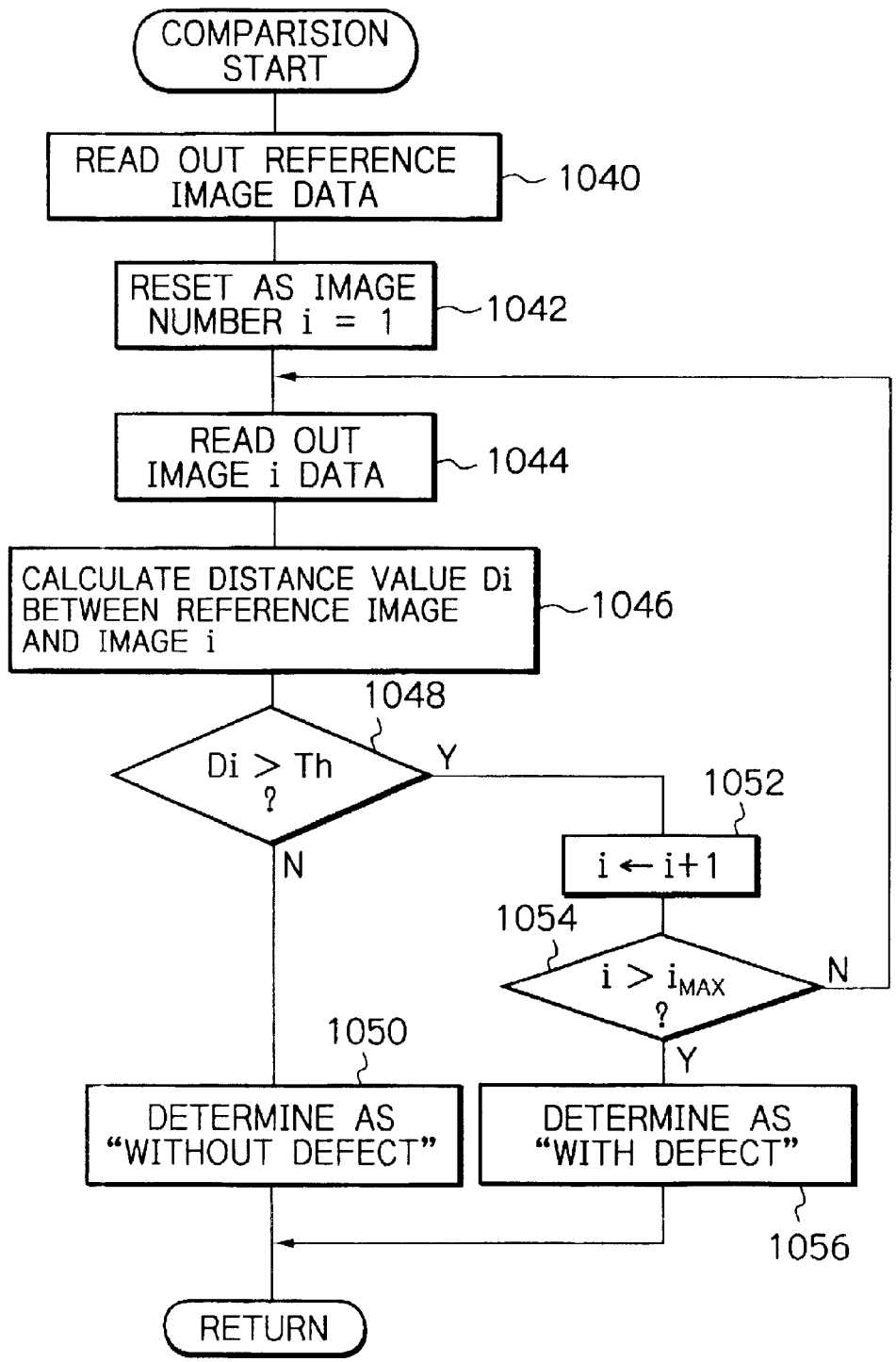
FIG. 57 is a flow chart illustrating a detailed flow of a sub-routine in a comparison process in FIG. 55.
Figure 58:
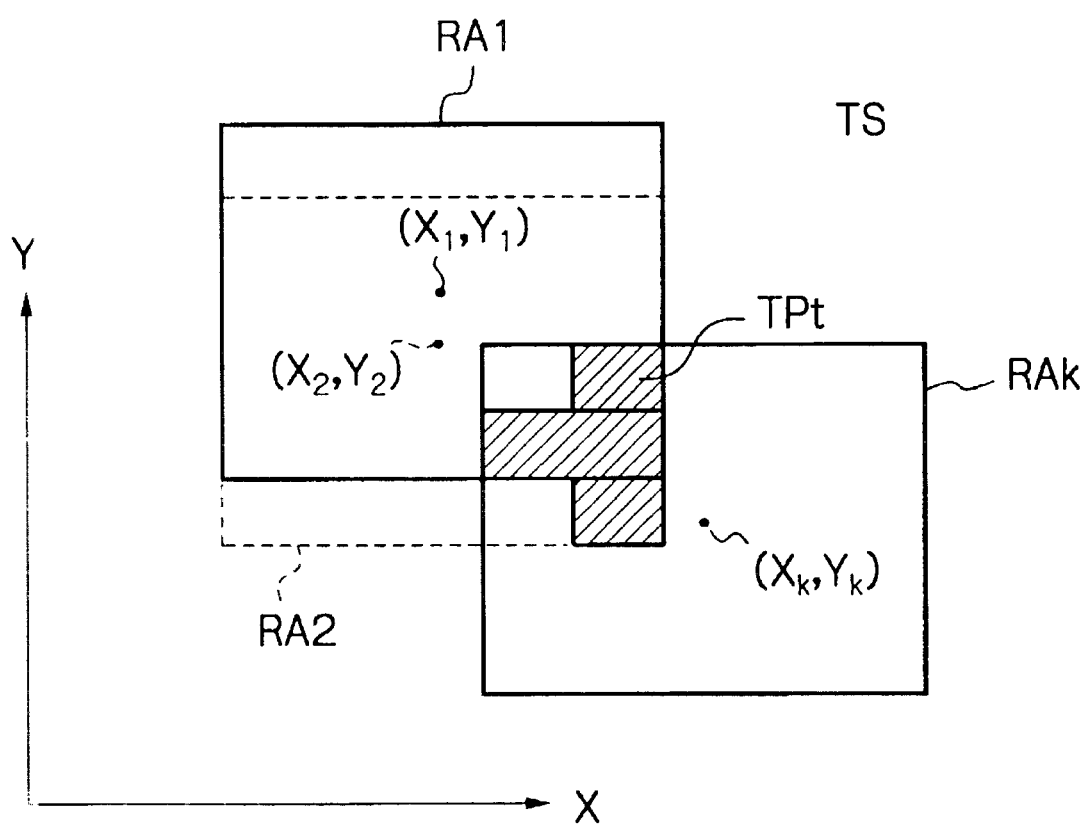
FIG. 58 is a conceptual diagram illustrating a plurality of regions to be inspected, each being displaced from others while partially superimposing with each other on a surface of the semiconductor wafer.

In FIG. 56, first of all, an image number "i" is set to the initial value "1" (Step 1020). This image number is an identification number assigned serially to each of the plurality of images for the regions to be inspected. Secondary, an image position $(X_i, Y_i)$ is determined for the region to be inspected as designated by the set image number i (Step 1022). This image position is defined as a specific location within the region to be inspected for bounding said region, for example, a central location within said region. Currently, i=1 defines the image position as $(X_1, Y_1)$, which corresponds, for example, to a central location of the region to be inspected RA1 as shown in FIG. 59. The image position has been determined previously for every image region to be inspected, and stored, for example, in the hard disk of the process control system 77*t* to be read out at Step 1022.

Then, the deflection controller 75*t* applies a potential to the deflecting electrode 733*t* (Step 1024 in FIG. 56) so that the primary electron beam passing through the deflecting electrode 733*t* of FIG. 53 may be irradiated onto the image region to be inspected in the image position $(X_i, Y_i)$ having determined at Step 1022.

Then, the electron gun 71*t* emits the primary electron beam, which goes through the electrostatic lens 721*t*, the ExB separator 726*t*, the objective lens 729*t* and the deflecting electrode 733*t*, and eventually impinges upon a surface of the set wafer W (Step 1026). At that time, the primary electron beam is irradiated onto the image region to be inspected at the image position $(X_i, Y_i)$ on the wafer inspection surface TS. When the image number i=1, the region to be inspected is RA1.

Secondary electrons are emitted from the region to be inspected, on which the primary electron beam has been irradiated. Then, the generated secondary electron beam is formed into an image on the detector 761*t* with a predetermined magnification by the electrostatic lens 741*t* of the magnified projection system. The detector 761*t* detects the imaged secondary electron beam, and converts it into an electric signal or a digital image data for each detecting element and outputs this signal (Step 1028). Then, the detected digital image data for the image number i is transmitted to the secondary electron image memory area 792 (Step 1030).

Subsequently, the image number i is incremented by 1 (Step 1032), and it is determined whether or not the incremented image number (i+1) is greater than a constant value "$i_{MAX}$" (Step 1034). This $i_{MAX}$ is the number of images to be obtained for inspection, which is "16" for the above example of FIG. 54.

If the image number i is not greater than the constant value $i_{MAX}$ (Step 1034, negative determination), the process goes back to Step 1022 again, and determines again the image position $(X_{i+1}, Y_{i+1})$ for the incremented image number (i+1). This image position is a position shifted from the image position $(X_i, Y_i)$ having determined in the previous routine by a specified distance $(\Delta X_i, \Delta Y_i)$ in the X-direction and/or the Y-direction. The region to be inspected in the example of FIG. 59 is at the location $(X_2, Y_2)$ i.e., the rectangular region RA2 indicated with the dotted line, which has been shifted from the position $(X_1, Y_1)$ only in the Y-direction. It is to be noted that the value for $(\Delta X_i, \Delta Y_i)$ (i=1,2, ... $i_{MAX}$) may have been determined appropriately from the data indicating practically and experimentally how much is the displacement of the pattern TPt on the wafer inspection surface TS from the field of view of the detector 761*t* and the number and the area of the regions to be inspected.

Then, the operations for Step 1022 to Step 1032 are repeated for $i_{MAX}$ pieces of region to be inspected. These regions to be inspected are continuously displaced while being partially superimposed one on another on the wafer inspection surface TS so that the image position after k times of shifting $(X_k, Y_k)$ corresponds to the inspection image region RAk, as shown in FIG. 59. In this way, the 16 pieces of inspection image data exemplarily illustrated in FIG. 54 are obtained into the image memory area 792. It is observed that a plurality of images TAI obtained for the regions to be inspected (i.e., inspection images) contains partially or fully the image Ipt of the pattern TPt on the wafer inspection surface TA, as illustrated in FIG. 54.

If the incremented image number i has become greater than $i_{MAX}$ (Step 1034, affirmative determination), the process returns out of this subroutine and goes to the comparing process (Step 1004) in the main routine of FIG. 55.

It is to be noted that the image data that has been transferred to the memory at Step 1030 is composed of intensity values of the secondary electrons for each pixel (so-called, raw data) detected by the detector 761*t*, and these data may be stored in the memory area 792 after having been processed through various operations in order to use for performing the matching operation relative to the reference image in the subsequent comparing process (Step 1004 of FIG. 55). Such operations includes, for example, a normalizing process for setting a size and/or a density of the image data to be matched with the size and/or the density of the reference image data, or the process for eliminating as a noise the isolated group of elements having the pixels not greater than the specified number. Further, the image data may be converted by means of data compression into a feature matrix having extracted features of the detected pattern rather than the simple raw data, so far as it has not negatively affect on the accuracy in detection of the highly precise pattern. Such feature matrix includes, for example, m×n feature matrix, in which a two-dimensional inspection region composed of M×N pixels is divided into m×n (m<M, n<N) blocks, and respective sums of intensity values of the secondary electrons of the pixels contained in each block (or the normalized value defined by dividing said respective sums by a total number of pixels covering all of the regions to be inspected) should be employed as respective components of the matrix. In this case, the reference image data also should have been stored in the same form of representation. The image data in the context used in the embodiments of the present invention includes, of course, not only a simple raw data but also any image data having the feature extracted by any arbitrary algorithms as described above.

The process flow for Step 1004 will now be described with reference to the flow chart of FIG. 57.

First of all, the CPU in the process control system 77*t* reads the reference image data out of the reference image memory section 793 (FIG. 53) onto the working memory such as the RAM or the like (Step 1040). This reference image is identified by reference numeral SIm in FIG. 54. Then, the image number "i" is reset to 1 (Step 1042), and then the inspection image data for the image number i is reads out onto the working memory (Step 1044).

Then, the read out reference image data is compared with the data of the image "i" for any matching to calculate a distance value "$D_i$" between both data (Step 1046). This distance value $D_i$ indicates a similarity level between the reference image and the image to be inspected "i", wherein a greater distance value indicates the greater difference between the reference image and the inspection image. Any unit of amount may be used for said distance value $D_i$ so far as it may represent the similarity level. For example, if the image data is composed of M×N pixels, the secondary electron intensity (or the amount representative of the feature) of each pixel may be considered as each of the position vector elements of M×N dimensional space, so that an Euclidean distance or a correlation coefficient between the reference image vector and the image "i" vector in the M×N dimensional space may be calculated. It will be easily appreciated that any distance other than the Euclidean distance, for example, the urban area distance may be calculated. Further, if the number of pixels is huge, which increases the amount of the operation significantly, then the distance value between both image data represented by the m×n feature vector may be calculated as described above.

Subsequently, it is determined if the calculated distance value $D_i$ is smaller than a predetermined threshold Th (Step 1048). This threshold Th is determined experimentally as a criterion for judging a sufficient matching between the reference image and the image to be inspected. If the distance value $D_i$ is smaller than the predetermined threshold Th (Step 1048, affirmative determination), the process determines that the inspection plane TS of the wafer W has "no defect" (Step 1050) and returns out of this sub routine. That is, if there has been found at least one image among those inspection images matching to the reference image, the process determines there is "no defect". Accordingly, since the matching operation shall not necessarily be applied to every inspection image, the high-speed judgment becomes possible. As for the example of FIG. 54, it is observed that the image to be inspected at the column 3 of the row 3 is approximately matching to the reference image without any offset thereto.

When the distance value $D_i$ is equal to or greater than the threshold Th (Step 1048, negative determination), the image number "i" is incremented by 1 (Step 1052), and then it is determined whether or not the incremented image number (i+1) is greater than the predetermined value $i_{MAX}$ (Step 1054).

If the image number "i" is not greater than the predetermined value $i_{MAX}$ (Step 1054, negative determination), the process goes back to Step 1054 again, reads out the image data for the incremented image number (i+1), and repeats the similar operations.

If the image number "i" is greater than the predetermined value $i_{MAX}$ (Step 1054, affirmative determination), then the process determines that said inspection plane TS of the wafer W has "a defect existing" (Step 1056), and returns out of the sub routine. That is, if any one of the images to be inspected is not approximately matching to the reference image, the process determined that there is "a defect existing".

Although in the above embodiment, the inspection method has been described in conjunction with the electron beam apparatus of the multi-beam type, one selected from a variety of types, the inspection method according to this embodiment is also applicable to, for example, an electron beam apparatus of the scanning type as illustrated in FIG. 45. However, herein, an illustration of such electron beam apparatus should be omitted for the simplicity.

It is to be appreciated that although in the above description for the embodiment, each of the electron beam apparatuses having individually a characteristic portion has been distinctively explained, a single electron beam apparatus may include a plurality of characteristic portions described above in combination.

Effect of the Invention

According to a method for inspecting a substrate, a substrate inspection apparatus and a charged particle beam apparatus to be used in said substrate inspection apparatus, the following effect may be brought about.

(1) Since the electron beam consisting of a plurality of primary charged particle beams is irradiated onto and thereby to scan the sample all at once so as to obtain a plurality of sub-image data, and said sub-image data are rearranged based on the consideration of the X-Y coordinates thereof and then synthesized so as to obtain the image data for the region to be inspected on the wafer, throughput of the apparatus can be increased distinctively.

(2) Since the electron gun for emitting the charged particle beam has been designed so as to be operated in the space charge limited region, the S/N ratio can be increased to a great degree as compared with the case where the electron gun is operated in the temperature limited region according to the prior art. Accordingly, the S/N ratio of equivalent level to that having accomplished by the prior art can be obtained with lower beam current.

(3) Since even if a plurality of primary electron beams are used to scan the sample wafer all at once, the S/N ratio of a predetermined level can be obtained with still lower beam current, therefore a blur of the beam due to the space charge effect can be reduced to negligibly low level.

(4) Since the electron beam apparatus can be operated by quickly selecting either of a mode allowing for a precise evaluation yet with a small throughput or another mode allowing for a rough evaluation still with a large throughput, the efficient inspection or evaluation of the sample can be accomplished.

(5) Since the electrostatic lens is made by machining a single block of insulating material, and thereby the high precision lens of smaller diameter can be produced, the electron beam apparatus can be made compact and a plurality of optical columns can be arranged collectively for the wafer having a large diameter thus to accomplish an inspection and/or evaluation with high throughput.

(6) Since the circuit pattern formed on a surface of the sample is captured as the rectangular pattern information rather than the 0 and 1 binary information, it will become possible to improve a capacity of a memory for accumulating said image patterns, a rate of data transmission and a rate of data comparison to a great degree (this effect may appear significant specifically in a layer of lower pattern density such as a contact hole layer or a gate layer).

(7) Since at least one step of lens is used to magnify the secondary electron image, the focusing condition and/or the magnification for the secondary optical system is made adjustable separately from the adjustment of the lens condition for the primary optical system, therefore any offsets from those design values can be compensated and also any detected defects can be classified so as to detect a critical defect accurately and quickly.

(8) Since in the semiconductor manufacturing process, the inspection can be applied intensively only to a region where the defect is apt to occur, the inspection time can be shortened and substantially all the defects required to be detected can be accordingly detected.

(9) Since the bulk material of highly rigid SiC ceramic has been employed for the laser reflection mirror to be used in the laser interferometer, a distortion or a bowing of the mirror surface can be eliminated thus to improve a precision of flatness thereof without thickening the base body and also an erroneous detection in the position measurement can be prevented, and in addition, the weight of the stage as well as a space necessary for moving the stage can be reduced.

Further, since the laser reflection mirror according to the present invention is made in such a manner that the SiC ceramic base body is treated with a SiC film deposition to be covered therewith and then is polished to be a mirror-surface, therefore such an advantageous effect can be provided in that there is no fear of film stripping due to the aging. Still further, in the film deposition of SiC, if the SiC is deposited from various directions diagonal with respect to the surface of the base body, then a concave problem in the mirror surface caused by a void can be appropriately dissolved thus to maintain the high level of flatness on the mirror surface.

Further, since a portion common to the primary and the secondary optical systems has been minimized while satisfying the requirement, in addition to the effects described above, there has been provided another advantage that the primary and the secondary optical systems can be adjusted almost independently, and in that case, a cross talk between electron beams can be eliminated by making a spacing between the primary electron beams greater than a resolution of the secondary optical system as converted into a surface of the sample.

(10) Since a single electron optical column has been provided with at least one step of axially symmetric lens which is made by machining a block of ceramic and selectively applying a metal coating onto a surface thereof so as to accomplish a reduced outer diameter, in addition to the effects described above, there has been provided another advantage that a plurality of electronic-optical optical columns can be arranged in parallel over one piece of sample thus to improve the throughput of the inspection or evaluation of the sample.

(11) Further, according to the device manufacturing method of the present invention, since the above-described electron beam apparatus can be used to evaluate the wafer during being processed or after having been processed with high throughput as well as with high level of accuracy, such advantageous effects can be obtained that a yield of the product is improved and the delivery of any defective products is prevented.

(12) Since a killer defect and a non-killer defect can be distinguished from each other automatically even for a region having a minimum line width of not greater than 0.1 micron, it will become possible to provide a highly reliable defect inspection.

(13) Since a new pattern for either of a killer defect and a non-killer defect can be added into a database at each time when it has been found during a defect inspection period, it will become possible to provide a user friendly apparatus.

(14) Since the image data obtained from the adjacent secondary electron beams can be used to detect a mismatching portion and/or a defect, it will become possible to reduce a memory capacity for accumulating the image data.

(15) Since at least the outer side of the electrostatic lens to be used as the objective lens has been made of ceramic material having a low coefficient of linear expansion and further the stationary laser mirror is attached to this ceramic material or the ceramic material itself has been mirror-finished to form the stationary laser mirror, therefore it will be possible to provide an accurate evaluation of the sample even in the circumstance of low stability in temperature or in the case of relative vibration occurring between the optical system and the sample chamber.

(16) Since a single unit of apparatus can perform a multi-purpose inspection, measurement and evaluation including a defect inspection, a defect reviewing, a pattern line width measurement, and a pattern potential measurement, such a problem can be prevented that a large foot print in a clean room has been occupied by the inspection apparatus, and as a result, a larger number of device manufacturing apparatuses is allowed to be arranged therein, thereby providing an efficient way for using the clean room.

Further, with a plurality of optical columns to be arranged and a multi-beam for irradiating the sample surface and correspondingly a plurality of detecting elements to be arranged for each of the optical columns, a throughput of the inspection process (a volume of inspection per unit time) can be increased.

(17) Since the electron beam apparatus and the inspection apparatus can be made compact and at the same time a throughput of the electron beam apparatus can be matched with a throughput of the processing apparatus of the wafer, and thereby an operation in the processing apparatus can be checked at real time when the wafer containing the defect is detected, such a fear can be reduced that the wafers containing defects might be undesirably fabricated continuously.

(18) Since the stage can exhibit a highly precise positioning ability within the vacuum atmosphere and further the pressure in the charged particle beam irradiating location is hardly increased, the processing with the charged particle beam against the sample can be performed with high level of accuracy.

(19) The gas which has been desorbed from the hydrostatic bearing support section is almost completely blocked by the divider and thereby it hardly run over the divider to reach onto the charged particle beam irradiating region side. This can help further stabilize a vacuum level in the charged particle beam irradiating location.

(20) Since an inspection apparatus can be provided, in which the stage has a highly accurate positioning function and a vacuum level in the charged particle beam irradiating region is stable, it will be possible to provide the inspection apparatus with higher inspection performance and without any fear of contamination to the sample.

(21) Since such an exposing apparatus can be provided, in which the stage has a highly accurate positioning function and a vacuum level in the charged particle beam irradiating region is stable, it will be possible to provide the exposing apparatus with higher exposing accuracy and without any fear of contamination to the sample.

(22) The stage having a similar configuration to the stage of the hydrostatic bearing type which has been typically used in the atmosphere (a stage supported by the hydrostatic bearing having no differential pumping mechanism) can be used to provide a stable processing by the charged particle beam against a sample on the stage.

(23) Since it has become possible to minimize the affection to the vacuum level in the charged particle beam irradiating region, the processing by the charged particle beam against the sample can be stabilized.

(24) It has become possible to provide at a low price the exposing apparatus in which the stage has a highly accurate positioning function and a vacuum level in the charged particle beam irradiating region is stable.

(25) Since the present invention allows a plurality of images to be taken for a plurality of regions to be inspected each displaced from others while partially superimposing with each other on the sample and also allows each of these images subject to the inspection to be compared with the reference image thus to detect a defect in the sample, therefore such an advantageous effect can be obtained that a deterioration in the defect detecting accuracy due to the position mismatch between the image subject to the inspection and the reference image is prevented.

(26) Since the present invention allows the above-described charged particle beam apparatus to be used to evaluate the wafer during being processed or after having been processed, such an advantageous effect has been obtained that the highly accurate evaluation may be accomplished, a yield in the device manufacturing process may be improved and any defective products can be prevented from being delivered.

What is claimed is:

1. A substrate inspection method comprising:
    emitting a primary charged particle beam from a charged particle beam source, wherein said charged particle beam source is actuated in a space charge limited region, wherein a shot noise reduction factor is smaller than 1 and said charge particle beam source has a pointed cathode;
    focusing said emitting charged particle beams into a fine beam;
    irradiating and scanning said fine charged particle beam onto a substrate through a primary optical system;
    introducing a secondary charged particle beam into a secondary charge particle beam detector, said secondary charged particle beam being emitted from said substrate by said irradiation of said primary charged particle beam;
    detecting said secondary charged particle beam having been introduced into said secondary charge particle beam detector and converting said detected secondary charged particle beam into an electric signal; and
    processing said electric signal to evaluate said substrate, wherein said shot noise reduction factor is defined by the following equation, $$S/N = n^{1/2}/(\Gamma * 2^{1/2})$$

where, S/N is signal to noise ratio, $\Gamma$ is shot noise reduction factor, and n is the number of detected secondary electrons per pixel.

2. A substrate inspection method according to claim 1, wherein the primary charged particle beam emitted from said charged particle beam source is irradiated onto a multi aperture plate having a plurality of apertures, and a plurality of charged particle beams having passed through said plurality of apertures are irradiated onto a substrate surface.

3. A substrate inspection method according to claim 1, further comprising:
    detecting the secondary charged particle beam emitted from said substrate to obtain image data; and
    re-arranging said obtained image data to generate image data of an inspection region on the substrate.

4. A substrate inspection method according to claim 1, further comprising:
    storing in advance reference image data with respect to the substrate to be evaluated; and
    evaluating the substrate by comparing said image data generated by an image source with said stored reference image data.

5. A substrate inspection method according to claim 2, further comprising:
    obtaining respective sub-image data by detecting said secondary charged particle beam emitted from a plurality of beams of said substrate;
    wherein said substrate is controlled so as continuously move in the Y-axis direction,
    respective charged particle beams are driven to simultaneously scan in the X-axis direction such that a scanning pitch of a plurality of primary charged particle beams on said substrate are arranged with equal spacing therebetween.

6. A substrate inspection method according to claim 1, wherein a lens condition or an axial alignment condition of said primary and said secondary optical systems corresponding to a pixel size for scanning and irradiating said substrate are stored.

7. A substrate inspection method, according to claim 1, further comprising:
    converting said electric signal into a pattern information; and
    comparing said pattern information with a reference pattern.

8. A substrate inspection method according to claim 1, further comprising:
    converting said electric signal received from said detection section into binary information;
    converting said binary information into a rectangular pattern information; and
    comparing said rectangular information with a reference pattern.

9. A substrate inspection method according to claim 1, further comprising:
    storing a reference image corresponding to said image of said substrate;
    reading out said stored reference image;
    comparing said image of said substrate with said readout reference image and detecting portions differing between each of said images; and
    classifying said different portions into such defects including at least short-circuit, disconnection, convex, chipping, pinhole and isolation.

* * * * *